(12) United States Patent
Araki et al.

(10) Patent No.: US 8,476,490 B2
(45) Date of Patent: Jul. 2, 2013

(54) METHOD FOR PRODUCTION OF MOTH ORCHID HAVING MODIFIED FLOWER COLOR

(75) Inventors: Satoshi Araki, Kusatsu (JP); Takanori Suzuki, Kusatsu (JP); Kouichi Katayama, Kusatsu (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 468 days.

(21) Appl. No.: 12/596,739

(22) PCT Filed: Apr. 25, 2008

(86) PCT No.: PCT/JP2008/058126
§ 371 (c)(1),
(2), (4) Date: Oct. 20, 2009

(87) PCT Pub. No.: WO2008/136434
PCT Pub. Date: Nov. 13, 2008

(65) Prior Publication Data
US 2011/0179524 A1 Jul. 21, 2011

(30) Foreign Application Priority Data

Apr. 26, 2007 (JP) .................................. 2007-116396

(51) Int. Cl.
*A01H 5/00* (2006.01)
*C12N 15/82* (2006.01)

(52) U.S. Cl.
USPC .......................................... 800/282; 800/323

(58) Field of Classification Search
None
See application file for complete search history.

(56) References Cited

U.S. PATENT DOCUMENTS

| | | | |
|---|---|---|---|
| 6,080,920 A | 6/2000 | Holton | |
| 6,114,601 A | 9/2000 | Kikuchi et al. | |
| PP13,092 P2 * | 10/2002 | Glancy | |
| 6,465,630 B1 * | 10/2002 | Choi et al. | 536/23.1 |
| 6,570,064 B1 * | 5/2003 | Allen et al. | 800/278 |
| 6,660,908 B2 * | 12/2003 | Choi et al. | 800/282 |
| 6,774,285 B1 * | 8/2004 | Brugliera et al. | 800/298 |
| 7,612,257 B2 | 11/2009 | Brugliera et al. | |
| 2002/0120954 A1 | 8/2002 | Choi et al. | |
| 2002/0120959 A1 | 8/2002 | Choi et al. | |
| 2007/0033674 A1 | 2/2007 | Brugliera et al. | |
| 2010/0107277 A1 | 4/2010 | Brugliera et al. | |
| 2011/0126320 A1 | 5/2011 | Tanaka et al. | |

FOREIGN PATENT DOCUMENTS

| | | |
|---|---|---|
| EP | 1 182 257 | 2/2002 |
| EP | 1 652 916 A1 | 5/2006 |
| EP | 2 143 322 | 4/2008 |
| JP | 11-505116 | 5/1999 |
| JP | 2006-512057 | 4/2006 |
| JP | 2007-116396 | 4/2007 |
| WO | 96/36716 | 11/1996 |
| WO | 97/32023 | 9/1997 |
| WO | WO 97/32023 | * 9/1997 |
| WO | 2004/020637 | 3/2004 |
| WO | 2005/017147 | 2/2005 |

OTHER PUBLICATIONS

Tanaka et al. Genetic engineering in floriculture, 2005, Plant cell, Tissue and Organ Culture, 80:1-24.*
Tanaka et al. Molecular and Biochemical Characterization of Three Anthocyanin Synthetic Enzymes from Gentuana triflora, 1996, Plant Cell Physiol. 37(5) 711-716.*
Halpin, Enabling technologies for manipulation multiple genes on complex pathways, 2001, Plant Molecular Biology 47:295-310.*
Su et al (Biotechnology Letter 25:1933-1939, 2003).*
GenBank accession No. DQ218417, first available Oct. 15, 2005).*
Ueyama et al (Plant Science 163 (2002) 253-263.*
Forkman et al (Current Opinion in Biotechnology 2001, 12:155-160.*
Belarmino (Plant Cell Reports 2000 p. 435-442).*
Suzuki (GenBank accession No. AB012924, first available Jan. 17, 2001).*
Chen et al (GenBank accession No. AY997840, first available Apr. 26, 2005).*
Saito et al (The Plant Journal (1999) 17(2), 181-189).*
Helariutta et al (Plant Molecular Biology 22: 183-193, 1993).*
Su et al., Biotechnology Letters, vol. 25, p. 1933-1939, 2003.
Hieber et al., Planta, vol. 223, No. 3, p. 521-531, 2005.
Suzuki et al., Biotechnology & Biotechnological Equipment, vol. 14, No. 2, p. 56-62, 2000.
Kim et al., Plant Science, vol. 165, No. 2, p. 403-413, 2003.
U.S. Appl. No. 12/530,497 to Shunji Yuki et al., entitled "Flavonoid-3',5'-Hydroxylase Gene of Commelina Communis" which is the National Stage of PCT/JP2008/054653, filed Mar. 13, 2008.
International Search Report for PCT/JP2008/058126, mailed Jun. 24, 2008.
International Preliminary Report on Patentability for PCT/JP2008/058126, mailed Nov. 19, 2009.
Nakatsuka et al., Plant Sci., vol. 168, p. 1309-1318, 2005.
Seitz et al., Plant Mol. Biol., vol. 61, p. 365-381, 2006.
Johnson et al., Plant J., vol. 19, No. 1, p. 81-85, 1999.
Fukui et al., Phytochemistry, vol. 63, p. 15-23, 2003.
Altschul et al., Nucleic Acids Res., vol. 25, No. 17, p. 3389-3402, 1997.

(Continued)

*Primary Examiner* — Anne Kubelik
*Assistant Examiner* — Lee A Visone
(74) *Attorney, Agent, or Firm* — Greenblum & Bernstein, P.L.C.

(57) ABSTRACT

To provide a method for changing the flower color of a moth orchid, particularly a method for producing a moth orchid having a red or reddish flower color from a white moth orchid. A method for producing a moth orchid having a modified flower color, which comprises transfecting a moth orchid with a gene encoding a flavanone 3-hydroxylase, a gene encoding a flavonoid 3'-hydroxylase, a gene encoding a dihydroflavonol 4-reductase and a gene encoding an anthocyanidin synthase and expressing the genes.

13 Claims, 5 Drawing Sheets

OTHER PUBLICATIONS

Tokuhara and Mii, Plant Cell Reports, vol. 13, p. 7-11, 1993.
Hohn et al., "Cauliflower Mosaic Virus on Its Way to Becoming a Useful Plant Vector" Current Topics in Microbiology and Immunology, vol. 96, p. 194-236, 1982.
Gallie et al., Nucleic Acids Res., vol. 15, No. 8, p. 3257-3273, 1987.
Leon et al., Plant Physiology, vol. 95, p. 968-972, 1991.
Belarmino and Mii, Plant Cell Reports, vol. 19, p. 435-442, 2000.
Mishiba et al., Plant Cell Reports, vol. 24, p. 297-303, 2005.
Kobayashi et al., Science, vol. 286, p. 1960-1962, 1999.
International Search Report for PCT/JP2008/054653, mailed May 20, 2008.
International Preliminary Report on Patentability for PCT/JP2008/054653, mailed Oct. 8, 2009.
Yu et al., "Flavonoid Compounds in Flowers: Genetics and Biochemistry", Internet Citation, Jan. 1, 2006, pp. 282-292, XP007913213, Retrieved from the Internet: URL:http://www.danforthcenter.org/yu/pdf/e-flower-2006.pdf.
Holton et al., "Genetics and biochemistry of anthocyanin biosynthesis" Plant Cell, American Society of Plant Physiologists, Rockville, MD, US LNKD-DOI:10.1105/TPC.7.7.1071, vol. 7, No. 7, Jan. 1, 1955, pp. 1071-1083, XP002406599, ISSN: 1040-4651.
Wang et al., "Flavonoid-3',5'—hydroxylase from Phalaenopsis: A Novel Member of Cytochrome P450s, its cDNA Cloning, Endogenous Expression and Molecular Modeling", Biotechnology Letters, Kluwer Academic Publishers, DO LNKD-DOI:10.1007/S10529-005-5718-6, vol. 28, No. 5, Mar. 1, 2006, pp. 327-334, XP019231219, ISSN: 1573-6776.
Extended European Search Report that issued with respect to European Patent Application No. 08752160.5, dated Jul. 6, 2010.
Extended European Search Report that issued with respect to European Patent Application No. 08722057.0, dated Jul. 14, 2010.

\* cited by examiner

METHOD FOR PRODUCTION OF MOTH ORCHID HAVING MODIFIED FLOWER COLOR

SEQUENCE LISTING

The instant application contains a Sequence Listing which has been submitted in ASCII format via EFS-Web and is hereby incorporated by reference in its entirety. Said ASCII copy, created on Mar. 4, 2011, is named P37467.txt and is 126,562 bytes in size.

TECHNICAL FIELD

The present invention relates to a method for modify the flower color of a moth orchid by employing gene recombination technology. Particularly, it relates to a method for producing a moth orchid having a red flower color by introducing genes encoding enzymes related to biosynthesis of cyanidin into a moth orchid.

BACKGROUND ART

The color of flower is a particularly important character in ornamental plants, and flowers having various colors have been produced by cross breeding heretofore. However, when only a specific character such as flower color is introduced into a specific variety by cross breeding, because of uncertainty of cross breeding, it is necessary to repeat backcrossing over several generations, and a lot of effort and time are required. Further, a period of cross breeding varies depending on plant species, and in the cases of orchids such as moth orchids, which take a long time for blossom, it is practically impossible to produce a variety with a desired character only by cross breeding. Therefore, despite the demand of the market, it has been extremely difficult to change the flower color of a moth orchid to a desired color.

In recent years, it is possible to hybridize different species or genera by recombinant DNA technology, and it is expected to produce a new variety having a color which cannot be obtained by the conventional cross breeding.

The color of flower derives mainly from three types of pigments: anthocyanin, carotenoid and betalain. Among them, anthocyanin is the pigment having the broadest maximum absorption wavelength range and governs colors from red to blue. Anthocyanin is a kind of flavonoid and biologically synthesized through a metabolic pathway shown in FIG. 1. The color of anthocyanin substantially depends on its chemical structure, especially on the number of hydroxyl groups on the B ring. The hydroxylation of the B ring is catalyzed by a flavonoid 3'-hydroxylase (F3'H) and a flavonoid 3',5'-hydroxylase (F3'5'H). When there is neither F3'H activity nor F3'5'H activity in petal cells, pelargonidin (orange) is synthesized, and when there is F3'H activity, cyanidin (red) is synthesized. Further, when there is F3'5'H activity, delphinidin (blue) is synthesized. Therefore, in order to produce the red flower color, the role of F3'H is considered to be important.

In a case of genetic alteration of flower color, a blue rose was produced using a F3'5'H gene from *viola×wittrockiana* (Patent Document 1).

On the other hand, alteration of the flower color of a moth orchid from pink to magenta by overexpressing an endogenous gene was reported (Non-Patent Document 1).

Patent Document 1: WO2005/017147
Non-Patent Document 1: Su and Hsu, Biotechnology Letters (2003) 25: 1933-1939.

DISCLOSURE OF THE INVENTION

Object to be Accomplished by the Invention

It is an object of the present invention to identify the genes necessary for changing the flower color of a moth orchid, and provide a method for producing a moth orchid having a red flower color by changing the flower color of a moth orchid to red by introducing the genes into the moth orchid and expressing them.

Means to Accomplish the Object

The present inventors have conducted an extensive study on introduction of genes encoding enzymes related to biosynthesis of cyanidin, and as a result, they found that introduction of the genes encoding four enzymes downstream of the naringenin into petal cells of a white moth orchid enables the petal cells to synthesize the red pigment cyanidin. Thus, the present invention has been accomplished.

The present invention is based on the discovery and provides:

(1) A method for producing a moth orchid having a modified flower color, which comprises transfecting a moth orchid with a gene encoding a flavanone 3-hydroxylase, a gene encoding a flavonoid 3'-hydroxylase, a gene encoding a dihydroflavonol 4-reductase and a gene encoding an anthocyanidin synthase and expressing the genes.

(2) The method according to (1), wherein the gene encoding a flavonoid 3'-hydroxylase is derived from a moth orchid or *Gerbera*.

(3) The method according to (1), wherein the gene encoding a flavonoid 3'-hydroxylase has a DNA sequence represented by SEQ ID NO: 1 or 3.

(4) The method according to (1), wherein the gene encoding a dihydroflavonol 4-reductase is derived from *Gerbera* or *Torenia*.

(5) The method according to (1), wherein the gene encoding a dihydroflavonol 4-reductase has a DNA sequence represented by SEQ ID NO: 5 or 7.

(6) The method according to (1), wherein the gene encoding a flavanone 3-hydroxylase has a DNA sequence represented by SEQ ID NO: 9.

(7) The method according to (1), wherein the gene encoding an anthocyanin synthase has a DNA sequence represented by SEQ ID NO: 11 or 13.

(8) The method according to (1), wherein the gene encoding a flavonoid 3'-hydroxylase is derived from a moth orchid or *Gerbera*, and the gene encoding a dihydroflavonol 4-reductase is derived from *Gerbera* or *Torenia*.

(9) The method according to (1), wherein the gene encoding a flavonoid 3'-hydroxylase has a DNA sequence represented by SEQ ID NO: 1 or 3, and the gene encoding a dihydroflavonol 4-reductase has a DNA sequence represented by SEQ ID NO: 5 or 7.

(10) The method according to (1), wherein the gene encoding a flavanone 3-hydroxylase has a DNA sequence represented by SEQ ID NO: 9, and the gene encoding an anthocyanin synthase has a DNA sequence represented by SEQ ID NO: 11 or 13.

(11) The method according to (1), wherein the gene encoding a flavanone 3-hydroxylase has a DNA sequence represented by SEQ ID NO: 9, the gene encoding a flavonoid 3'-hydroxylase has a DNA sequence represented by SEQ ID NO: 1 or 3, the gene encoding a dihydroflavonol 4-reductase has a DNA sequence represented by SEQ ID NO: 5 or 7, and the gene encoding an anthocyanin synthase has a DNA sequence represented by SEQ ID NO: 11 or 13.

(12) The method according to (1), wherein the gene encoding a flavanone 3-hydroxylase has a DNA sequence represented by SEQ ID NO: 9, the gene encoding a flavonoid 3'-hydroxylase has a DNA sequence represented by SEQ ID NO: 1, the gene encoding a dihydroflavonol 4-reductase has a DNA sequence represented by SEQ ID NO: 5, and the gene encoding an anthocyanin synthase has a DNA sequence represented by SEQ ID NO: 11 or 13.

(13) A moth orchid having a modified flower color produced by the method as defined in any one of (1) to (12), a progeny having the same characters as the modified flower color, or its tissue.

In the present invention, "flavanone 3-hydroxylase" (hereinafter referred to also as F3H) is an enzyme which catalyzes a reaction which produces dihydrokaempferol from naringenin. "Flavonoid 3'-hydroxylase" (hereinafter referred to also as F3'H) is an enzyme which catalyzes a reaction which produces dihydroquercetin from dihydrokaempferol. "Dihydroflavonol 4-reductase" (hereinafter referred to also as DFR) is an enzyme which catalyzes a reaction which produces leucocyanidin from dihydroquercetin, and "anthocyanin synthase" (hereinafter referred to also as ANS) is an enzyme which catalyzes a reaction which produces cyanidin from leucocyanidin.

Effect of the Present Invention

According to the present invention, it is possible to produce a new variety of moth orchid having a pink or red flower color from a white moth orchid by changing the flower color, while maintaining the superiorities of other characters than flower color.

BEST MODES FOR CARRYING OUT THE INVENTION

Figure 1:
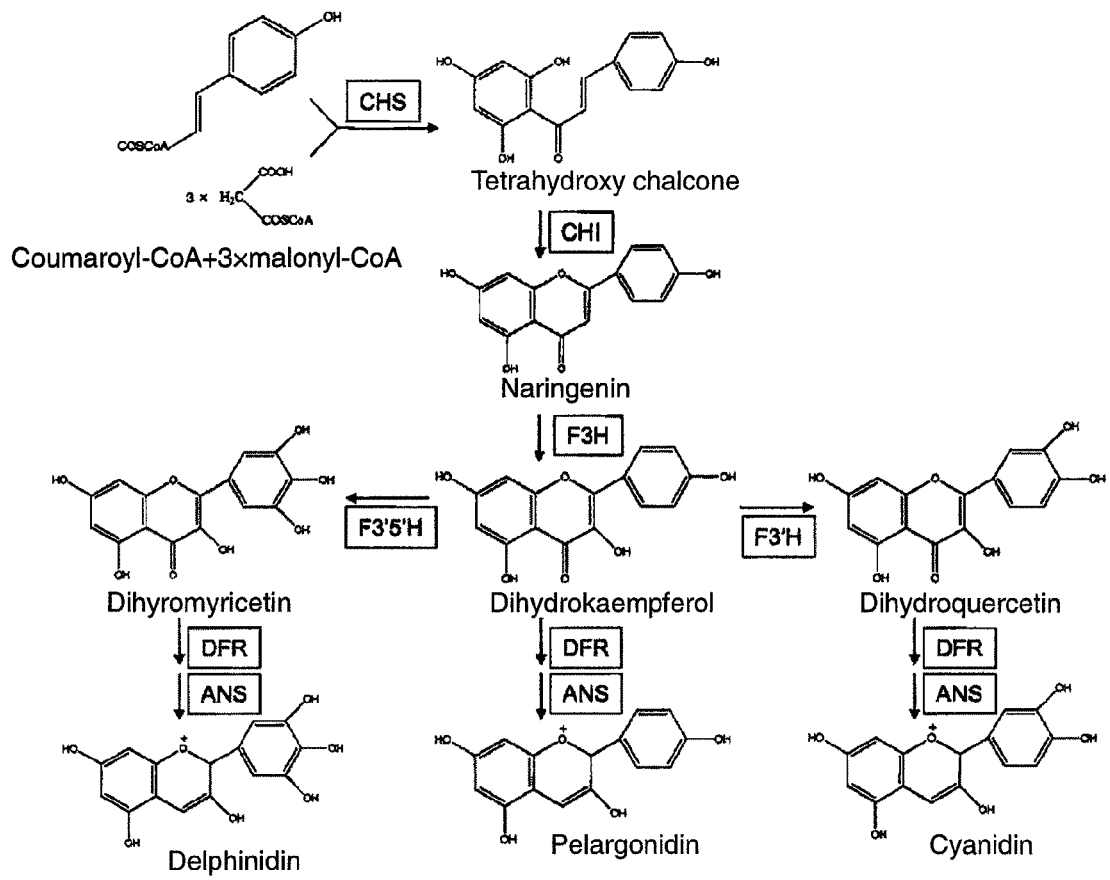
FIG. 1 is a synthetic pathway of anthocyanin.

Now, the present invention will be described in detail, and from these descriptions, other objects, characteristics, superiorities and aspects of the present invention will become apparent for those skills in the art. However, it should be understood that the descriptions of the present specification including the following explanations, specific examples, etc. show preferred embodiments and are made just for the sake of explanation. Those skilled in the art can make various changes and/or modifications (or alterations) of the invention within the concept and the scope of the present invention disclosed in the present specification. Further, all Patent Documents and references cited in the present specification are cited for the purpose of explanation, and it should be understood that their contents are included as a part of the present specification.

In the present invention, as the genes encoding F3H, F3'H, DFR and ANS, novel or conventional genes may be used. Among conventional genes, the gene encoding F3H may be a gene registered on GenBank (accession number: DQ394303, AY221246, AJ493133, AY641730, AF184270, AB078956, AB201760, AY669324, AF036093, AB211958, AB187027 or AB234905), the gene encoding F3'H may be a gene registered on GenBank (accession number: AAG49298, ABA64468, BAE47004, BAE47005, BAE47006, BAE71221, BAE72874, CAI54278, NP_920627 or Z17221), the gene encoding DFR may be a gene registered on GenBank (accession number: AB012924, AAB62873, AAC17843, AAD49343, AAQ83576, AAU93766, AAY32600, AAY32601, AAY32602, BAB40789, BAE79202 or Z17221), and the gene encoding ANS may be a gene registered on GenBank (accession number: AY585677, AY228485, AF015885, AY581048, U82432, AY695817, AB208689, AY997840, AY997842, AY382828, AY256380, AF026058, Y07955, AF384050, AB097216, AB087206, AB198869, AB044091, AY123768 or AB234906). Although the present specification describes isolation of a gene encoding F3'H (SEQ ID NO: 3), a gene encoding DFR (SEQ ID NO: 7) and a gene encoding ANS (SEQ ID NO: 13) from *Gerbera* by using primers designed from the sequences identified by accession numbers Z17221 and AY997842 and isolation of a gene encoding F3'H (SEQ ID NO: 87) and a gene encoding DFR (SEQ ID NO: 5) from *Torenia* by using primers designed from the sequences identified by accession numbers AB057672 and AB012924 in Examples 4 and 5, respectively, it is obvious that other conventional genes which can be isolated similarly can also be used in the present invention. Further, novel genes which were found in the present invention such as the gene encoding F3H (SEQ ID NO: 9), the gene encoding F3'H (SEQ ID NO: 1), the gene encoding DFR (SEQ ID NO: 15) and the gene encoding ANS (SEQ ID NO: 11) from a moth orchid may also be used.

In *Gerbera*, the gene encoding F3'H has a DNA sequence represented by SEQ ID NO: 3, the gene encoding DFR has a DNA sequence represented by SEQ ID NO: 7, and the gene encoding ANS has a DNA sequence represented by SEQ ID NO: 13. In *Torenia*, the gene encoding DFR has a DNA sequence represented by SEQ ID NO: 5. In a moth orchid, the gene encoding F3H has a DNA sequence represented by SEQ ID NO: 9, the gene encoding F3'H has a DNA sequence represented by SEQ ID NO: 1, and the gene encoding ANS has a DNA sequence represented by SEQ ID NO: 11.

In the present invention, as the gene encoding F3'H, it is preferred to use the gene derived from a moth orchid or *Gerbera*, especially the gene derived from a moth orchid. In the present invention, as the gene encoding DFR, it is preferred to use the gene derived from *Gerbera* or *Torenia*, especially the gene derived from *Torenia*. In the present invention, it is preferred that the gene encoding a flavonoid 3'-hydroxylase (F3'H) is the gene derived from a moth orchid or *Gerbera*, and the gene encoding a dihydroflavonol 4-reductase (DFR) is the gene derived from *Gerbera* or *Torenia*, because the flower color would be deep red.

In the present specification, the term, gene, is used in the broadest sense and means an isolated nucleic acid molecule having a DNA sequence encoding the amino acid sequence of the enzyme or a DNA sequence complementary thereto. The nucleic acid molecule may contain, in addition to the exon encoding the amino acid sequence, an intron, a 5' untranslated region and a 3' untranslated region.

In the present invention, a gene derived from a specific plant means a gene registered on GenBank as derived from the plant. The gene may be a spontaneously or artificially mutated gene having a high similarity to the registered gene. The high similarity means that the homology between the amino acid sequences encoded by them is at least 85%, preferably at least 90%, more preferably at least 95%, further preferably at least 98%.

In the present invention, genes are introduced into a moth orchid through a recombinant vector, especially an expression vector. The expression vector has an expression regulation region such as a promoter, a terminator, a DNA replication origin, etc. suitable for the host species into which the genes are introduced. The promoter may be a promoter which induces gene expression in petal cells, such as the CHS gene promoter in moth orchid or the cauliflower mosaic virus (CaMV) 35S promoter. The terminator may, for example, be the CHS gene terminator in moth orchid or the cauliflower mosaic virus (CaMV) 35S terminator.

Figure 7:
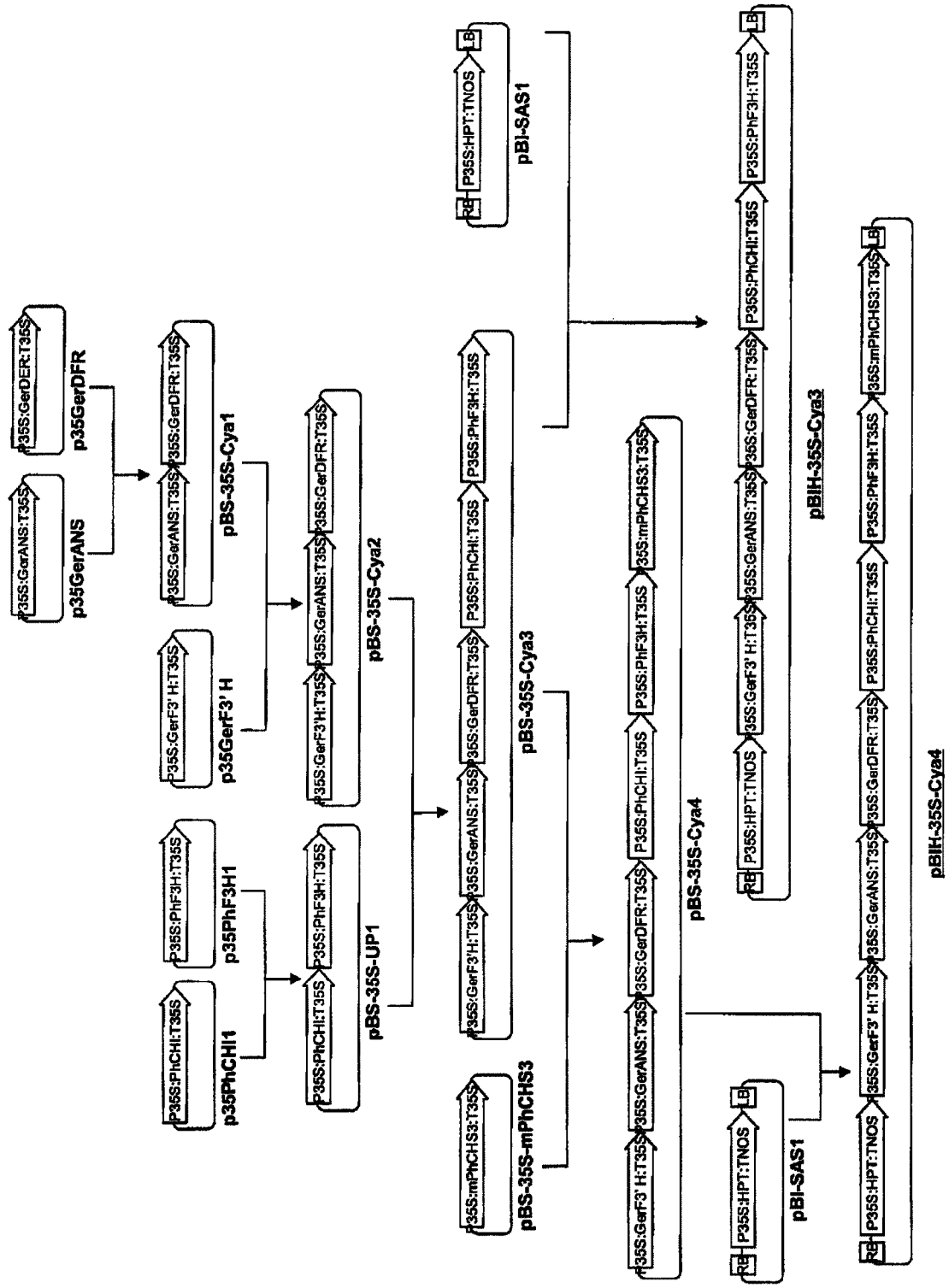
FIG. 7 is a schematic view showing a procedure for construction of DNA for transformation of moth orchid.
Figure 8:
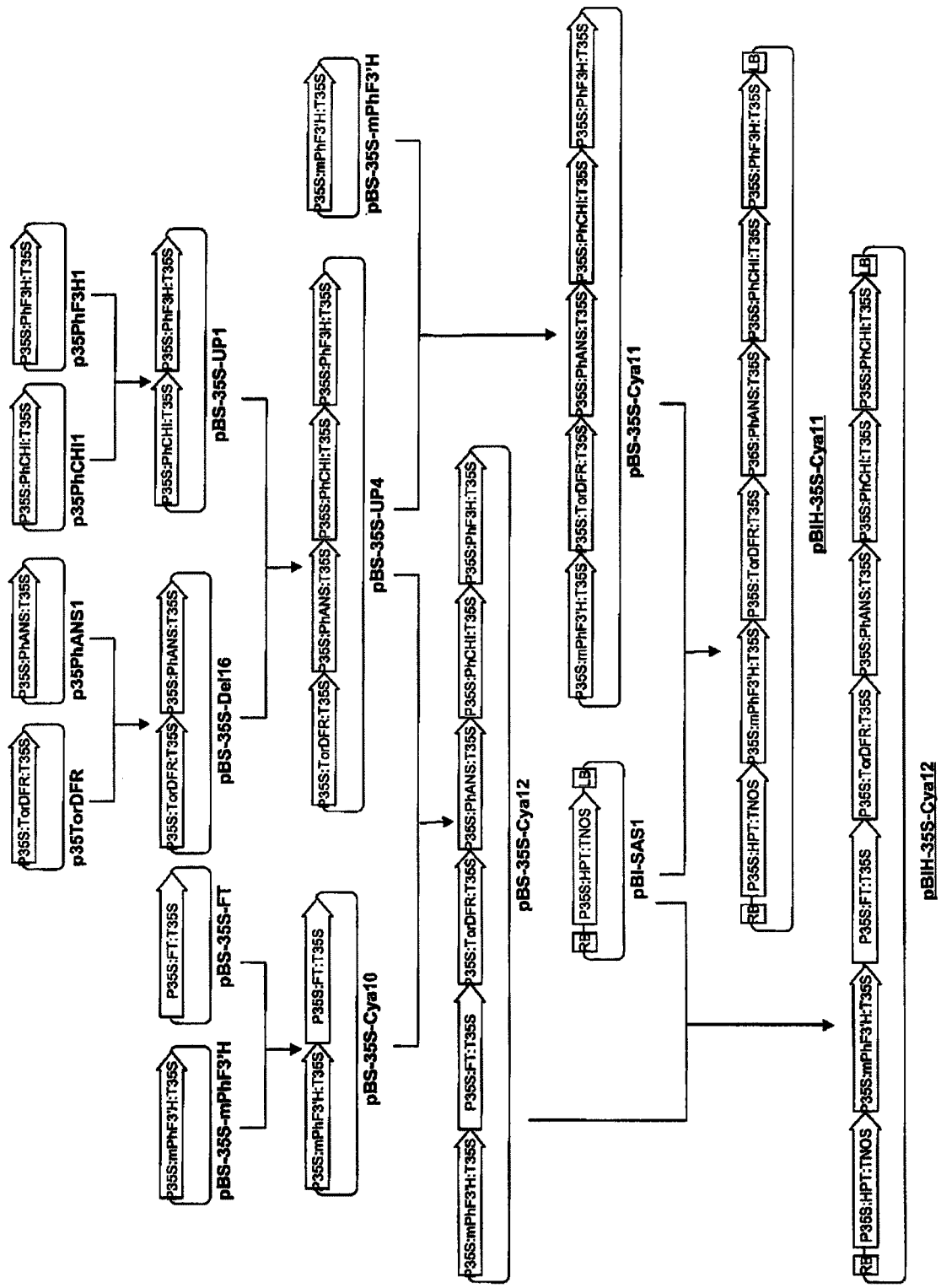
FIG. 8 is a schematic view showing a procedure for construction of DNA for transformation of moth orchid.

Specifically speaking, it is preferred to ligate each gene downstream of the 3' end of the promoter sequence, and add a transcription termination sequence downstream of the gene. The expression vector can be produced in accordance with a conventional method by using a restriction endonuclease, a ligase, etc. Further, transformation of hosts with the expression vector can also be carried out in accordance with a conventional method. In the present invention, for expression of genes in petal cells, microprojectile bombardment, *Agrobacterium*-mediated transformation, electroporation, PEG-mediated transformation or virus-mediated transformation may, for example, be used. FIG. 7 and FIG. 8 show examples of the vectors used for *Agrobacterium*-mediated transformation of a moth orchid.

The term, gene expression, is used in the broadest sense and may involve RNA production only or both RNA production and protein production. Gene expression in a plant may be constitutive, developmental or inducible, and may be systemic or tissue-specific.

In the present invention, plants to be transformed are Orchids, preferably moth orchids. Moth orchids include those of the genus *Phalaenopsis* and those of the genus *Doritaenopsis*.

The present invention relates to a method for producing a moth orchid having a red flower color by changing the flower color of a moth orchid by introducing a gene encoding F3H, a gene encoding F3'H, a gene encoding DFR and a gene encoding ANS into the moth orchid and expressing the genes. In more preferred embodiments of the present invention;

(1) the gene encoding F3'H is derived from a moth orchid or *Gerbera*;

(2) the gene encoding F3'H has a DNA sequence represented by SEQ ID NO: 1 or 3;

(3) the gene encoding DFR is derived from *Gerbera* or *Torenia*;

(4) the gene encoding DFR has a DNA sequence represented by SEQ ID NO: 5 or 7;

(5) the gene encoding F3'H is derived from a moth orchid or *Gerbera*, and the gene encoding DFR is derived from *Gerbera* or *Torenia*;

(6) the gene encoding F3'H has a DNA sequence represented by SEQ ID NO: 1 or 3, and gene encoding DFR has a DNA sequence represented by SEQ ID NO: 5 or 7; or (7) the gene encoding F3H has a DNA sequence represented by SEQ ID NO: 9, the gene encoding F3'H has a DNA sequence represented by SEQ ID NO: 1 or 3, the gene encoding DFR has a DNA sequence represented by SEQ ID NO: 5 or 7, and the gene encoding ANS has a DNA sequence represented by SEQ ID NO: 11 or 13.

EXAMPLES

Now, the present invention will be described in further detail with reference to Examples. However these Examples are simply given to describe the present invention and as references of embodiments. These examples are to describe specific embodiments of the present invention and are not to restrict or limit the scope of the present invention. Further, it should be understood that various modes based on the technical concept of the present specification may be possible.

Further, general methods required for recombination of gene such as cleavage and ligation of DNA, transformation of *E. coli*, gene sequencing and PCR were basically carried out in accordance with manuals of commercially available reagents or apparatus used for each operation or experimental manual (such as "Molecular Cloning: A Laboratory Manual (Third Edition, Sambrook and Russell, 2001, Cold Spring Harbor Laboratory Press)"). For PCR, GeneAmp PCR system 9700 (PE Applied Biosystems) was used. Unless otherwise specified, an apparatus was operated in accordance with a standard operation method described in a manual attached to the apparatus. Unless otherwise specified, all examples were carried out or may be carried out by using standard techniques, and such techniques are well known and common to those skills in the art.

As a homology searching program for examining an amino acid sequence encoded by the novel gene of the present invention and known amino acid sequences, BLASTP 2.2.15 (http://www.ddbj.nig.ac.jp/search/blast-j.html, Document: Altschul et al., Nucleic Acids Res. (1997) 25: 3389-3402) was used. Here, homology is the degree of similarity of amino acids over the entire sequence, and its value is obtained by aligning an amino acid sequence encoded by the novel gene and known amino acid sequences in order of the high similarity, and dividing the number of the homologous amino acids between them by the number of amino acids of the compared region. Here, high similarity is an alignment result output under a state (with gap, expected value 10, with filter) that the above BLASTP program parameter was defaulted. The homology described in the present Examples is one described with respect to a known amino acid sequence which showed the highest homology in the above homology analysis.

Example 1

Transfection of a Petal of Moth Orchid with a Gene

Unless otherwise specified in Examples of the present specification, petals of moth orchid were transfected with the various genes by the following gene transfection method, and their property was evaluated. All genes had a DNA structure having a promoter at 5' side and a terminator at 3' side and were introduced into petal cells in a form expressible in the cells.

A bud of moth orchid was sterilized with a 1 wt % of sodium hypochlorite aqueous solution for five minutes and washed with sterilized water 3 times. Then, the bud was resolved into a lateral sepal, dorsal sepal and petal, and the lateral sepal, dorsal sepal and petal were left on an agar medium containing NDM salt (Tokuhara and Mii, Plant Cell Reports (1993) 13: 7-11.) and 0.6 wt % agarose. Herein, a bud having a length of about 15 mm of a white moth orchid *Phal. amabilis* was used.

DNA to be introduced was purified by using Hi Speed Plasmid Midi Kit (QIAGEN), and genes were introduced by microprojectile bombardment. Further, when plural genes were introduced simultaneously, an equal mixture of solutions of DNAs of these genes was used as a DNA solution for transfection. DNA was adsorbed onto gold particles in the following ratio. A DNA solution in 20 µl of TE buffer (containing 2 µg plasmid DNA carrying a gene) was mixed with 50 µl of a gold particle suspension (the particle size: 1.0 µm, 60 mg/ml in 50% glycerol), and 50 µl of 2.5 M calcium chloride and 10 µl of 0.2 M spermidine were added to 70 µl of the mixture and suspended, to allow adsorption of DNA on the gold particles. After centrifugation, the supernatant was removed, and the particles were washed with 70% ethanol and 100% ethanol respectively. Then, the precipitate was suspended in 60 µl of 100% ethanol. The suspension was used as a sample solution, and 10 µl of the sample solution was used for one gene transfection. As the gene gun, IDERA GIE-III (TANAKA Co., Ltd.) was used. The gene transfection was carried out with a distance from a nozzle to a sample of 12 cm, under a reduced pressure of −80 kPa, a helium gas pressure of 0.3 MPa with a spraying time of 0.025 second. After the gene transfection, petals were left on an NDM salt agar medium and cultured under a light-dark cycle (light intensity: 23 µmol/m$^2$/s, light period: 16 hours, dark period: 8 hours) at 25° C.

Example 2

Figure 2:
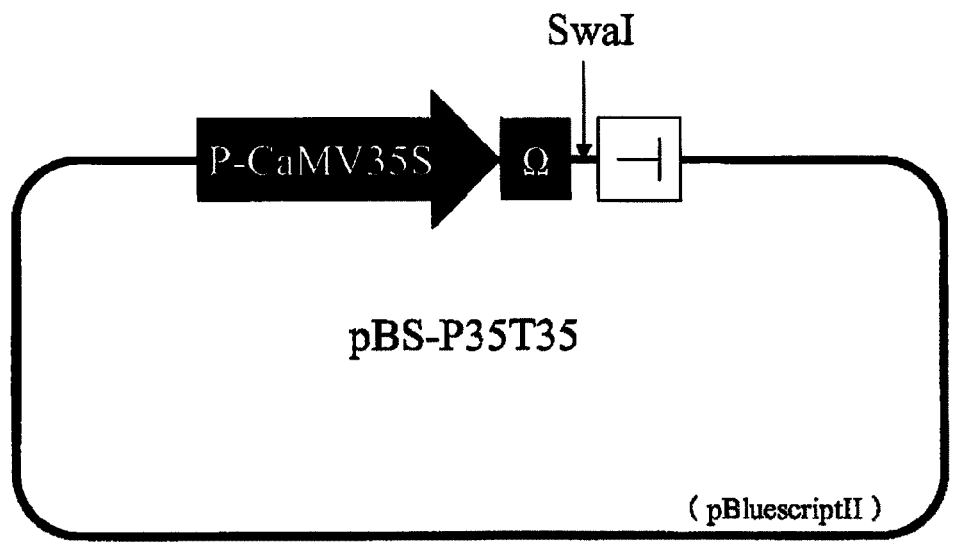
FIG. 2 is a plasmid vector used for transfecting a petal with a gene. P-CaMV35S is a cauliflower mosaic virus 35S promoter. Ω is an omega sequence of tobacco mosaic virus. T is a transcription termination sequence derived from a cauliflower mosaic virus.

Preparation of an Expression Vector (pBS-P35T35) for Gene Transfection pBS-P35T35 is a plasmid having the cauliflower mosaic virus 35S promoter (Hohn et al., Curent Topics in Microbiology and Immunology (1982) 96: 194-236), an omega sequence of tobacco mosaic virus (Gallie et al., Nucleic Acids Research (1987) 15: 3257-3273), a restriction endonuclease SwaI site and the cauliflower mosaic virus 35S terminator in this order in pBluescriptIISK—(Stratagene) (FIG. 2). A plasmid having substantially the same function as pBS-P35T35 can be constructed as follows.

An oligonucleotide SAS-S (5'-CTAGCTAGCG-GCGCGCCTGCAGGATATCATTTAAATCCCGGG-3'; SEQ ID NO: 17) and an oligonucleotide SAS-AS (5'-CCCGGGATTTAAATGATATCCTGCAG-GCGCGCCGCTAGCTAG-3'; SEQ ID NO: 18) were thermally denatured, then gradually cooled to room temperature and treated with NheI, and the resulting fragment was ligated between the XbaI-EcoRV sites of pBluescriptIISK—(Stratagene) to prepare a plasmid DNA with a modified restriction site, pBS-SAS. PCR was carried out by using a cauliflower mosaic virus genome DNA (GenBank accession V00140) as the template, a primer T-CaMV35S-SseI-F (5'-AACCTG-CAGGAAATCACCAGTCTCTCTCTA-3'; SEQ ID NO: 19) and a primer T-CaMV35S-AscI-R (5'-GGCGCGCCATC-GATAAGGGGTTATTAG-3'; SEQ ID NO: 20), and the amplified region was treated with restriction endonucleases Sse83871 and AscI. The resulting fragment was ligated between the Sse8387'-AscI sites of pBS-SAS to prepare pBS-T35S. The cauliflower mosaic virus 35S promoter and the tobacco mosaic virus omega sequence were cut out from pJD301 (Leon et al., Plant Physiology (1991) 95: 968-972) with HindIII and HincII and ligated between the HindIII-SmaI sites of pBS-T35S to prepare an expression vector (pBS-P35T35).

Isolation of the genes used in the Examples and construction of the DNAs introduced into plant cells are described below.

Example 3

Isolation of the Moth Orchid CHS, CHI, F3H, F3'H, DFR and ANS Genes and Preparation of DNA for Transient Expression (1) Isolation of the Moth Orchid CHS Gene (PhCHS3)

Total RNA was isolated from petals of moth orchid (*Dtps. Sogo Vivien×Dtps. Sogo Yenlin*) just before flowering by using RNeasy Plant Mini Kit (QIAGEN) and used as the template to prepare cDNA by SuperscriptII First-Strand Synthesis System (Invitrogen). Then, RT-PCR was carried out by using this cDNA as the template. In the PCR, PhCHS3 F1 (5'-AAGCTTGTGAGAGACGACGGA-3'; SEQ ID NO: 21) and PhCHS3 R1 (5'-TGGCCCTAATCCTTCAAATT-3'; SEQ ID NO: 22) designed from a known moth orchid CHS gene (PhCHS) sequence (GenBank accession No.: DQ089652) were used as the primers. The reaction was carried out by repeating a step of 94° C. for 30 seconds, 55° C. for 30 seconds and 72° C. for 1 minute 25 cycles. Amplification was carried out again in the same reaction solution under the same conditions again using the reaction product as the template. The resulting reaction product was cloned into the SwaI site of pBS-P35T35 to obtain p35PhCHS3. Then, the full-length DNA sequence of the moth orchid CHS gene in p35PhCHS3 was determined (PhCHS3; SEQ ID NO: 23). p35PhCHS3 is DNA for expressing the moth orchid CHS gene in plant cells.

(2) Isolation of the Moth Orchid CHI Gene (PhCHI1)

Total RNA was isolated from, petals of moth orchid (*Dtps. Sogo Vivien×Dtps. Sogo Yenlin*) just before flowering by using RNeasy Plant Mini Kit (QIAGEN) and used as the template to prepare cDNA by SuperscriptII First-Strand Synthesis System (Invitrogen). Then, RT-PCR was carried out by using this cDNA as the template. Although CHI genes from various plants have been reported (GenBank accession Nos.: AY700850, AY086088, DQ160231, AJ004902, AF474923, XM_470129, U03433 and AB187026), in the PCR, CHI-dgF1 (5'-TTYCTCGSYGGBGCMGGYGWVMGVGG-3'; SEQ ID NO: 25) and CHI-dgR1 (5'-CMGGIGAIACVSCRT-KYTYICCRATVAT-3'; SEQ ID NO: 26) designed from the conventionally known CHI gene were used as the primers. In the reaction, a step of 94° C. for 30 seconds and 72° C. for 1 minute was repeated 5 cycles, a step of 94° C. for 30 seconds and 70° C. for 1 minute was repeated 5 cycles, and then a step of 94° C. for 30 seconds, 68° C. for 30 seconds and 72° C. for 1 minute was repeated 25 cycles. Further, Nested PCR was carried out by using the resulting reaction solution as the template, a primer CHI-dgF3 (5'-TMIKYWCMGGISMIT-TYGARAARYT-3'; SEQ ID NO: 27) and a primer CHI-dgR3 (5'-TYICCRATVATIGWHTCCARIAYBGC-3'; SEQ ID NO: 28). In the reaction, a step of 94° C. for 30 seconds, 60° C. for 30 seconds and 72° C. for 1 minute was repeated 25 cycles. The resulting reaction product was cloned into pCR4-TOPO (Invitrogen) to obtain PhCHIfrag 16, and a partial DNA sequence of PhCHIfrag 16 was determined (PhCHI partial sequence).

From the PhCHI partial sequence, the 3' sequence and the 5' sequence were analyzed by RACE. 3' RACE was carried out by using a primer designed from the PhCHI partial sequence, the above-mentioned RNA and GeneRacer kit (Invitrogen). The primers used in the PCR were PhCHI-GSP F1 (5'-ATGCTGCTGCCATTAACGGGTCA-3'; SEQ ID NO: 29) and GeneRacer 3' primer. In the reaction, a step of 94° C. for 30 seconds and 72° C. for 1 minute was repeated 5 cycles, a step of 94° C. for 30 seconds and 70° C. for 1 minute was repeated 5 cycles, and then a step of 94° C. for 30 seconds, 60° C. for 30 seconds and 72° C. for 1 minute was repeated 25 cycles. Further, Nested PCR was carried out by using the resulting reaction solution as the template, a primer PhCHI-GSP F2 (5'-TCCGAGAAGGTCTCCGGGAACT-3'; SEQ ID NO: 30) and GeneRacer 3' Nested primer. In the reaction, a step of 94° C. for 30 seconds, 60° C. for 30 seconds and 72° C. for 1 minute was repeated 25 cycles. The resulting reaction product was cloned into pCR4-TOPO (Invitrogen) to obtain PhCHI3'RACE23. The 3' DNA sequence of PhCHI3'RACE23 was determined (PhCHI 3'RACE sequence).

5'RACE was carried out by using a primer designed from the PhCHI partial sequence, the above-mentioned RNA and GeneRacer kit (Invitrogen). The primers used in the PCR were PhCHI-GSP R1 (5'-GCATTCGTCAGCTTCT-TGCTCTCT-3'; SEQ ID NO: 31) and GeneRacer 5' primer. In the reaction, a step of 94° C. for 30 seconds and 72° C. for 1 minute was repeated 5 cycles, a step of 94° C. for 30 seconds and 70° C. for 1 minute was repeated 5 cycles, and then a step of 94° C. for 30 seconds, 60° C. for 30 seconds and 72° C. for 1 minute was repeated 25 cycles. Further, Nested PCR was carried out by using the resulting reaction solution as the template, a primer PhCHI-GSP R2 (5'-ATCACATCAGTCT-CAGCCACA-3'; SEQ ID NO: 32) and GeneRacer 5' Nested primer. In the reaction, a step of 94° C. for 30 seconds, 60° C. for 30 seconds and 72° C. for 1 minute was repeated 25 cycles. The resulting reaction product was cloned into pCR4-TOPO (Invitrogen) to obtain PhCHI5'RACE54. The 5' DNA sequence of PhCHI5'RACE54 was determined (PhCHI5'RACE sequence).

The full length of the moth orchid CHI gene (PhCHI) was cloned on the basis of the PhCHI3'RACE sequence and the PhCHI5'RACE sequence. PCR was carried out by using the above-mentioned cDNA, a primer PhCHI init (5'-ATGGCA-GAAACAGTGGCGACGCCCA-3'; SEQ ID NO: 33) and a primer PhCHI term (5'-TCAAACGACTCCATCCTTGCTC-3'; SEQ ID NO: 34). In the reaction, a step of 94° C. for 30 seconds, 65° C. for 30 seconds and 72° C. for 1.5 minutes was repeated 45 cycles. The resulting reaction product was cloned into the SwaI site of pBS-P35T35 to obtain p35PhCHI1. Then, the DNA sequence of the full-length moth orchid CHI gene in p35PhCHI1 was determined (PhCHI1, SEQ ID NO: 35), and the gene having the sequence from moth orchid was found to be novel. Homology analysis indicated that the amino acid sequence encoded by the DNA sequence has 54% homology to the amino acid sequence (GenBank accession No.: DQ120521) encoded by the CHI gene of tea plant. p35PhCHI1 is DNA for expressing the moth orchid CHI gene in plant cells.

(3) Isolation of the Moth Orchid F3H Gene (PhF3H1)

Total RNA was isolated from petals of moth orchid (*Dtps. Sogo Vivien×Dtps. Sogo Yenlin*) just before flowering by using RNeasy Plant Mini Kit (QIAGEN) and used as the template to prepare cDNA by SuperscriptII First-Strand Synthesis System (Invitrogen). Then, RT-PCR was carried out by using this cDNA as the template. Although F3H genes from various plants have been reported (GenBank accession Nos.: DQ394303, AY221246, AJ493133, AY641730, AF184270, AB078956, AB201760, AY669324, AF036093, AB211958, AB187027 and AB234905), in the PCR, a primer F3H-dgF1 (5'-TIVGIGAYGARGABGARMGBCCIAA-3'; SEQ ID NO: 37) and a primer F3H-dgR1 (5'-ACBGCYYGRT-GRTCHGCRTTCTTRAA-3'; SEQ ID NO: 38) designed from the conventionally known F3H gene were used as the primers. In the reaction, a step of 94° C. for 30 seconds and 72° C. for 1 minute was repeated 5 cycles, a step of 94° C. for 30 seconds, and 70° C. for 1 minute was repeated 5 cycles, and then a step of 94° C. for 30 seconds, 68° C. for 30 seconds and 72° C. for 1 minute was repeated 25 cycles. Further, Nested PCR was carried out by using the resulting reaction solution as the template, a primer F3H-dgF3 (5'-AARYT-BRGKTTYGAYATGWCHGGIG-3'; SEQ ID NO: 39) and a primer F3H-dgR3 (5'-GGHWSRACVGTDATCCAIG-WBTT-3'; SEQ ID NO:40). In the reaction, a step of 94° C. for 30 seconds, 60° C. for 30 seconds and 72° C. for 1 minute was repeated 25 cycles. The resulting reaction product was cloned into pCR4-TOPO (Invitrogen) to obtain PhF3Hfrag 26, and a partial DNA sequence of PhF3Hfrag 26 was determined (PhF3H partial sequence).

From the PhF3H partial sequence, the 3' sequence and the 5' sequence were analyzed by RACE. 3' RACE was carried out by using a primer designed from the PhF3H partial sequence, the above-mentioned RNA and GeneRacer kit (Invitrogen). The primers used in the PCR were PhF3H-GSPF1 (5'-TTCTCATACCCAATCGGGAG-3'; SEQ ID NO: 41) and GeneRacer 3' primer. In the reaction, a step of 94° C. for 30 seconds and 72° C. for 1 minute was repeated 5 cycles, and a step of 94° C. for 30 seconds and 70° C. for 1 minute was repeated 5 cycles, and then a step of 94° C. for 30 seconds, 60° C. for 30 seconds and 72° C. for 1 minute was repeated 25 cycles. Further, Nested PCR was carried out by using the resulting reaction solution, a primer PhF3H-GSP F2 (5'-AATCGGGAGCCGCGATTACT-3'; SEQ ID NO: 42) and GeneRacer 3' Nested primer. In the reaction, a step of 94° C. for 30 seconds, 60° C. for 30 seconds and 72° C. for 1 minute was repeated 25 cycles. The resulting reaction product was cloned into pCR4-TOPO (Invitrogen) to obtain PhF3H3'RACE33. The 3' DNA sequence of PhF3H3'RACE33 was determined (PhF3H 3'RACE sequence).

5'RACE was carried out by using a primer designed from the PhF3H partial sequence, the above-mentioned RNA and GeneRacer kit (Invitrogen). The primers used in the PCR were PhF3H-GSPR1 (5'-TCTGTGTGGCGCTTCAGGCC-3'; SEQ ID NO: 43) and GeneRacer 5' primer. In the reaction, a step of 94° C. for 30 seconds and 72° C. for 1 minute was repeated 5 cycles, and a step of 94° C. for 30 seconds and 70° C. for 1 minute was repeated 5 cycles, and then a step of 94° C. for 30 seconds, 60° C. for 30 seconds and 72° C. for 1 minute was repeated 25 cycles. Further, Nested PCR was carried out by using the resulting reaction solution, PhF3H-GSP R2 (5'-TGAGGTCCGGTTGCGGGCATTTT-3'; SEQ ID NO: 44) and GeneRacer 5' Nested primer. In the reaction, a step of 94° C. for 30 seconds, 60° C. for 30 seconds and 72° C. for 1 minute was repeated 25 cycles. The resulting reaction product was cloned into pCR4-TOPO (Invitrogen) to obtain PhF3H5'RACE86. The 5' DNA sequence of PhF3H5'RACE86 was determined (PhF3H 5'RACE sequence).

The full length of the moth orchid F3H gene was cloned on the basis of the PhF3H 3'RACE sequence and the PhF3H 5'RACE sequence. PCR was carried out by using the above-mentioned cDNA, a primer PhF3H init. (5'-ATGGC-CCCAATACCATTCCTACCGA-3'; SEQ ID NO: 45) and a primer PhF3H term. (5'-CCTTAAGCTAAAATCTCATT-TAATGCCTTTGCTCC-3'; SEQ ID NO: 46). In the reaction, a step of 94° C. for 30 seconds, 65° C. for 30 seconds and 72°

C. for 1.5 minutes was repeated 40 cycles. The resulting reaction product was cloned into the SwaI site of pBS-P35T35 to obtain p35PhF3H1. Then, the DNA sequence of the full-length moth orchid F3H gene in p35PhF3H1 was determined (PhF3H1; SEQ ID NO: 9), and the gene having the sequence from moth orchid was found to be novel. Homology analysis indicated that the amino acid sequence encoded by the DNA sequence has 86% homology to the amino acid sequence (GenBank accession No.: X89199) encoded by the F3H gene of *Bromheadia finlaysoniana*. p35PhF3H1 is DNA for expressing the moth orchid F3H gene in plant cells.

(4) Isolation of the Moth Orchid F3'H Gene (PhF3'H)

Total RNA was isolated from petals of a bud of moth orchid (*Dtps. Queen Beer 'Mantenkou'*) just before flowering by using RNeasy Plant Mini Kit (QIAGEN) and used as the template to prepare cDNA by SuperscriptII First-Strand Synthesis System (Invitrogen). Then, RT-PCR was carried out by using this cDNA as the template. Although F3'H genes from various plants have been reported (GenBank accession Nos.: AAG49298, ABA64468, BAE47004, BAE47005, BAE47006, BAE71221, BAE72874, CAI54278 and NP_920627), in the PCR, a primer F3HDF3 (5'-GCI-TAYAAYTAYCARGAYYTIGTNTT-3'; SEQ ID NO: 47) and a primer F3HD-R4-2 (5'-GCICKYTGIARIGT-NARNCC-3'; SEQ ID NO: 48) designed from the above-mentioned F3'H genes were used as the primers. In the reaction, a step of 94° C. for 30 seconds, 48° C. for 30 seconds and 72° C. for 1 minute was repeated 40 cycles. Further, Nested PCR was carried out by using the resulting reaction solution, a primer F3HDF4 (5'-GAYYTIGTNTTYGCICCNTAYGG-3'; SEQ ID NO: 49) and a primer F3HD-R3-2 (5'-DATICK-ICKICCIGCNCCRAANGG-3'; SEQ ID NO: 50). In the reaction, a step of 94° C. for 30 seconds, 48° C. for 30 seconds and 72° C. for 1 minute was repeated 35 cycles. Nested PCR was carried out again by using the resulting reaction solution, a primer F3HDF5 (5'-GARTTYAARIIIATGGTIGTI-GARYTNATG-3'; SEQ ID NO: 51) and a primer F3HD-R1-3 (5'-GGRTCICKNGCDATNGCCC-3'; SEQ ID NO: 52). In the reaction, a step of 94° C. for 30 seconds, 48° C. for 30 seconds and 72° C. for 30 seconds was repeated 35 cycles. The resulting reaction product was cloned into pCR4-TOPO (Invitrogen) and designated as PhF3'H-D/pCR4. A partial DNA sequence of PhF3'H-D/pCR4 was determined (PhF3'H partial sequence).

From the PhF3'H partial sequence, the 3' sequence and the 5' sequence were analyzed by RACE.

3' RACE was carried out by using a primer designed from the PhF3'H partial sequence, the above-mentioned RNA and GeneRacer kit (Invitrogen). The primers used in the PCR were PhF3dH-F7 (5'-AGGGCGAAGTTAATGGTGGAG-GCAGTGATA-3'; SEQ ID NO: 53) and GeneRacer 3' primer. In the reaction, a step of 94° C. for 30 seconds and 72° C. for 2 minutes was repeated 5 cycles, and a step of 94° C. for 30 seconds and 70° C. for 2 minutes was repeated 5 cycles, and then a step of 94° C. for 30 seconds, 68° C. for 30 seconds and 72° C. for 2 minutes was repeated 25 cycles. Nested PCR was carried out by using the resulting reaction solution, a primer PhF3dH-F8 (5'-AAGTTAATGGTGGAGGCAGTGATAT-GCTGA-3'; SEQ ID NO: 54) and GeneRacer 3' Nested primer. In the reaction, a step of 94° C. for 30 seconds, 65° C. for 30 seconds and 72° C. for 2 minutes was repeated 25 cycles. The resulting reaction product was cloned into pCR4-TOPO (Invitrogen) and designated as PhF3'H 3'RACE/pCR4. The 3' DNA sequence of PhF3'H 3'RACE/pCR4 was determined (PhF3'H 3'RACE sequence).

5'RACE was carried out by using a primer designed from the PhF3'H partial sequence, the above-mentioned RNA and GeneRacer kit (Invitrogen). The primers used in the PCR were PhF3dH-R6 (5'-CACTGCCTCCACCATTAACT-TCGCCCTTCT-3'; SEQ ID NO: 55) and GeneRacer 5' primer. In the reaction, a step of 94° C. for 30 seconds and 72° C. for 1 minute was repeated 5 cycles, and a step of 94° C. for 30 seconds and 70° C. for 1 minute was repeated 5 cycles, and then a step of 94° C. for 30 seconds, 68° C. for 30 seconds and 72° C. for 1 minute was repeated 25 cycles. Nested PCR was carried out by using the resulting reaction solution, a primer PhF3dH-R5 (5'-CCTCCACCATTAACTTCGCCCTTCTC-TATT-3'; SEQ ID NO: 56) and GeneRacer 5' Nested primer. In the reaction, a step of 94° C. for 30 seconds, 65° C. for 30 seconds and 72° C. for 1 minute was repeated 25 cycles. The resulting reaction product was cloned into pCR4-TOPO (Invitrogen) and designated as PhF3'H 5'RACE/pCR4. The 5' DNA sequence of PhF3'H 5'RACE/pCR4 was determined (PhF3'H 5'RACE sequence).

The full length of PhF3'H gene was cloned on the basis of the PhF3'H 3'RACE sequence and the PhF3'H 5'RACE sequence. RT-PCR was carried out by using the above-mentioned RNA, a random hexamer, a primer PhF3dH-F11E4 (5'-AAGAAGCAAATGGCATTCTTAACCTACCTG-3'; SEQ ID NO: 57) and a primer PhF3dH-R7G11 (5'-TTAT-CACTGCCTCCACCATTAACTTCGCCC-3'; SEQ ID NO: 58) and Ready-To-Go You Prime First Strand Beads (Amersham Biosciences). In the reaction, a step of 98° C. for 10 seconds, 68° C. for 30 seconds and 72° C. for 1.5 minutes was repeated 35 cycles. The resulting reaction product was cloned into pCR4-TOPO (Invitrogen) and designated as PhF3'H/pCR4. The DNA sequence of the PhF3'H gene in PhF3'H/pCR4 was determined (PhF3'H; SEQ ID NO: 1), and the gene having the sequence from moth orchid was found to be novel. Homology analysis indicated that the amino acid sequence encoded by the DNA sequence has 59% homology to the amino acid sequence (GenBank accession No.: DQ787855) encoded by the F3'H gene from *Sorghum bicolor*. PhF3'H/pCR4 was cut with EcoRI, and the cohesive end of DNA fragment from the plasmid was blunted with Klenow fragment. The DNA fragment was inserted at the SwaI cleavage site of pBS-P35T35, and clones were screened for the cDNA inserted in the sense direction to construct pBS-35S-PhF3'H. pBS-35S-PhF3'H is DNA for expressing the moth orchid F3'H gene in plant cells.

(5) Isolation of the Moth Orchid DFR Gene (PhDFR)

Total RNA was isolated from petals in a bud of moth orchid (*Dtps. Queen Beer Mantenkou*) by using RNeasy Plant Mini Kit (QIAGEN) and used as the template to prepare cDNA by GeneRacer kit (Invitrogen). Then, RT-PCR was carried out by using this cDNA as the template. Although DFR genes from various plants have been reported (GenBank accession Nos.: AAB62873, AAC17843, AAD49343, AAQ83576, AAU93766, AAY32600, AAY32601, AAY32602, BAB40789 and BAE79202), in the PCR, DFRD-F1 (5'-TTY-CAYGTIGCIACNCCNATG-3'; SEQ ID NO: 59) and DFRD-R1 (5'-DATNGCRTCRTCRAACATYTC-3'; SEQ ID NO: 60) designed from the sequence of the above-mentioned DFR genes were used as the primers. In the reaction, a step of 94° C. for 30 seconds, 48° C. for 30 seconds and 72° C. for 1 minute was repeated 40 cycles. Nested PCR was carried out by using the resulting reaction solution as the template, a primer DFRD-F2 (5'-ATGAAYTTYCARWSIRARGAYCC-3'; SEQ ID NO: 61) and a primer DFRD-R2 (5'-RCAIATR-TAICKNCIRTTNGC-3'; SEQ ID NO:62). In the reaction, a step of 94° C. for 30 seconds, 48° C. for 30 seconds and 72° C. for 1 minute was repeated 40 cycles. Further, Nested PCR was carried out again by using the resulting reaction solution as the template, a primer DFRD-F3 (5'-GARAAYGARGT-NATHAARCC-3'; SEQ ID NO: 63) and a primer DFRD-R3 (5'-RTCRTCIARRTGNACRAAYTG-3'; SEQ ID NO:64). In the reaction, a step of 94° C. for 30 seconds, 48° C. for 30 seconds and 72° C. for 30 seconds was repeated 40 cycles. The resulting reaction product was cloned into pCR4/TOPO (Invitrogen) to obtain PhDFR-D/pCR4, and a partial DNA sequence of PhDFR-D/pCR4 was determined (PhDFR partial sequence).

From the PhDFR partial sequence, the 3' sequence and the 5' sequence were analyzed by RACE.

3' RACE was carried out by using a primer designed from the PhDFR partial sequence, the above-mentioned RNA and GeneRacer kit (Invitrogen). The primers used for the PCR were PhDFR-F1 (5'-GGTCATGCAAAAG-GTCGGGCAGCGTAA-3'; SEQ ID NO: 65) and GeneRacer 3' primer. In the reaction, a step of 94° C. for 30 seconds and 72° C. for 1 minute was repeated 5 cycles, a step of 94° C. for 30 seconds and 70° C. for 1 minute was repeated 5 cycles, and then a step of 94° C. for 30 seconds, 68° C. for 30 seconds and 72° C. for 1 minute was repeated 25 cycles. Further, Nested PCR was carried out by using the resulting reaction solution as the template, a primer PhDFR-F2 (5'-GTGATCTTCA-CATCTTCCGCAGGAACAGT-3'; SEQ ID NO: 66) and GeneRacer 3' Nested primer. In the reaction, a step of 94° C. for 30 seconds, 65° C. for 30 seconds and 72° C. for 1 minute was repeated 25 cycles. The resulting reaction product was cloned into pCR4/TOPO10 (Invitrogen) to obtain PhDFR3'RACE/pCR4, and the 3' DNA sequence of PhDFR3'RACE/pCR4 was determined (PhDFR3'RACE sequence).

5'RACE was carried out by using a primer designed from the PhDFR partial sequence, the above-mentioned RNA and GeneRacer kit (Invitrogen). The primers used in the PCR were PhDFR-R4 (5'-ATGATTCATTAAAAATC-CGAAAAAAAGACCACTACAA-3'; SEQ ID NO: 67) and GeneRacer 5' primer. In the reaction, a step of 94° C. for 30 seconds and 72° C. for 1 minute was repeated 5 cycles, a step of 94° C. for 30 seconds and 70° C. for 1 minute was repeated 5 cycles, and then a step of 94° C. for 30 seconds, 68° C. for 30 seconds and 72° C. for 1 minute was repeated 25 cycles. Further, Nested PCR was carried out by using the resulting reaction solution as the template, a primer PhDFR-R3 (5'-AACCATGCATAATAAAGCAGATGTGTAAAT-3'; SEQ ID NO: 68) and GeneRacer 5' Nested primer. In the reaction, a step of 94° C. for 30 seconds, 65° C. for 30 seconds and 72° C. for 1 minute was repeated 25 cycles. The resulting reaction product was cloned into pCR4/TOPO (Invitrogen) to obtain PhDFR 5'RACE/pCR4, and the 5' DNA sequence of PhDFR 5'RACE/pCR4 was determined (PhDFR 5'RACE sequence).

The full length of the moth orchid DFR gene was cloned on the basis of the PhDFR3'RACE sequence and the PhDFR 5'RACE sequence. RT-PCR was carried out by using the above-mentioned RNA, a primer PhDFR-F8A5 (5'-AAAAAATGGAGGATGTGAGGAAGGGTCCTGTT-3'; SEQ ID NO: 69), a primer PhDFR-R5 (5'-ACATGATTCAT-TAAAAATCCGAAAAAAAGACCA-3'; SEQ ID NO: 70) and Ready-To-Go You Prime First Strand Beads (Amersham Biosciences). In the reaction, a step of 98° C. for 30 seconds, 68° C. for 30 seconds and 72° C. for 1.5 minutes was repeated 35 cycles. The resulting reaction product was cloned into pBS-P35T35 to obtain p35PhDFR. Then, the DNA sequence of the full-length moth orchid DFR gene in p35PhDFR was determined (PhDFR; SEQ ID NO: 15), and the gene having the sequence from moth orchid was found to be novel. Homology analysis indicated that the amino acid sequence encoded by the DNA sequence has 86% homology to the amino acid sequence (GenBank accession No.: AF007096) encoded by the DFR gene of *Bromheadia finlaysoniana*. p35PhDFR is DNA for expressing the moth orchid DFR gene in plant cells.

(6) Isolation of the Moth Orchid ANS Gene (PhANS1)

Total RNA was isolated from petals of moth orchid (*Dtps. Sogo Vivien*×*Dtps. Sogo Yenlin*) just before flowering by using RNeasy Plant Mini Kit (QIAGEN) and used as the template to prepare cDNA by SuperscriptII First-Strand Synthesis System (Invitrogen). Then, RT-PCR was carried out by using this cDNA as the template. In the PCR, a primer ANS-dgF2 (5'-TICARGGBTAYGGIAGYARRYTIGCIRMYA-3'; SEQ ID NO: 71) and ANS-dgR2 (5'-GGYTCRCARAA-IAYIRCCCAIGADA-3'; SEQ ID NO: 72) designed from a known ANS gene were used as the primers. In the reaction, a step of 94° C. for 30 seconds, 60° C. for 30 seconds and 72° C. for 1.5 minutes was repeated 40 cycles. By using the resulting reaction solution as the template and the same primers again, a step of 94° C. for 30 seconds, 56° C. for 30 seconds and 72° C. for 1 minute was repeated 30 cycles. The resulting reaction product was cloned into pCR4/TOPO (Invitrogen) to obtain PhANSfrag10, and a partial DNA sequence of PhANSfrag10 was determined (PhANS partial sequence).

From the PhANS partial sequence, the 3' sequence and the 5' sequence were analyzed by RACE.

3' RACE was carried out by using a primer designed from the PhANS partial sequence, the above-mentioned RNA and GeneRacer kit (Invitrogen). The primers used in the PCR were PhANS3RACEGSP1 (5'-GCCCACACCGACGT-CAGCTCCCTCTCCT-3'; SEQ ID NO: 73) and GeneRacer 3' primer. In the reaction, a step of 94° C. for 30 seconds and 72° C. for 1.5 minutes was repeated 5 cycles, a step of 94° C. for 30 seconds and 70° C. for 1.5 minutes was repeated 5 cycles, and then a step of 94° C. for 30 seconds, 70° C. for 30 seconds and 72° C. for 1.5 minutes was repeated 25 cycles. Further, Nested PCR was carried out by using the resulting reaction solution as the template, a primer PhANS3RACEGSP2 (5'-CGTCGGGGATGCGCTCGAGATCCTCAGC-3'; SEQ ID NO: 74) and GeneRacer 3' Nested primer. In the reaction, a step of 94° C. for 10 seconds, 58° C. for 10 seconds and 72° C. for 1 minute was repeated 35 cycles. The resulting reaction product was cloned into pCR4/TOPO (Invitrogen) to obtain PhANS3'RACE37, and the 3' DNA sequence of PhANS3'RACE37 was determined (PhANS3'RACE sequence).

5'RACE was carried out by using a primer designed from the PhANS partial sequence, the above-mentioned RNA and GeneRacer kit (Invitrogen). The primers used in the PCR reaction were PhANS5RACEGSP1 (5'-AGTCCGCGGGT-TCAGTCGGCCAGATGGT-3'; SEQ ID NO: 75) and GeneRacer 5' primer. In the reaction, a step of 94° C. for 30 seconds and 72° C. for 1.5 minutes was repeated 5 cycles, a step of 94° C. for 30 seconds and 70° C. for 1.5 minutes was repeated 5 cycles, and then a step of 94° C. for 30 seconds, 70° C. for 30 seconds and 72° C. for 1.5 minutes was repeated 25 cycles. Nested PCR was carried out by using the resulting reaction solution as the template, a primer PhANS5RACEGSP2 (5'-CCGTCTTCTCCGGCGGGTA-GACGAGGTG-3'; SEQ ID NO: 76) and GeneRacer 5' Nested primer. In the reaction, a step of 94° C. for 10 seconds, 58° C. for 10 seconds and 72° C. for 1 minute was repeated 35 cycles. The resulting reaction product was cloned into pCR4/TOPO (Invitrogen) to obtain PhANS5'RACE15, and the 5' DNA sequence of PhANS5'RACE15 was determined (PhANS 5'RACE sequence). The full length of moth orchid ANS gene was cloned on the basis of the PhANS3'RACE sequence and the PhANS 5'RACE sequence. PCR was carried out by using the above-mentioned cDNA, a primer PhANS init (5'-ATGGCCACCAAAGCAATCCCACC-3'; SEQ ID NO: 77), and a primer PhANS term (5'-TCAATC-CACAGGCGCCTTCT-3'; SEQ ID NO: 78). In the reaction, a step of 94° C. for 30 seconds, 69° C. for 30 seconds and 72° C. for 1.5 minutes was repeated 35 cycles. The resulting reaction product was cloned into the SwaI site of pBS-P35T35 to obtain p35PhANS1. Then, the DNA sequence of the full-length ANS gene (PhANS1) in p35PhANS1 was determined (PhANS1; SEQ ID NO: 11), and the gene having the sequence from moth orchid was found to be novel. Homology analysis indicated that the amino acid sequence encoded by the DNA sequence has 58% homology to the amino acid sequence (GenBank accession No.: EF079869) encoded by the ANS gene of Anthurium. p35PhANS1 is DNA for expressing the moth orchid ANS gene in plant cells.

Example 4

Isolation of the *Gerbera* F3'H, DFR and ANS Genes and Preparation of an Expression Vector (1) Isolation of the *Gerbera* F3'H Gene (GerF3'H)

Total RNA was isolated from petals of a bud of a commercially available *Gerbera* hybrid and used as the template to prepare cDNA by SuperscriptII First-Strand Synthesis System (Invitrogen). Then, RT-PCR was carried out by using this cDNA as the template. In the PCR, GerF3H-F (5'-ATGACGCCTTTAACGCTCCT-3'; SEQ ID NO: 79) and GerF3H-R (5'-CTAGACCTTAGTCGTCTCATATACATG-3'; SEQ ID NO: 80) designed from a known *Gerbera* F3'H gene (GerF3'H) sequence (GenBank accession No.: Z17221) were used as the primers. In the reaction, a step of 98° C. for 10 seconds, 55° C. for 10 seconds and 72° C. for 1.5 minutes was repeated 45 cycles. The resulting reaction product was cloned into the SwaI site of pBS-P35T35 (p35GerF3'H) to obtain the *Gerbera* F3'H gene (SEQ ID NO: 3). p35GerF3'H is DNA for expressing the *Gerbera* F3'H gene in plant cells.

(2) Isolation of the *Gerbera* DFR Gene (GerDFR)

RT-PCR was carried out by using the cDNA obtained in Example 4(1) as the template. In the PCR, GerDFR-F (5'-ATGGAAGAGGATTCTCCGGC-3'; SEQ ID NO: 81) and GerDFR-R (5'-CTATTGGCCTTCTTTTGAACAACAAA-3'; SEQ ID NO: 82) designed from a known *Gerbera* DFR gene (GerDFR) sequence (GenBank accession No.: Z17221) were used as the primers. The reaction was carried out by repeating a step of 98° C. for 10 seconds, 55° C. for 10 seconds and 72° C. for 1 minute and 30 seconds 45 cycles. The resulting reaction product was cloned into the SwaI site of pBS-P35T35 to obtain a *Gerbera* DFR gene (p35GerDFR) (SEQ ID NO: 7). p35GerDFR is DNA for expressing the *Gerbera* DFR gene in plant cells.

(3) Isolation of the *Gerbera* ANS Gene (GerANS)

RT-PCR was carried out by using the cDNA obtained in Example 4(1) as the template. In the PCR, GerANS-F (5'-ATGGTGATTCAAGCAACCACA-3'; SEQ ID NO: 83) and GerANS-R (5'-CTAGTTTTGCATCACTTCGTCTTTAT-3'; SEQ ID NO: 84) designed from known *Gerbera* ANS gene (GerANS) sequence (GenBank accession No.: AY997842) were used as the primers. In the reaction, a step of 94° C. for 30 seconds, 56° C. for 30 seconds and 72° C. for 1 minute and 10 seconds was repeated 45 cycles. The resulting reaction product was cloned into the SwaI site of pBS-P35T35 to obtain *Gerbera* ANS gene (p35GerANS) (SEQ ID NO: 13). p35GerANS is DNA for expressing the *Gerbera* ANS gene in plant cells.

Example 5

Isolation of the *Torenia* F3'H and DFR Genes and Preparation of an Expression Vector (1) Isolation of the *Torenia* F3'H Gene (TorF3'H)

Total RNA was isolated from petals of a bud of a commercially available *Torenia*(*Torenia fournieri*) and used as the template to prepare cDNA by SuperscriptII First-Strand Synthesis System (Invitrogen). Then, RT-PCR was carried out by using this cDNA as the template. In the PCR reaction, TorF3H1-F (5'-ATGAGTCCCTTAGCCTTGATGAT-3'; SEQ ID NO: 85) and TorF3H1-R (5'-TTAATAGACAT-GAGTGGCCAACC-3'; SEQ ID NO: 86) designed from a known *Torenia* F3'H gene (TorF3'H) sequence (GenBank accession AB057672) were used as the primers. In the reaction, a step of 94° C. for 30 seconds, 55° C. for 30 seconds and 72° C. for 1 minute and 10 seconds was repeated 45 cycles. The resulting reaction product was cloned into the SwaI site of pBS-P35T35 to obtain a *Torenia* F3'H gene (p35TorF3'H) (SEQ ID NO: 87). p35TorF3'H is DNA for expressing the *Torenia* F3'H gene in plant cells.

(2) Isolation of the *Torenia* DFR Gene (TorDFR)

RT-PCR was carried out by using the cDNA obtained in Example 5(1) as the template. In the PCR, oligonucleotides TorDFR-F (5'-ATGAGCATGGAAGTAGTAGTACCA-3'; SEQ ID NO: 89) and TorDFR-R (5'-CTATTCTATCTTATGT-TCTCCATGG-3'; SEQ ID NO: 90) designed from a known *Torenia* DFR gene (TorDFR) sequence (GenBank accession AB012924) were used as the primers. In the reaction, a step of 94° C. for 30 seconds, 56° C. for 30 seconds and 72° C. for 1 minute and 10 seconds was repeated 45 cycles. The resulting reaction product was cloned into the SwaI site of pBS-P35T35 to obtain a *Torenia* DFR gene (p35TorDFR) (SEQ ID NO: 5). p35TorDFR is DNA for expressing the *Torenia* DFR gene in plant cells.

Example 6

Observation of Coloration of Petal Cells

The coloration of petals and petal cells was observed under a stereomicroscope SZX12 (OLYMPUS Corporation) and with the naked eye and rated on a scale of degrees of coloration. Petals with coloration visible to the naked eye were rated as "III", those with coloration microscopically recognizable at a magnification of at most 32 times were rated as "II", those with coloration microscopically recognizable at a magnification of at least 32 times were rated as "I", and those with no recognizable coloration were rated as "–".

Example 7

Identification of Genes Required to Change the Flower Color of a White Moth Orchid to Red Petals of a white moth orchid (*Phal. amabilis*) were transfected with the following four gene sets by the method in Example 1, and the degrees of coloration of the petals were observed in accordance with Example 6 to identify the genes required to change the flower color.

(1) *Gerbera* F3'H gene (GerF3'H)+*Gerbera* DFR gene (GerDFR)+*Gerbera* ANS gene (GerANS)

(2) Moth orchid F3H gene (PhF3H1)+*Gerbera* F3'H gene (GerF3'H)+*Gerbera* DFR gene (GerDFR)+*Gerbera* ANS gene (GerANS)

(3) Moth orchid CHI gene (PhCHI1)+moth orchid F3H gene (PhF3H1)+*Gerbera* F3'H gene (GerF3'H)+*Gerbera* DFR gene (GerDFR)+*Gerbera* ANS gene (GerANS)

(4) Moth orchid CHS gene (PhCHS3)+moth orchid CHI gene (PhCHI1)+moth orchid F3H gene (PhF3H1)+*Gerbera* F3'H gene (GerF3'H)+*Gerbera* DFR gene (GerDFR)+*Gerbera* ANS gene (GerANS)

Figure 3:
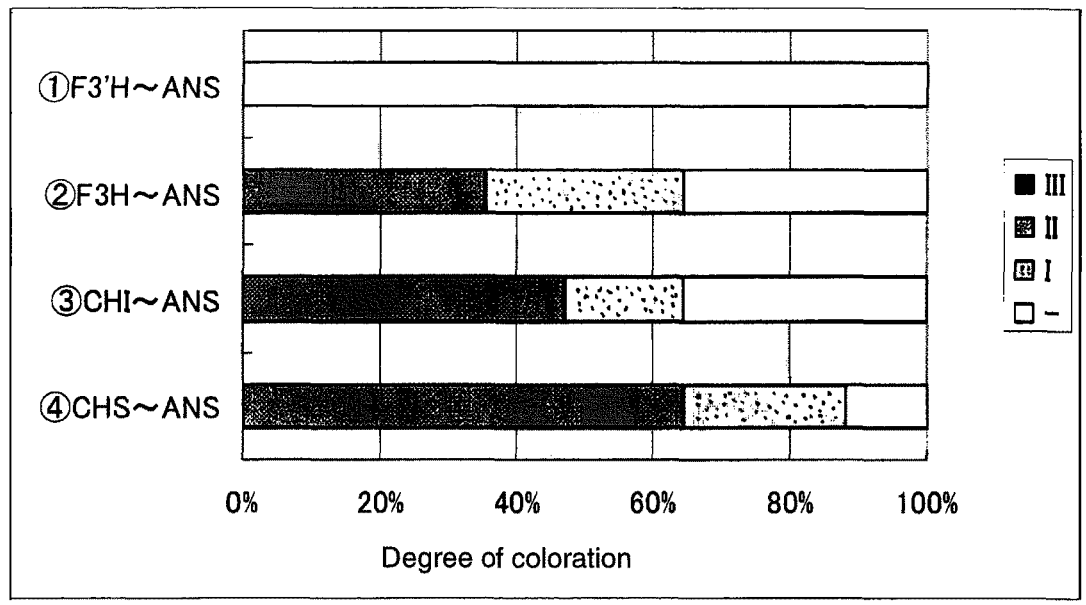
FIG. 3 shows identification of the genes necessary for changing the petal color of a white moth orchid to red.

Petals of *Phal. amabilis* were transfected with the gene sets, and the coloration of cells in the petal treated with the above set were observed. Red cells appeared in the petals transfected with all the gene sets except (1) (FIG. 3). The results indicate that in order to change petals to red, transfection with F3'H gene+DFR gene+ANS gene is insufficient, and transfection with at least four genes including F3H gene in addition to them is necessary.

Study on the Best F3'H Gene, DFR Gene and ANS Gene

In order to find the best F3'H gene, DFR gene and ANS gene for changing white moth orchid to red color, different plant genes were introduced and compared.

Example 8

Comparison of F3'H Genes Introduced in Petals of White Moth Orchid

Petals of a white moth orchid (*Phal. amabilis*) were transfected with the following three sets of genes each including a different F3'H gene, and the degrees of coloration were observed.

(1) Moth orchid F3'H gene (PhF3'H)+moth orchid CHS gene (PhCHS3)+moth orchid CHI gene (PhCHI1)+moth orchid F3H gene (PhF3H1)+*Torenia* DFR gene (TorDFR)+moth orchid ANS gene (PhANS1)

(2) *Gerbera* F3'H gene (GerF3'H)+moth orchid CHS gene (PhCHS3)+moth orchid CHI gene (PhCHI1)+moth orchid F3H gene (PhF3H1)+*Torenia* DFR gene (TorDFR)+moth orchid ANS gene (PhANS1)

(3) *Torenia* F3'H gene (TorF3'H)+moth orchid CHS gene (PhCHS3)+moth orchid CHI gene (PhCHI1)+moth orchid F3H gene (PhF3H1)+*Torenia* DFR gene (TorDFR)+moth orchid ANS gene (PhANS1)

Figure 4:
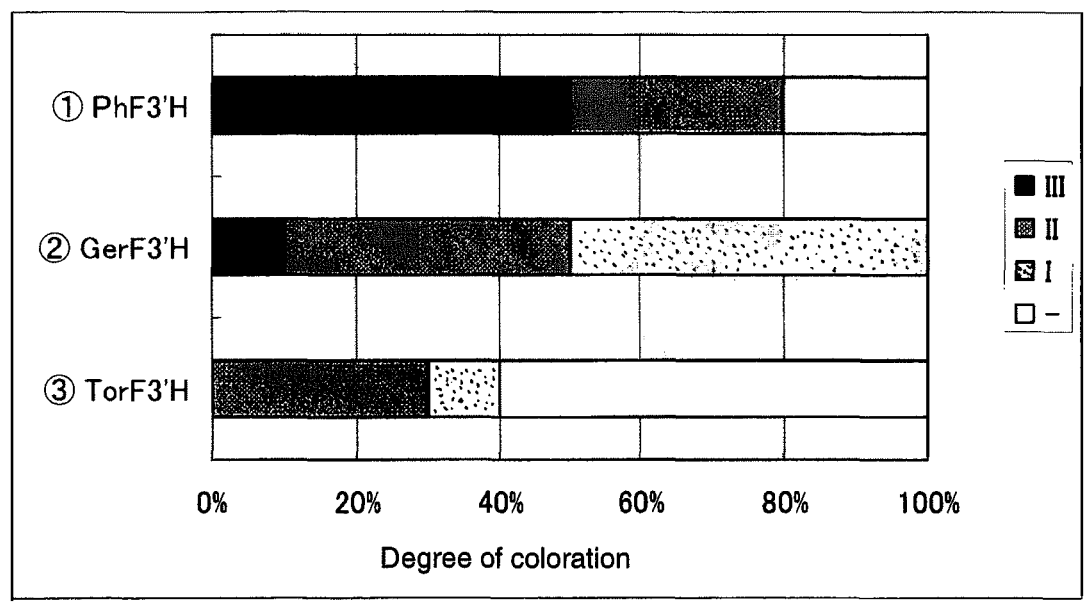
FIG. 4 shows transfection of a petal of *Phal. amabilis* with F3'H genes derived from different plants.

As a result, red cells appeared in petals transfected with each set. The degree of coloration of ten petals transfected with each set is shown in FIG. 4. The degree of red coloration decreased in the order of moth orchid (PhF3'H), *Gerbera* (GerF3'H) and *Torenia*(TorF3'H). For production of a deep red flower, genes from moth orchid (PhF3'H) and *Gerbera* (GerF3'H) are preferred, and especially moth orchid F3'H gene (PhF3'H) is preferred.

Example 9

Comparison of DFR Genes Introduced in Petals of White Moth Orchid

Petals of a white moth orchid (*Phal. amabilis*) were transfected with the following three sets of genes each including a different DFR gene, and the degrees of coloration were observed.

(1) Moth orchid DFR gene (PhDFR)+moth orchid CHS gene (PhCHS3)+moth orchid CHI gene (PhCHI1)+moth orchid F3H gene (PhF3H1)+*Gerbera* F3'H gene (GerF3'H)+*Gerbera* ANS gene (GerANS)

(2) *Gerbera* DFR gene (GerDFR)+moth orchid CHS gene (PhCHS3)+moth orchid CHI gene (PhCHI1)+moth orchid F3H gene (PhF3H1)+*Gerbera* F3'H gene (GerF3'H)+*Gerbera* ANS gene (GerANS)

(3) *Torenia* DFR gene (TorDFR)+moth orchid CHS gene (PhCHS3)+moth orchid CHI gene (PhCHI1)+moth orchid F3H gene (PhF3H1)+*Gerbera* F3'H gene (GerF3'H)+*Gerbera* ANS gene (GerANS)

Figure 5:
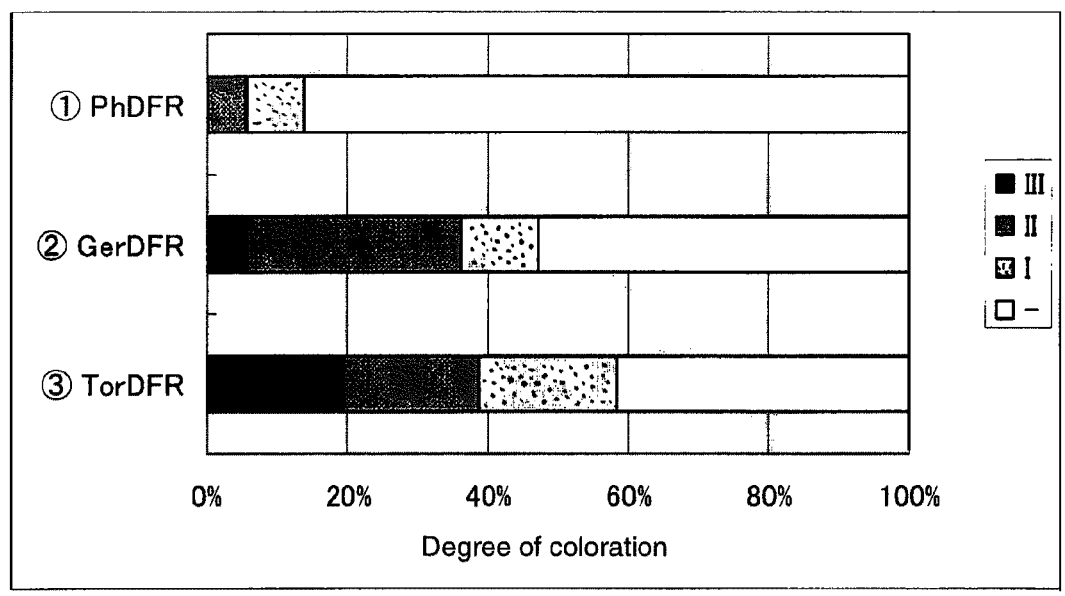
FIG. 5 shows transfection of a petal of *Phal. amabilis* with DFR genes derived from different plants.

As a result, red cells appeared in petals transfected with each set. The degree of coloration of 36 petals transfected with each set is shown in FIG. 5. The degree of red coloration decreased in the order of *Torenia*(TorDFR), *Gerbera* (GerDFR) and moth orchid (PhDFR). For production of a deep red flower, genes from *Torenia*(TorDFR) and *Gerbera* (GerDFR) are preferred to the endogeneous moth orchid DFR gene (PhDFR), and especially, the *Torenia* DFR gene (TorDFR) is preferred.

Example 10

Comparison of ANS Genes Introduced in Petals of White Moth Orchid

Petals of a white moth orchid (*Phal. amabilis*) were transfected with the following two sets of genes each including a different ANS gene, and the degrees of coloration were observed.

(1) Moth orchid ANS gene (PhANS1)+moth orchid CHS gene (PhCHS3)+moth orchid CHI gene (PhCHI1)+moth orchid F3H gene (PhF3H1)+*Gerbera* F3'H gene (GerF3'H)+*Gerbera* DFR gene (GerDFR)

(2) *Gerbera* ANS gene (GerANS)+moth orchid CHS gene (PhCHS3)+moth orchid CHI gene (PhCHI1)+moth orchid F3H gene (PhF3H1)+*Gerbera* F3'H gene (GerF3'H)+*Gerbera* DFR gene (GerDFR)

Figure 6:
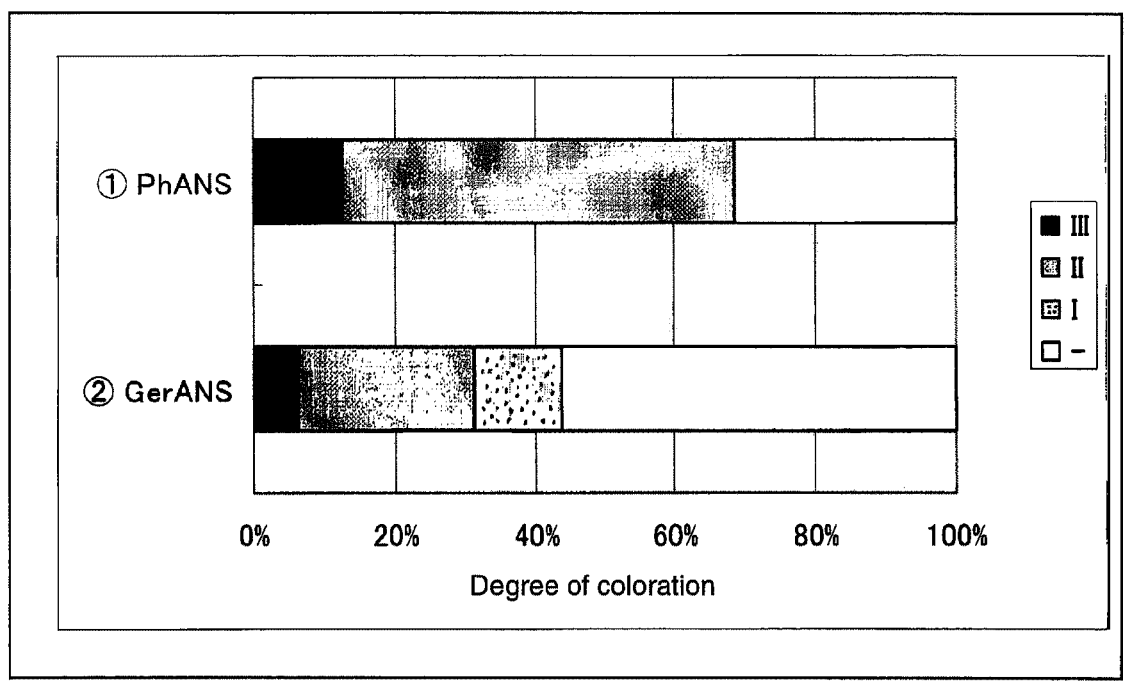
FIG. 6 shows transfection of a petal of *Phal. amabilis* with ANS genes derived from different plants.

As a result, red cells appeared in petals transfected with each set. The degree of coloration of cells in 16 petals transfected with each set is shown in FIG. 6.

Example 11

Application to White Moth Orchid Other than Phal. Amabilis

The petals of a 1.7 cm-long bud of a commercial large pure white moth orchid were cotransfected with the CHS, CHI and F3H genes from a moth orchid (PhCHS3, PhCHI1 and PhF3H1) and the F3'H, DFR and ANS genes from *Gerbera* (GerF3'H, GerDFR and GerANS), and many red cells appeared in the petals.

Example 12

Preparation of DNA for Moth Orchid Transformation by the *Agrobacterium*-Mediated Transformation Transformation of moth orchids can be carried out by *Agrobacterium*-mediated transformation, as well as microprojectile bombardment (Belamino and Mii, Plant Cell Reports (2000) 19:435-442, Mishiba et al., Plant Cell Reports (2005) 24: 297-303). Transforming DNAs for production of transgenic plants by these methods were constructed. Maps of these plasmids and the procedures for their preparation are shown in FIGS. 7 and 8.

(1) Construction of pBI-SAS1

A NotI-HindIII short fragment from pBS-SAS of Example 2 was subcloned between the NotI and HindIII sites of pBI-RHL described on PCT/JP02/12268 to construct pBI-SAS1. pB1-SAS1 is a plasmid which imparts hygromycin resistance to plants by *Agrobacterium*-mediated transformation.

(2) Construction of pBS-35S-FT

Since a period of at least one year is required for blossom of moth orchids, DNA for expressing the flowering gene FT (Kobayashi et al., Science (1999) 286: 1960-1962.) in moth orchids was constructed.

FTcDNA was prepared from total RNA isolated from an *Arabidopsis* whole body by RT-PCR amplification. For the PCR, AtFT 2nd-F (5'-GAAACCACCTGTTTGTTCAAGA-3'; SEQ ID NO: 91) and AtFT 2nd-R (5'-TCAATTGGT-TATAAAGGAAGAAGC-3'; SEQ ID NO: 92) were used as the primers, and FT cDNA was inserted into the SwaI site of pBS-P35T35. The clones carrying the cDNA insert in the sense direction were selected to construct pBS-P35S-FT. In the plasmid pBS-35S-FT, transcription of FT is regulated by the CaMV 35S promoter and the CaMV 35S terminator.

(3) Construction of pBS-35S-mPhF3'H

Nucleotide substitutions were introduced into the two SphI sites of PhF3'H cDNA without amino acid substitution, and the resulting SphI-resistant cDNA was inserted into pBS-P35T35. The nucleotide substitutions were carried out by PCR using PhF3dH-367F (5'-CGGTGCGCGGTGGCGTAT-GCTGAGGCGT-3'; SEQ ID NO: 93) and PhF3dH-394R (5'-ACGCCTCAGCATACGCCACCGCGCACCG-3'; SEQ ID NO: 94) as the primers and pBS-35S-PhF3'H as the template. The PCR product was treated with Klenow fragment and cyclized. PCR was carried out by using the resulting circular DNA as the template and PhF3dH-F11E4 (SEQ ID NO: 57) and PhF3dH-R7G12 (5'-CACCCTTTGCAT-AAATTTATGACATCAAGC-3'; SEQ ID NO: 95) as the primers. The resulting PCR product was inserted into the SwaI cleavage site of pBS-P35T35, and the clones carrying the cDNA insert in the sense direction were selected to construct pBS-35S-mPhF3'H.

(4) Construction of pBS-35S-mPhCHS3

A nucleotide substitution was introduced into the SphI site of PhCHS3 cDNA without amino acid substitution to prepare a SphI-resistant cDNA. The nucleotide substitution was carried out by DNA synthesis using PhCHS3-1038F (5'-GTAA-CATGTCGAGCGCTTGCGTTCTTTTCATACTCG-3'; SEQ ID NO: 96) and PhCHS3-1073R (5'-CGAGTAT-GAAAAGAACGCAAGCGCTCGACATGTTAC-3'; SEQ ID NO: 97) as the primers and p35PhCHS3 as the template and Pyrobest (Takara Bio Inc.). Then, the template plasmid was digested by DpnI treatment to construct pBS-35S-mPh-CHS3.

(5) Construction of pBS-35S-UP1 p35PhCHI1 was cut with AscI, then blunted with Klenow fragment and further cut with SphI to cut out a DNA fragment from the plasmid. The DNA fragment was inserted into the SphI cleavage site of p35PhF3H1 to construct pBS-35S-UP1, after p35PhF3H1 was cut with XbaI and blunted with Klenow fragment. The plasmid pBS-35S-UP1 carries the cDNAs of PhCHI1 and PhF3H1 in this order under the control of the CaMV 35S promoter and the CaMV 35S terminator.

(6) Construction of pBS-35S-Cya1 p35GerANS was cut with AscI, then blunted with Klenow fragment and further cut with SphI to cut out a DNA fragment from the plasmid. The DNA fragment was inserted into the SphI cleavage site of p35GerDFR to construct pBS-35S-Cya1 after p35GerDFR was cut with XbaI and blunted with Klenow fragment. The plasmid pBS-35S-Cya1 carries the cDNAs of GerANS and GerDFR in this order under the control of the CaMV 35S promoter and the CaMV 35S terminator.

(7) Construction of pBS-35S-Cya2 p35GerF3'H was cut with AscI, then blunted with Klenow fragment and further cut with SphI to cut out a DNA fragment from the plasmid. The DNA fragment was inserted into the SphI cleavage site of pBS-35S-Cya1 to construct pBS-35S-Cya2 after pBS-35S-Cya1 was cut with XbaI and blunted with Klenow fragment. The plasmid pBS-35S-Cya2 carries the cDNAs of GerF3'H, GerANS and GerDFR in this order under the control of the CaMV 35S promoter and the CaMV 35S terminator.

(8) Construction of pBS-35S-Cya3 pBS-35S-Cya2 was cut with AscI, then blunted with Klenow fragment and further cut with SphI to cut out a DNA fragment from the plasmid. The DNA fragment was inserted into the SphI cleavage site of pBS-35S-UP1 to construct pBS-35S-Cya3 after pBS-35S-UP1 was cut with XbaI and blunted with Klenow fragment. The plasmid pBS-35S-Cya3 carries the cDNAs of GerF3'H, GerANS, GerDFR, PhCHI and PhF3H in this order under the control of the CaMV 35S promoter and the CaMV 35S terminator.

(9) Construction of pBS-35S-Cya4 pBS-35S-Cya3 was cut with AscI, then blunted with Klenow fragment and further cut with SphI to cut out a DNA fragment from the plasmid. The DNA fragment was inserted into the SphI cleavage site of pBS-35S-mPhCHS3 to construct pBS-35S-Cya4 after pBS-35S-mPhCHS3 was cut with XbaI and blunted with Klenow fragment. The plasmid pBS-35S-Cya4 carries the cDNAs of GerF3'H, GerANS, GerDFR, PhCHI, PhF3H and mPhCHS3 in this order under the control of the CaMV 35S promoter and the CaMV 35S terminator.

(10) Construction of pBS-35S-Cya10 pBS-35S-mPhF3'H was cut with AscI, then blunted with Klenow fragment and further cut with SphI to cut out a DNA fragment from the plasmid. The DNA fragment was inserted into the SphI cleavage site of pBS-35S-FT to construct pBS-35S-Cya10 after pBS-35S-FT was cut with XbaI and blunted with Klenow fragment. The plasmid pBS-35S-Cya10 carries the cDNAs of mPhF3'H and FT in this order under the control of the CaMV 35S promoter and the CaMV 35S terminator.

(11) Construction of pBS-35S-Del16 p35 TorDFR was cut with AscI, then blunted with Klenow fragment and further cut with SphI to cut out a DNA fragment from the plasmid. The DNA fragment was inserted into the SphI cleavage site of p35PhANS1 to construct pBS-35S-Del16 after p35PhANS1 was cut with XbaI and blunted with Klenow fragment. The plasmid pBS-35S-Del16 carries the cDNAs of TorDFR and PhANS1 in this order under the control of the CaMV 35S promoter and the CaMV 35S terminator.

(12) Construction of pBS-35S-UP4 pBS-35S-Dell6 was cut with AscI, then blunted with Klenow fragment and further cut with SphI to cut out a DNA fragment from the plasmid. The DNA fragment was inserted into the SphI cleavage site of pBS-35S-UP1 to construct pBS-35S-UP4 after pBS-35S-UP1 was cut with XbaI and blunted with Klenow fragment. The plasmid pBS-35S-UP4 carries the cDNAs of TorDFR, PhANS1, PhCHI1 and PhF3H1 in this order under the control of the CaMV 35S promoter and the CaMV 35S terminator.

(13) Construction of pBS-35S-Cya11 pBS-35S-mPhF3'H was cut with AscI, then blunted with Klenow fragment and further cut with SphI to cut out a DNA fragment from the plasmid. The DNA fragment was inserted into the SphI cleavage site of pBS-35S-UP4 to construct pBS-35S-Cya11 after pBS-35S-UP4 was cut with XbaI and blunted with Klenow fragment. The plasmid pBS-35S-Cya11 carries the cDNAs of mPhF3'H, TorDFR, PhANS, PhCHI and PhF3H in this order under the control of the CaMV 35S promoter and the CaMV 35S terminator.

(14) Construction of pBS-35S-Cya12 pBS-35S-Cya10 was cut with AscI, then blunted with Klenow fragment and further cut with SphI to cut out a DNA fragment from the plasmid. The DNA fragment was inserted into the SphI cleavage site of pBS-35S-UP4 to construct pBS-35S-Cya12 after pBS-35S-UP4 was cut with XbaI and blunted with Klenow fragment. The plasmid pBS-35S-Cya12 carries the cDNAs of mPhF3'H, FT, TorDFR, PhANS, PhCHI and PhF3H in this order under the control of the CaMV 35S promoter and the CaMV 35S terminator.

(15) Construction of pBIH-35S-Cya3 pBS-35S-Cya3 was cut with SphI, then blunted with Klenow fragment and further cut with AscI to cut out a DNA fragment from the plasmid. The DNA fragment was inserted between the AscI and SwaI cleavage sites of pBI-SAS1 to construct pBIH-35S-Cya3. pBIH-35S-Cya3 is a binary vector with a T-DNA region carrying a selectable marker HPT and the cDNAs of GerF3'H, GerANS, GerDFR, PhCHI and PhF3H in this order under the control of the CaMV 35S promoter and the CaMV 35S terminator.

(16) Construction of pBIH-35S-Cya4 pBS-35S-Cya4 was cut with SphI, then blunted with Klenow fragment and further cut with AscI to cut out a DNA fragment from the plasmid. The DNA fragment was inserted between the AscI and SwaI cleavage sites of pBI-SAS1 to construct pBIH-35S-Cya4. pBIH-35S-Cya4 is a binary vector with a T-DNA region carrying a selectable marker HPT and the cDNAs of GerF3'H, GerANS, GerDFR, PhCHI, PhF3H and mPhCHS3 in this order under the control of the CaMV 35S promoter and the CaMV 35S terminator.

(17) Construction of pBIH-35S-Cya11 pBS-35S-Cya11 was cut with SphI, then blunted with Klenow fragment and further cut with AscI to cut out a DNA fragment from the plasmid. The DNA fragment was inserted between the AscI and SwaI cleavage sites of pBI-SAS1 to construct pBIH-35S-Cya11. pBIH-35S-Cya11 is a binary vector with a T-DNA region carrying a selectable marker HPT and the cDNAs of mPhF3'H, TorDFR, PhANS, PhCHI and PhF3H in this order under the control of the CaMV 35S promoter and the CaMV 35S terminator.

(18) Construction of pBIH-35S-Cya12 pBS-35S-Cya12 was cut with SphI, then blunted with Klenow fragment and further cut with AscI to cut out a DNA fragment from the plasmid. The DNA fragment was inserted between the AscI and SwaI cleavage sites of pBI-SAS1 to construct pBIH-35S-Cya12. pBIH-35S-Cya12 is a binary vector with a T-DNA region carrying a selectable marker HPT and the cDNAs of mPhF3'H, FT, TorDFR, PhANS, PhCHI and PhF3H in this order under the control of the CaMV 35S promoter and the CaMV 35S terminator.

Example 13

Production of Transformed Moth Orchid

A moth orchid was transfected with the binary vector DNAs constructed in Example 12 (pBIH-35S-Cya3, pBIH-35S-Cya4, pBIH-35S-Cya11 and pBIH-35S-Cya12) and *Agrobacterium* EHA101 strain, and transgenic moth orchids were selected in the presence of 50 mg/ml hygromycin to obtain moth orchids having the genes recited in Example 12 integrated into the chromosomes.

The resulting transgenic moth orchids can clonally propagate through induction of PLBs from a part of the plant such as axillary buds of flower stalks. The transgenic moth orchids can be used as a parent in cross breeding to obtain a progeny having the introduced genes.

Thus, it is possible to produce a new variety with a red petal color from a white moth orchid by cotransfection with F3H, F3'H, DFR and ANS genes.

INDUSTRIAL APPLICABILITY

The present invention makes it possible to produce a new variety of moth orchid having a pink or red flower color from a white moth orchid by changing the flower color while maintaining the superiorities of other characters than flower color and is industrially applicable to a wide variety of use.

The entire disclosure of Japanese Patent Application No. 2007-116396 filed on Apr. 26, 2007 including specification, claims, drawings and summary is incorporated herein by reference in its entirety.

Sequence Listing Free Text

SEQ ID NO: 1, Nucleotide sequence encoding *Doritaenopsis* hybrid cultivar flavonoid 3'-hydroxylase
SEQ ID NO: 2, Amino acid sequence of *Doritaenopsis* hybrid cultivar flavonoid 3'-hydroxylase
SEQ ID NO: 3, Nucleotide sequence encoding *Gerbera* hybrid cultivar flavonoid 3'-hydroxylase
SEQ ID NO: 4, Amino acid sequence of *Gerbera* hybrid cultivar flavonoid 3'-hydroxylase
SEQ ID NO: 5, Nucleotide sequence encoding *Torenia fournieri* dihydroflavonol 4-reductase
SEQ ID NO: 6, Amino acid sequence of *Torenia fournieri* dihydroflavonol 4-reductase
SEQ ID NO: 7, Nucleotide sequence encoding *Gerbera* hybrid cultivar dihydroflavonol 4-reductase
SEQ ID NO: 8, Amino acid sequence of *Gerbera* hybrid cultivar dihydroflavonol 4-reductase
SEQ ID NO: 9, Nucleotide sequence encoding *Doritaenopsis* hybrid cultivar flavanone 3-hydroxylase
SEQ ID NO: 10, Amino acid sequence of *Doritaenopsis* hybrid cultivar flavanone 3-hydroxylase
SEQ ID NO: 11, Nucleotide sequence encoding *Doritaenopsis* hybrid cultivar anthocyanidin synthase
SEQ ID NO: 12, Amino acid sequence of *Doritaenopsis* hybrid cultivar anthocyanidin synthase
SEQ ID NO: 13, Nucleotide sequence encoding *Gerbera* hybrid cultivar anthocyanidin synthase
SEQ ID NO: 14, Amino acid sequence of *Gerbera* hybrid cultivar anthocyanidin synthase
SEQ ID NO: 15, Nucleotide sequence encoding *Doritaenopsis* hybrid cultivar dihydroflavonol 4-reductase
SEQ ID NO: 16, Amino acid sequence of *Doritaenopsis* hybrid cultivar dihydroflavonol 4-reductase
SEQ ID NO: 17, Oligonucleotide SAS-S
SEQ ID NO: 18, Oligonucleotide SAS-AS
SEQ ID NO: 19, Primer T-CaMV35S-SseI-F
SEQ ID NO: 20, Primer T-CaMV35S-AscI-R
SEQ ID NO: 21, Primer PhCHS3 F1
SEQ ID NO: 22, Primer PhCHS3 R1
SEQ ID NO: 23, Nucleotide sequence encoding *Doritaenopsis* hybrid cultivar chalcone synthase SEQ ID NO: 24, Amino acid sequence of *Doritaenopsis* hybrid cultivar chalcone synthase
SEQ ID NO: 25, Primer CHI-dgF1
SEQ ID NO: 26, Primer CHI-dgR1
SEQ ID NO: 27, Primer CHI-dgF3
SEQ ID NO: 28, Primer CHI-dgR3
SEQ ID NO: 29, Primer PhCHI-GSP F1
SEQ ID NO: 30, Primer PhCHI-GSP F2
SEQ ID NO: 31, Primer PhCHI-GSP R1
SEQ ID NO: 32, Primer PhCHI-GSP R2
SEQ ID NO: 33, Primer PhCHI init
SEQ ID NO: 34, Primer PhCHI term
SEQ ID NO: 35, Nucleotide sequence encoding *Doritaenopsis* hybrid cultivar chalcone isomerase
SEQ ID NO: 36, Amino acid sequence of *Doritaenopsis* hybrid cultivar chalcone isomerase
SEQ ID NO: 37, Primer F3H-dgF1
SEQ ID NO: 38, Primer F3H-dgR1
SEQ ID NO: 39, Primer F3H-dgF3
SEQ ID NO: 40, Primer F3H-dgR3
SEQ ID NO: 41, Primer PhF3H-GSPF1
SEQ ID NO: 42, Primer PhF3H-GSPF2
SEQ ID NO: 43, Primer PhF3H-GSPR1
SEQ ID NO: 44, Primer PhF3H-GSPR2
SEQ ID NO: 45, Primer PhF3H init.
SEQ ID NO: 46, Primer PhF3H term.
SEQ ID NO: 47, Primer F3HDF3
SEQ ID NO: 48, Primer F3HD-R4-2
SEQ ID NO: 49, Primer F3HDF4
SEQ ID NO: 50, Primer F3HD-R3-2
SEQ ID NO: 51, Primer F3HDF5
SEQ ID NO: 52, Primer F3HD-R1-3
SEQ ID NO: 53, Primer PhF3dH-F7
SEQ ID NO: 54, Primer PhF3dH-F8
SEQ ID NO: 55, Primer PhF3dH-R6
SEQ ID NO: 56, Primer PhF3dH-R5
SEQ ID NO: 57, Primer PhF3dH-F11E4
SEQ ID NO: 58, Primer PhF3dH-R7G11
SEQ ID NO: 59, Primer DFRD-F1
SEQ ID NO: 60, Primer DFRD-R1
SEQ ID NO: 61, Primer DFRD-F2
SEQ ID NO: 62, Primer DFRD-R2
SEQ ID NO: 63, Primer DFRD-F3
SEQ ID NO: 64, Primer DFRD-R3
SEQ ID NO: 65, Primer PhDFR-F1
SEQ ID NO: 66, Primer PhDFR-F2
SEQ ID NO: 67, Primer PhDFR-R4
SEQ ID NO: 68, Primer PhDFR-R3
SEQ ID NO: 69, Primer PhDFR-F8A5
SEQ ID NO: 70, Primer PhDFR-R5
SEQ ID NO: 71, Primer ANS-dgF2
SEQ ID NO: 72, Primer ANS-dgR2
SEQ ID NO: 73, Primer PhANS3RACEGSP1
SEQ ID NO: 74, Primer PhANS3RACEGSP2
SEQ ID NO: 75, Primer PhANS5RACEGSP1
SEQ ID NO: 76, Primer PhANS5RACEGSP2
SEQ ID NO: 77, Primer PhANS init
SEQ ID NO: 78, Primer PhANS term
SEQ ID NO: 79, Primer GerF3H-F
SEQ ID NO: 80, Primer GerF3H-R
SEQ ID NO: 81, Primer GerDFR-F
SEQ ID NO: 82, Primer GerDFR-R
SEQ ID NO: 83, Primer GerANS-F
SEQ ID NO: 84, Primer GerANS-R
SEQ ID NO: 85, Primer TorF3H1-F
SEQ ID NO: 86, Primer TorF3H1-R
SEQ ID NO: 87, Nucleotide sequence encoding *Torenia fournieri* flavonoid 3α-hydroxylase
SEQ ID NO: 88, Amino acid sequence of *Torenia fournieri* flavonoid 3'-hydroxylase
SEQ ID NO: 89, Primer TorDFR-F
SEQ ID NO: 90, Primer TorDFR-R
SEQ ID NO: 91, Primer AtFT 2nd-F
SEQ ID NO: 92, Primer AtFT 2nd-R
SEQ ID NO: 93, Primer PhF3dH-367F
SEQ ID NO: 94, Primer PhF3dH-394R
SEQ ID NO: 95, Primer PhF3dH-R7G12
SEQ ID NO: 96, Primer PhCHS3-1038F
SEQ ID NO: 97, Primer PhCHS3-1073R

---

The invention claimed is:

1. A method for producing a red moth orchid, which comprises transfecting a white moth orchid with a gene encoding a flavanone 3-hydroxylase comprising SEQ ID NO:10, a gene encoding a flavonoid 3'-hydroxylase, a gene encoding a dihydroflavonol 4-reductase and a gene encoding an anthocyanidin synthase; and expressing the genes.

2. The method according to claim 1, wherein the gene encoding a flavonoid 3'-hydroxylase is from a moth orchid or *Gerbera*.

3. The method according to claim 1, wherein the gene encoding a flavonoid 3'-hydroxylase encodes the polypeptide sequence represented by SEQ ID NO: 2 or 4.

4. The method according to claim 1, wherein the gene encoding a dihydroflavonol 4-reductase is from *Gerbera* or *Torenia*.

5. The method according to claim 1, wherein the gene encoding a flavanone 3-hydroxylase has the DNA sequence represented by SEQ ID NO: 9.

6. The method according to claim 1, wherein the gene encoding an anthocyanidin synthase encodes the polypeptide sequence represented by SEQ ID NO: 12 or 14.

7. The method according to claim 1, wherein the gene encoding a flavonoid 3'-hydroxylase is from a moth orchid or *Gerbera*, and the gene encoding a dihydroflavonol 4-reductase is from *Gerbera* or *Torenia*.

8. The method according to claim 1, wherein the gene encoding a flavonoid 3'-hydroxylase encodes the polypeptide sequence represented by SEQ ID NO: 2 or 4, and the gene encoding a dihydroflavonol 4-reductase encodes the polypeptide sequence represented by SEQ ID NO: 6.

9. The method according to claim 1, wherein the gene encoding a flavanone 3-hydroxylase has the DNA sequence represented by SEQ ID NO: 9, and the gene encoding an anthocyanidin synthase encodes the polypeptide sequence represented by SEQ ID NO: 12 or 14.

10. The method according to claim 1, wherein the gene encoding a flavonoid 3'-hydroxylase encodes the polypeptide sequence represented by SEQ ID NO: 2 or 4, and the gene encoding an anthocyanidin synthase encodes the polypeptide sequence represented by SEQ ID NO: 12 or 14.

11. The method according to claim 1, wherein the gene encoding a flavonoid 3'-hydroxylase encodes the polypeptide sequence represented by SEQ ID NO: 2, the gene encoding a dihydroflavonol 4-reductase encodes the polypeptide sequence represented by SEQ ID NO: 6, and the gene encoding an anthocyanidin synthase encodes the polypeptide sequence represented by SEQ ID NO: 12 or 14.

12. A moth orchid or tissue thereof having a modified flower color, which is produced by the method as defined in claim 1.

13. The method according to claim 1, wherein the gene encoding a dihydroflavonol 4-reductase has the DNA sequence represented by SEQ ID NO: 5 or 7.

* * * * *

SEQUENCE LISTING

```
<160> NUMBER OF SEQ ID NOS: 97

<210> SEQ ID NO 1
<211> LENGTH: 1557
<212> TYPE: DNA
<213> ORGANISM: Doritaenopsis hybrid cultivar
<220> FEATURE:
<223> OTHER INFORMATION: Doritaenopsis Queen Beer
<220> FEATURE:
<221> NAME/KEY: CDS
<222> LOCATION: (1)..(1554)
<223> OTHER INFORMATION: Doritaenopsis hybrid cultivar flavonoid
      3'-hydroxylase

<400> SEQUENCE: 1 atg gca tgc tta acc tac ctg ctc ctc tcc acc act ttc ctc ctc ctc    48
Met Ala Cys Leu Thr Tyr Leu Leu Leu Ser Thr Thr Phe Leu Leu Leu
1               5                   10                  15 ctc act ctg ctc ctt ttc tcc ggc gat cgc cgg agc cga ccc cgc cgc    96
Leu Thr Leu Leu Leu Phe Ser Gly Asp Arg Arg Ser Arg Pro Arg Arg
                20                  25                  30 ttc ccg ccg gga ccc aaa ggc tgg ccg atc atc ggt aat ctt ccg caa   144
Phe Pro Pro Gly Pro Lys Gly Trp Pro Ile Ile Gly Asn Leu Pro Gln
            35                  40                  45
```

| | | |
|---|---|---|
| ctc ggc ctc aaa ccc cac caa acc cta acc gat ctt tcg aaa acg tac<br>Leu Gly Leu Lys Pro His Gln Thr Leu Thr Asp Leu Ser Lys Thr Tyr<br>50                      55                      60 | | 192 |
| ggc ccg atc atc ggc ctc cgt ttc ggc tcc gtc gcc gtc gtc gcc gtc<br>Gly Pro Ile Ile Gly Leu Arg Phe Gly Ser Val Ala Val Val Ala Val<br>65                      70                      75                      80 | | 240 |
| tcc tcc gcc gcc gcc gcc gcc caa ttt ctc cga tct cac gac gct aat<br>Ser Ser Ala Ala Ala Ala Ala Gln Phe Leu Arg Ser His Asp Ala Asn<br>                     85                      90                      95 | | 288 |
| ttc agc agc cgg ccg ccc aac tcc ggc gca gag cac atc gca tac aac<br>Phe Ser Ser Arg Pro Pro Asn Ser Gly Ala Glu His Ile Ala Tyr Asn<br>                     100                   105                   110 | | 336 |
| tac cag gat ctg gcg ttc gcg ccc tac ggt gcg cgg tgg cgc atg ctg<br>Tyr Gln Asp Leu Ala Phe Ala Pro Tyr Gly Ala Arg Trp Arg Met Leu<br>                     115                   120                   125 | | 384 |
| agg cgt cta tgc gcc gtg cat ctg ttt tcg ggt aaa gta atg gag gat<br>Arg Arg Leu Cys Ala Val His Leu Phe Ser Gly Lys Val Met Glu Asp<br>         130                   135                   140 | | 432 |
| ttt cgg cac gtg cgg gga ggg gag gtg gag aga ctc gtg cgg ggg atg<br>Phe Arg His Val Arg Gly Gly Glu Val Glu Arg Leu Val Arg Gly Met<br>145                      150                   155                 160 | | 480 |
| gcg gag aag ggg gga ggc gcg gtg gat gtg ggg gcg gcg gtg aac gcg<br>Ala Glu Lys Gly Gly Gly Ala Val Asp Val Gly Ala Ala Val Asn Ala<br>                     165                   170                   175 | | 528 |
| tgt gcg act gat gcg ctg aca cgt gtg gtg gtg ggg agg cgt gtg ttt<br>Cys Ala Thr Asp Ala Leu Thr Arg Val Val Val Gly Arg Arg Val Phe<br>                     180                   185                   190 | | 576 |
| ggt gat ggg aag gag gag aag gaa ggc gcg gag gag ttt aag gag atg<br>Gly Asp Gly Lys Glu Glu Lys Glu Gly Ala Glu Glu Phe Lys Glu Met<br>                     195                   200                   205 | | 624 |
| gtg gtg gag ctt atg cag ctc gcc ggc gtt ttc aat att ggg gat ttt<br>Val Val Glu Leu Met Gln Leu Ala Gly Val Phe Asn Ile Gly Asp Phe<br>     210                      215                   220 | | 672 |
| gtg ccc tgt ttg gcc tgg ctt gat tta cag ggg gtg gtg agg aag atg<br>Val Pro Cys Leu Ala Trp Leu Asp Leu Gln Gly Val Val Arg Lys Met<br>225                      230                   235                 240 | | 720 |
| aag aag ctt cat gga aga ttt gat aaa ttt ttc gat gga ata att gca<br>Lys Lys Leu His Gly Arg Phe Asp Lys Phe Phe Asp Gly Ile Ile Ala<br>                     245                   250                   255 | | 768 |
| gag cac aga gag gca ata gag aag ggc gaa gtt aat ggt gga ggc agt<br>Glu His Arg Glu Ala Ile Glu Lys Gly Glu Val Asn Gly Gly Gly Ser<br>                     260                   265                   270 | | 816 |
| gat atg ctg agc ata ctc atc agg atg aaa gaa gaa ggt gat ggg gaa<br>Asp Met Leu Ser Ile Leu Ile Arg Met Lys Glu Glu Gly Asp Gly Glu<br>                   275                   280                   285 | | 864 |
| gag ttc aag ctt acc gat aca gaa atc aag gct ctc cta ctg aat cta<br>Glu Phe Lys Leu Thr Asp Thr Glu Ile Lys Ala Leu Leu Leu Asn Leu<br>                     290                   295                   300 | | 912 |
| ttc gca gca ggg acg gac acc aca tca agc aca gta gaa tgg gcc tta<br>Phe Ala Ala Gly Thr Asp Thr Thr Ser Ser Thr Val Glu Trp Ala Leu<br>305                      310                   315                 320 | | 960 |
| gcc gag cta ata aga cac cca aag atc cta aaa cga gcc caa aac gag<br>Ala Glu Leu Ile Arg His Pro Lys Ile Leu Lys Arg Ala Gln Asn Glu<br>                     325                   330                   335 | | 1008 |
| ctt gac tcg gtc atc gga ctc aac cga ctc gcc acc gag tcg gac ctc<br>Leu Asp Ser Val Ile Gly Leu Asn Arg Leu Ala Thr Glu Ser Asp Leu<br>                     340                   345                   350 | | 1056 |
| ccc cac ctc ccc tat ctc caa tcc att gtc aaa gaa acc ttc cgt ctc<br>Pro His Leu Pro Tyr Leu Gln Ser Ile Val Lys Glu Thr Phe Arg Leu<br>                     355                   360                   365 | | 1104 |

```
cat ccc tca acc cct ctc tct ctt cca cgt gtc gct tcc aac gac tgc    1152
His Pro Ser Thr Pro Leu Ser Leu Pro Arg Val Ala Ser Asn Asp Cys
    370             375                 380 cag atc gat aac tac ctc att ccg aag ggc tcc act ctt ctc gtc aat    1200
Gln Ile Asp Asn Tyr Leu Ile Pro Lys Gly Ser Thr Leu Leu Val Asn
385                 390                 395                 400 att tgg gcc att gga cgg gag gaa tca acg tgg gca gat ggg ccg ttg    1248
Ile Trp Ala Ile Gly Arg Glu Glu Ser Thr Trp Ala Asp Gly Pro Leu
                405                 410                 415 gag ttc aag ccc gag agg ttt ctc ccc ggc ggg ctt cat gag gga gtt    1296
Glu Phe Lys Pro Glu Arg Phe Leu Pro Gly Gly Leu His Glu Gly Val
            420                 425                 430 gat gtt aag ggg aat gat ttt ggg ctc ata ccg ttt ggg gct ggg cgg    1344
Asp Val Lys Gly Asn Asp Phe Gly Leu Ile Pro Phe Gly Ala Gly Arg
        435                 440                 445 agg att tgt gtg ggc ttg agt ttg ggg ctg aga atg gtg cag ttc atg    1392
Arg Ile Cys Val Gly Leu Ser Leu Gly Leu Arg Met Val Gln Phe Met
    450                 455                 460 acg gcg act ttg gtt cat gct ttt gat tgg gat ttg gtt gat ggg ctg    1440
Thr Ala Thr Leu Val His Ala Phe Asp Trp Asp Leu Val Asp Gly Leu
465                 470                 475                 480 agt ggg gag aag ctg gat atg gaa gag gct tat ggg ctc act ctt cgt    1488
Ser Gly Glu Lys Leu Asp Met Glu Glu Ala Tyr Gly Leu Thr Leu Arg
                485                 490                 495 cgg gcc gtg ccg ctt gtg gct agg ccc acg aca agg ttg gcc cta agc    1536
Arg Ala Val Pro Leu Val Ala Arg Pro Thr Thr Arg Leu Ala Leu Ser
            500                 505                 510 gct tat cat aat gat gct tag                                        1557
Ala Tyr His Asn Asp Ala
        515

<210> SEQ ID NO 2
<211> LENGTH: 518
<212> TYPE: PRT
<213> ORGANISM: Doritaenopsis hybrid cultivar
<220> FEATURE:
<223> OTHER INFORMATION: Doritaenopsis Queen Beer

<400> SEQUENCE: 2

Met Ala Cys Leu Thr Tyr Leu Leu Leu Ser Thr Thr Phe Leu Leu Leu
1               5                   10                  15

Leu Thr Leu Leu Leu Phe Ser Gly Asp Arg Arg Ser Arg Pro Arg Arg
                20                  25                  30

Phe Pro Pro Gly Pro Lys Gly Trp Pro Ile Ile Gly Asn Leu Pro Gln
            35                  40                  45

Leu Gly Leu Lys Pro His Gln Thr Leu Thr Asp Leu Ser Lys Thr Tyr
        50                  55                  60

Gly Pro Ile Ile Gly Leu Arg Phe Gly Ser Val Ala Val Val Ala Val
65                  70                  75                  80

Ser Ser Ala Ala Ala Ala Gln Phe Leu Arg Ser His Asp Ala Asn
                85                  90                  95

Phe Ser Ser Arg Pro Pro Asn Ser Gly Ala Glu His Ile Ala Tyr Asn
            100                 105                 110

Tyr Gln Asp Leu Ala Phe Ala Pro Tyr Gly Ala Arg Trp Arg Met Leu
        115                 120                 125

Arg Arg Leu Cys Ala Val His Leu Phe Ser Gly Lys Val Met Glu Asp
    130                 135                 140

Phe Arg His Val Arg Gly Gly Glu Val Glu Arg Leu Val Arg Gly Met
145                 150                 155                 160
```

```
Ala Glu Lys Gly Gly Gly Ala Val Asp Val Gly Ala Ala Val Asn Ala
            165                 170                 175
Cys Ala Thr Asp Ala Leu Thr Arg Val Val Gly Arg Arg Val Phe
        180                 185                 190
Gly Asp Gly Lys Glu Glu Lys Glu Gly Ala Glu Glu Phe Lys Glu Met
            195                 200                 205
Val Val Glu Leu Met Gln Leu Ala Gly Val Phe Asn Ile Gly Asp Phe
        210                 215                 220
Val Pro Cys Leu Ala Trp Leu Asp Leu Gln Gly Val Val Arg Lys Met
225                 230                 235                 240
Lys Lys Leu His Gly Arg Phe Asp Lys Phe Asp Gly Ile Ile Ala
            245                 250                 255
Glu His Arg Glu Ala Ile Glu Lys Gly Glu Val Asn Gly Gly Ser
            260                 265                 270
Asp Met Leu Ser Ile Leu Ile Arg Met Lys Glu Glu Gly Asp Gly Glu
            275                 280                 285
Glu Phe Lys Leu Thr Asp Thr Glu Ile Lys Ala Leu Leu Leu Asn Leu
        290                 295                 300
Phe Ala Ala Gly Thr Asp Thr Thr Ser Ser Thr Val Glu Trp Ala Leu
305                 310                 315                 320
Ala Glu Leu Ile Arg His Pro Lys Ile Leu Lys Arg Ala Gln Asn Glu
                325                 330                 335
Leu Asp Ser Val Ile Gly Leu Asn Arg Leu Ala Thr Glu Ser Asp Leu
            340                 345                 350
Pro His Leu Pro Tyr Leu Gln Ser Ile Val Lys Glu Thr Phe Arg Leu
            355                 360                 365
His Pro Ser Thr Pro Leu Ser Leu Pro Arg Val Ala Ser Asn Asp Cys
370                 375                 380
Gln Ile Asp Asn Tyr Leu Ile Pro Lys Gly Ser Thr Leu Leu Val Asn
385                 390                 395                 400
Ile Trp Ala Ile Gly Arg Glu Glu Ser Thr Trp Ala Asp Gly Pro Leu
                405                 410                 415
Glu Phe Lys Pro Glu Arg Phe Leu Pro Gly Gly Leu His Glu Gly Val
            420                 425                 430
Asp Val Lys Gly Asn Asp Phe Gly Leu Ile Pro Phe Gly Ala Gly Arg
            435                 440                 445
Arg Ile Cys Val Gly Leu Ser Leu Gly Leu Arg Met Val Gln Phe Met
        450                 455                 460
Thr Ala Thr Leu Val His Ala Phe Asp Trp Asp Leu Val Asp Gly Leu
465                 470                 475                 480
Ser Gly Glu Lys Leu Asp Met Glu Glu Ala Tyr Gly Leu Thr Leu Arg
            485                 490                 495
Arg Ala Val Pro Leu Val Ala Arg Pro Thr Thr Arg Leu Ala Leu Ser
            500                 505                 510
Ala Tyr His Asn Asp Ala
        515

<210> SEQ ID NO 3
<211> LENGTH: 1539
<212> TYPE: DNA
<213> ORGANISM: Gerbera hybrid cultivar
<220> FEATURE:
<221> NAME/KEY: CDS
<222> LOCATION: (1)..(1536)
<223> OTHER INFORMATION: Gerbera hybrid cultivar flavonoid
      3'-hydroxylase
```

<400> SEQUENCE: 3

```
atg acg cct tta acg ctc ctt atc ggc acc tgt gtc act gga tta ttc      48
Met Thr Pro Leu Thr Leu Leu Ile Gly Thr Cys Val Thr Gly Leu Phe
1               5                   10                  15 ctc tac gtg ttg ctt aac cgg tgc acc cgt aac cct aac cgc ctc ccg      96
Leu Tyr Val Leu Leu Asn Arg Cys Thr Arg Asn Pro Asn Arg Leu Pro
                20                  25                  30 ccc ggc cca acg cca tgg ccg gtc gtc gga aac cta ccg cat ctc ggc     144
Pro Gly Pro Thr Pro Trp Pro Val Val Gly Asn Leu Pro His Leu Gly
            35                  40                  45 act ata cca cac cac tcg ctg gcg gcg atg gcg aag aag tat ggc ccg     192
Thr Ile Pro His His Ser Leu Ala Ala Met Ala Lys Lys Tyr Gly Pro
        50                  55                  60 ttg atg cac ctc cgg cta ggc ttc gtc gac gtc gtg gtg gcc gcc tcc     240
Leu Met His Leu Arg Leu Gly Phe Val Asp Val Val Val Ala Ala Ser
65                  70                  75                  80 gcc tcc gtc gcg gcg cag ttt ttg aag act cac gac gcg aac ttc gcc     288
Ala Ser Val Ala Ala Gln Phe Leu Lys Thr His Asp Ala Asn Phe Ala
                85                  90                  95 gat cgg ccg ccg aac tcc gga gcc aag cat atc gcg tat aat tat cag     336
Asp Arg Pro Pro Asn Ser Gly Ala Lys His Ile Ala Tyr Asn Tyr Gln
            100                 105                 110 gat ctg gtg ttt gct ccg tac ggt ccg cgg tgg cgg atg ctt cgg aag     384
Asp Leu Val Phe Ala Pro Tyr Gly Pro Arg Trp Arg Met Leu Arg Lys
        115                 120                 125 att tgc tcg gtg cac ctg ttt tcc acc aaa gcg ctc gat gat ttc cgg     432
Ile Cys Ser Val His Leu Phe Ser Thr Lys Ala Leu Asp Asp Phe Arg
130                 135                 140 cac gtc cgg cag gag gag gta gcg ata cta gcg cgc gct ttg gtc ggc     480
His Val Arg Gln Glu Glu Val Ala Ile Leu Ala Arg Ala Leu Val Gly
145                 150                 155                 160 gcc gga aaa tca ccg gtg aaa tta ggt cag tta ctg aac gtg tgc acc     528
Ala Gly Lys Ser Pro Val Lys Leu Gly Gln Leu Leu Asn Val Cys Thr
                165                 170                 175 aca aac gca ttg gcg cga gtg atg tta ggg agg aga gta ttt gac tcc     576
Thr Asn Ala Leu Ala Arg Val Met Leu Gly Arg Arg Val Phe Asp Ser
            180                 185                 190 ggc gat gct cag gcg gat gag ttc aag gac atg gtg gtt gag ctg atg     624
Gly Asp Ala Gln Ala Asp Glu Phe Lys Asp Met Val Val Glu Leu Met
        195                 200                 205 gtg tta gcc gga gaa ttc aac atc ggc gac ttc atc ccc gtg ctt gac     672
Val Leu Ala Gly Glu Phe Asn Ile Gly Asp Phe Ile Pro Val Leu Asp
210                 215                 220 tgg ctg gac ctg caa ggc gtg acg aag aag atg aag aaa ctc cac gcg     720
Trp Leu Asp Leu Gln Gly Val Thr Lys Lys Met Lys Lys Leu His Ala
225                 230                 235                 240 aaa ttc gac tcg ttc ctt aac acg atc ctc gaa gaa cat aaa acc ggc     768
Lys Phe Asp Ser Phe Leu Asn Thr Ile Leu Glu Glu His Lys Thr Gly
                245                 250                 255 gcc ggt gac ggt gtc gcg tcg ggt aaa gtt gac ttg ttg agc acg ttg     816
Ala Gly Asp Gly Val Ala Ser Gly Lys Val Asp Leu Leu Ser Thr Leu
            260                 265                 270 ctt tcc ctg aag gat gac gcc gat gga gag gga ggg aag ctg tcg gac     864
Leu Ser Leu Lys Asp Asp Ala Asp Gly Glu Gly Gly Lys Leu Ser Asp
        275                 280                 285 att gaa atc aaa gct ttg ctt ctg aac tta ttc aca gcg ggg act gac     912
Ile Glu Ile Lys Ala Leu Leu Leu Asn Leu Phe Thr Ala Gly Thr Asp
        290                 295                 300
```

-continued

| | | |
|---|---|---|
| aca tca tct agt act gtt gaa tgg gcc ata gct gaa cta att cgc aac<br>Thr Ser Ser Ser Thr Val Glu Trp Ala Ile Ala Glu Leu Ile Arg Asn<br>305                        310                    315                  320 | 960 |
| ccg caa cta ttg aac caa gcc cga aaa gaa atg gac acc ata gtt ggt<br>Pro Gln Leu Leu Asn Gln Ala Arg Lys Glu Met Asp Thr Ile Val Gly<br>                        325                    330                    335 | 1008 |
| caa gac cga ctt gta acc gag tca gac cta ggt caa cta aca ttc ctc<br>Gln Asp Arg Leu Val Thr Glu Ser Asp Leu Gly Gln Leu Thr Phe Leu<br>                340                    345                    350 | 1056 |
| caa gcc att atc aag gaa act ttt agg ctt cac ccg tca acc cca cta<br>Gln Ala Ile Ile Lys Glu Thr Phe Arg Leu His Pro Ser Thr Pro Leu<br>           355                    360                    365 | 1104 |
| tca ctg cca agg atg gca ttg gag agt tgt gag gtt gac ggt tat tac<br>Ser Leu Pro Arg Met Ala Leu Glu Ser Cys Glu Val Asp Gly Tyr Tyr<br>370                        375                    380 | 1152 |
| atc cct aaa gga tcc act ctc ctt gtt aat gtg tgg gcc att tct cga<br>Ile Pro Lys Gly Ser Thr Leu Leu Val Asn Val Trp Ala Ile Ser Arg<br>385                        390                    395                  400 | 1200 |
| gac cct aaa atg tgg gcc gat cca ctt gaa ttt cag ccc act cga ttc<br>Asp Pro Lys Met Trp Ala Asp Pro Leu Glu Phe Gln Pro Thr Arg Phe<br>                        405                    410                    415 | 1248 |
| tta ccc ggg ggt gaa aag gcc aat act gat atc aaa gga aat gat ttt<br>Leu Pro Gly Gly Glu Lys Ala Asn Thr Asp Ile Lys Gly Asn Asp Phe<br>                420                    425                    430 | 1296 |
| gaa gtc ata ccg ttt ggg gcc gga cga agg att tgt gtc gga atg agc<br>Glu Val Ile Pro Phe Gly Ala Gly Arg Arg Ile Cys Val Gly Met Ser<br>           435                    440                    445 | 1344 |
| cta ggg tta agg atg gtc cag ttg ttg act gca acc cta atc cat gcc<br>Leu Gly Leu Arg Met Val Gln Leu Leu Thr Ala Thr Leu Ile His Ala<br>                450                    455                    460 | 1392 |
| ttt gat tgg gaa ctg gct gat ggg tta aac cca aag aag ctt aac atg<br>Phe Asp Trp Glu Leu Ala Asp Gly Leu Asn Pro Lys Lys Leu Asn Met<br>465                        470                    475                  480 | 1440 |
| gaa gag gct tac ggg ttg acc ctt caa agg gcc gca ccg tta gtg gtt<br>Glu Glu Ala Tyr Gly Leu Thr Leu Gln Arg Ala Ala Pro Leu Val Val<br>                        485                    490                    495 | 1488 |
| cac cca agg cca agg tta gcc cca cat gta tat gag acg act aag gtc<br>His Pro Arg Pro Arg Leu Ala Pro His Val Tyr Glu Thr Thr Lys Val<br>                500                    505                    510 | 1536 |
| tag | 1539 |

<210> SEQ ID NO 4
<211> LENGTH: 512
<212> TYPE: PRT
<213> ORGANISM: Gerbera hybrid cultivar

<400> SEQUENCE: 4

Met Thr Pro Leu Thr Leu Leu Ile Gly Thr Cys Val Thr Gly Leu Phe
1               5                   10                  15

Leu Tyr Val Leu Leu Asn Arg Cys Thr Arg Asn Pro Asn Arg Leu Pro
            20                  25                  30

Pro Gly Pro Thr Pro Trp Pro Val Val Gly Asn Leu Pro His Leu Gly
        35                  40                  45

Thr Ile Pro His His Ser Leu Ala Ala Met Ala Lys Lys Tyr Gly Pro
    50                  55                  60

Leu Met His Leu Arg Leu Gly Phe Val Asp Val Val Ala Ala Ser
65                  70                  75                  80

Ala Ser Val Ala Ala Gln Phe Leu Lys Thr His Asp Ala Asn Phe Ala
                85                  90                  95

-continued

```
Asp Arg Pro Pro Asn Ser Gly Ala Lys His Ile Ala Tyr Asn Tyr Gln
            100                 105                 110
Asp Leu Val Phe Ala Pro Tyr Gly Pro Arg Trp Arg Met Leu Arg Lys
        115                 120                 125
Ile Cys Ser Val His Leu Phe Ser Thr Lys Ala Leu Asp Asp Phe Arg
130                 135                 140
His Val Arg Gln Glu Glu Val Ala Ile Leu Ala Arg Ala Leu Val Gly
145                 150                 155                 160
Ala Gly Lys Ser Pro Val Lys Leu Gly Gln Leu Leu Asn Val Cys Thr
                165                 170                 175
Thr Asn Ala Leu Ala Arg Val Met Leu Gly Arg Arg Val Phe Asp Ser
            180                 185                 190
Gly Asp Ala Gln Ala Asp Glu Phe Lys Asp Met Val Val Glu Leu Met
        195                 200                 205
Val Leu Ala Gly Glu Phe Asn Ile Gly Asp Phe Ile Pro Val Leu Asp
210                 215                 220
Trp Leu Asp Leu Gln Gly Val Thr Lys Met Lys Lys Leu His Ala
225                 230                 235                 240
Lys Phe Asp Ser Phe Leu Asn Thr Ile Leu Glu Glu His Lys Thr Gly
                245                 250                 255
Ala Gly Asp Gly Val Ala Ser Gly Lys Val Asp Leu Leu Ser Thr Leu
            260                 265                 270
Leu Ser Leu Lys Asp Asp Ala Asp Gly Glu Gly Gly Lys Leu Ser Asp
        275                 280                 285
Ile Glu Ile Lys Ala Leu Leu Leu Asn Leu Phe Thr Ala Gly Thr Asp
290                 295                 300
Thr Ser Ser Ser Thr Val Glu Trp Ala Ile Ala Glu Leu Ile Arg Asn
305                 310                 315                 320
Pro Gln Leu Leu Asn Gln Ala Arg Lys Glu Met Asp Thr Ile Val Gly
                325                 330                 335
Gln Asp Arg Leu Val Thr Glu Ser Asp Leu Gly Gln Leu Thr Phe Leu
            340                 345                 350
Gln Ala Ile Ile Lys Glu Thr Phe Arg Leu His Pro Ser Thr Pro Leu
        355                 360                 365
Ser Leu Pro Arg Met Ala Leu Glu Ser Cys Glu Val Asp Gly Tyr Tyr
370                 375                 380
Ile Pro Lys Gly Ser Thr Leu Leu Val Asn Val Trp Ala Ile Ser Arg
385                 390                 395                 400
Asp Pro Lys Met Trp Ala Asp Pro Leu Glu Phe Gln Pro Thr Arg Phe
                405                 410                 415
Leu Pro Gly Gly Glu Lys Ala Asn Thr Asp Ile Lys Gly Asn Asp Phe
            420                 425                 430
Glu Val Ile Pro Phe Gly Ala Gly Arg Arg Ile Cys Val Gly Met Ser
        435                 440                 445
Leu Gly Leu Arg Met Val Gln Leu Leu Thr Ala Thr Leu Ile His Ala
450                 455                 460
Phe Asp Trp Glu Leu Ala Asp Gly Leu Asn Pro Lys Lys Leu Asn Met
465                 470                 475                 480
Glu Glu Ala Tyr Gly Leu Thr Leu Gln Arg Ala Ala Pro Leu Val Val
                485                 490                 495
His Pro Arg Pro Arg Leu Ala Pro His Val Tyr Glu Thr Thr Lys Val
            500                 505                 510
```

<210> SEQ ID NO 5
<211> LENGTH: 1050
<212> TYPE: DNA
<213> ORGANISM: Torenia fournieri
<220> FEATURE:
<221> NAME/KEY: CDS
<222> LOCATION: (1)..(1047)
<223> OTHER INFORMATION: Torenia fournieri dihydroflavonol 4-reductase

<400> SEQUENCE: 5

| | | | | | | | | | | | | | | | | |
|---|---|---|---|---|---|---|---|---|---|---|---|---|---|---|---|---|
| atg | agc | atg | gaa | gta | gta | cca | aaa | gca | cag | ccc | atc | aca | gtg | tgt | | 48 |
| Met | Ser | Met | Glu | Val | Val | Pro | Lys | Ala | Gln | Pro | Ile | Thr | Val | Cys | | |
| 1 | | | | 5 | | | | | 10 | | | | | 15 | | |
| gtc | acc | gga | gcc | agc | ggt | ttc | ata | ggc | tca | tgg | ctt | gta | atg | aaa | cta | 96 |
| Val | Thr | Gly | Ala | Ser | Gly | Phe | Ile | Gly | Ser | Trp | Leu | Val | Met | Lys | Leu | |
| | | | 20 | | | | | 25 | | | | | 30 | | | |
| ctt | caa | cgt | ggt | tat | aca | gtt | cat | gcc | act | gtc | cgt | gat | cct | gag | aat | 144 |
| Leu | Gln | Arg | Gly | Tyr | Thr | Val | His | Ala | Thr | Val | Arg | Asp | Pro | Glu | Asn | |
| | | 35 | | | | | 40 | | | | | 45 | | | | |
| atg | aag | aag | gtg | aaa | cac | tta | ctg | gaa | ttg | cca | aga | gct | gac | gat | gcg | 192 |
| Met | Lys | Lys | Val | Lys | His | Leu | Leu | Glu | Leu | Pro | Arg | Ala | Asp | Asp | Ala | |
| 50 | | | | | 55 | | | | | 60 | | | | | | |
| agc | ctg | aga | ctg | ttc | aaa | gct | gat | atg | aac | gta | gaa | ggt | agc | ttc | gat | 240 |
| Ser | Leu | Arg | Leu | Phe | Lys | Ala | Asp | Met | Asn | Val | Glu | Gly | Ser | Phe | Asp | |
| 65 | | | | 70 | | | | | 75 | | | | | 80 | | |
| gaa | gca | gtt | gga | tcc | tgc | gaa | tgt | gtg | ttt | cac | atg | gca | acg | cct | atg | 288 |
| Glu | Ala | Val | Gly | Ser | Cys | Glu | Cys | Val | Phe | His | Met | Ala | Thr | Pro | Met | |
| | | | | 85 | | | | | 90 | | | | | 95 | | |
| gat | ttc | gaa | tcg | gac | gat | cct | gag | aat | gaa | gtg | att | aag | cca | aca | gta | 336 |
| Asp | Phe | Glu | Ser | Asp | Asp | Pro | Glu | Asn | Glu | Val | Ile | Lys | Pro | Thr | Val | |
| | | | 100 | | | | | 105 | | | | | 110 | | | |
| gat | ggg | atg | ttg | agc | atc | atc | agg | tca | tgt | gca | aag | gcc | caa | aca | gtc | 384 |
| Asp | Gly | Met | Leu | Ser | Ile | Ile | Arg | Ser | Cys | Ala | Lys | Ala | Gln | Thr | Val | |
| | | | 115 | | | | | 120 | | | | | 125 | | | |
| aag | aga | ttg | atc | ttc | acc | aac | tcg | gct | ggg | act | ttg | aat | gtc | gaa | gaa | 432 |
| Lys | Arg | Leu | Ile | Phe | Thr | Asn | Ser | Ala | Gly | Thr | Leu | Asn | Val | Glu | Glu | |
| | 130 | | | | | 135 | | | | | 140 | | | | | |
| cac | cag | aaa | cct | gtg | tat | gat | gag | agc | aat | tgg | agt | gac | ctg | gat | ttt | 480 |
| His | Gln | Lys | Pro | Val | Tyr | Asp | Glu | Ser | Asn | Trp | Ser | Asp | Leu | Asp | Phe | |
| 145 | | | | | 150 | | | | | 155 | | | | | 160 | |
| att | tac | tcc | acg | aaa | atg | acg | gga | tgg | atg | tac | ttt | gta | tct | aag | gtt | 528 |
| Ile | Tyr | Ser | Thr | Lys | Met | Thr | Gly | Trp | Met | Tyr | Phe | Val | Ser | Lys | Val | |
| | | | | 165 | | | | | 170 | | | | | 175 | | |
| ttg | gcc | gag | aaa | gca | gcg | att | aaa | gca | tgt | aag | gag | aat | aac | ata | gat | 576 |
| Leu | Ala | Glu | Lys | Ala | Ala | Ile | Lys | Ala | Cys | Lys | Glu | Asn | Asn | Ile | Asp | |
| | | | 180 | | | | | 185 | | | | | 190 | | | |
| ttc | ata | agc | atc | ata | cct | cca | gta | gtg | gtc | ggt | ccg | ttc | atc | atc | gat | 624 |
| Phe | Ile | Ser | Ile | Ile | Pro | Pro | Val | Val | Val | Gly | Pro | Phe | Ile | Ile | Asp | |
| | | 195 | | | | | 200 | | | | | 205 | | | | |
| aat | tgg | cca | ccg | agc | ctg | atc | aca | gca | ctc | tct | cct | att | acc | ggc | aat | 672 |
| Asn | Trp | Pro | Pro | Ser | Leu | Ile | Thr | Ala | Leu | Ser | Pro | Ile | Thr | Gly | Asn | |
| | 210 | | | | | 215 | | | | | 220 | | | | | |
| gaa | gct | cat | tac | tcc | atc | ata | aag | caa | gga | cag | ttt | gtg | cat | gtt | gat | 720 |
| Glu | Ala | His | Tyr | Ser | Ile | Ile | Lys | Gln | Gly | Gln | Phe | Val | His | Val | Asp | |
| 225 | | | | | 230 | | | | | 235 | | | | | 240 | |
| gat | ctc | tgt | gag | gct | cat | ata | ttc | ttg | tct | gag | cat | ccc | aaa | aca | gaa | 768 |
| Asp | Leu | Cys | Glu | Ala | His | Ile | Phe | Leu | Ser | Glu | His | Pro | Lys | Thr | Glu | |
| | | | | 245 | | | | | 250 | | | | | 255 | | |
| gag | aga | tac | att | tgc | tcc | tct | cat | gac | gca | acc | att | tac | gac | ata | gcg | 816 |
| Glu | Arg | Tyr | Ile | Cys | Ser | Ser | His | Asp | Ala | Thr | Ile | Tyr | Asp | Ile | Ala | |
| | | | 260 | | | | | 265 | | | | | 270 | | | |
| aat | atg | atc | aga | gag | aaa | tgg | cct | gaa | tat | gat | gtc | cca | act | gaa | ttt | 864 |

```
                    Asn Met Ile Arg Glu Lys Trp Pro Glu Tyr Asp Val Pro Thr Glu Phe
                        275                 280                 285 gag gga att gac aag gac ata cct gtg gtg aga ttt tca tcc aag aaa          912
Glu Gly Ile Asp Lys Asp Ile Pro Val Val Arg Phe Ser Ser Lys Lys
    290                 295                 300 ctg atg gga atg gga ttt acc ttc aag tat aca ttg gag gac atg ttc          960
Leu Met Gly Met Gly Phe Thr Phe Lys Tyr Thr Leu Glu Asp Met Phe
305                 310                 315                 320 aga gaa gcc att gag act tgt cga gac aaa ggg ctt ctt cct tat tcg         1008
Arg Glu Ala Ile Glu Thr Cys Arg Asp Lys Gly Leu Leu Pro Tyr Ser
                325                 330                 335 acc act cgc gac cac atc cat gga gaa cat aag ata gaa tag                 1050
Thr Thr Arg Asp His Ile His Gly Glu His Lys Ile Glu
            340                 345
```

```
<210> SEQ ID NO 6
<211> LENGTH: 349
<212> TYPE: PRT
<213> ORGANISM: Torenia fournieri

<400> SEQUENCE: 6

Met Ser Met Glu Val Val Pro Lys Ala Gln Pro Ile Thr Val Cys
1               5                   10                  15

Val Thr Gly Ala Ser Gly Phe Ile Gly Ser Trp Leu Val Met Lys Leu
                20                  25                  30

Leu Gln Arg Gly Tyr Thr Val His Ala Thr Val Arg Asp Pro Glu Asn
            35                  40                  45

Met Lys Lys Val Lys His Leu Leu Glu Leu Pro Arg Ala Asp Asp Ala
    50                  55                  60

Ser Leu Arg Leu Phe Lys Ala Asp Met Asn Val Glu Gly Ser Phe Asp
65                  70                  75                  80

Glu Ala Val Gly Ser Cys Glu Cys Val Phe His Met Ala Thr Pro Met
                85                  90                  95

Asp Phe Glu Ser Asp Asp Pro Glu Asn Glu Val Ile Lys Pro Thr Val
                100                 105                 110

Asp Gly Met Leu Ser Ile Ile Arg Ser Cys Ala Lys Ala Gln Thr Val
            115                 120                 125

Lys Arg Leu Ile Phe Thr Asn Ser Ala Gly Thr Leu Asn Val Glu Glu
    130                 135                 140

His Gln Lys Pro Val Tyr Asp Glu Ser Asn Trp Ser Asp Leu Asp Phe
145                 150                 155                 160

Ile Tyr Ser Thr Lys Met Thr Gly Trp Met Tyr Phe Val Ser Lys Val
                165                 170                 175

Leu Ala Glu Lys Ala Ala Ile Lys Ala Cys Lys Glu Asn Asn Ile Asp
                180                 185                 190

Phe Ile Ser Ile Ile Pro Pro Val Val Gly Pro Phe Ile Ile Asp
            195                 200                 205

Asn Trp Pro Pro Ser Leu Ile Thr Ala Leu Ser Pro Ile Thr Gly Asn
    210                 215                 220

Glu Ala His Tyr Ser Ile Ile Lys Gln Gly Gln Phe Val His Val Asp
225                 230                 235                 240

Asp Leu Cys Glu Ala His Ile Phe Leu Ser Glu His Pro Lys Thr Glu
                245                 250                 255

Glu Arg Tyr Ile Cys Ser Ser His Asp Ala Thr Ile Tyr Asp Ile Ala
            260                 265                 270

Asn Met Ile Arg Glu Lys Trp Pro Glu Tyr Asp Val Pro Thr Glu Phe
    275                 280                 285
```

```
Glu Gly Ile Asp Lys Asp Ile Pro Val Val Arg Phe Ser Ser Lys Lys
    290                 295                 300
Leu Met Gly Met Gly Phe Thr Phe Lys Tyr Thr Leu Glu Asp Met Phe
305                 310                 315                 320
Arg Glu Ala Ile Glu Thr Cys Arg Asp Lys Gly Leu Leu Pro Tyr Ser
                325                 330                 335
Thr Thr Arg Asp His Ile His Gly His Lys Ile Glu
            340                 345

<210> SEQ ID NO 7
<211> LENGTH: 1101
<212> TYPE: DNA
<213> ORGANISM: Gerbera hybrid cultivar
<220> FEATURE:
<221> NAME/KEY: CDS
<222> LOCATION: (1)..(1098)
<223> OTHER INFORMATION: Gerbera hybrid cultivar dihydroflavonol
      4-reductase

<400> SEQUENCE: 7 atg gaa gag gat tct ccg gcc acc gtt tgt gtc acc gga gcg gcc ggg      48
Met Glu Glu Asp Ser Pro Ala Thr Val Cys Val Thr Gly Ala Ala Gly
1               5                   10                  15 ttc atc ggc tca tgg ctc gtc atg aga ctt ctt gaa cgt gga tac gtt      96
Phe Ile Gly Ser Trp Leu Val Met Arg Leu Leu Glu Arg Gly Tyr Val
            20                  25                  30 gtt cat gca act gtt cgt gat ccc ggt gac ttg aag aag gtg aag cat     144
Val His Ala Thr Val Arg Asp Pro Gly Asp Leu Lys Lys Val Lys His
        35                  40                  45 ttg cta gaa cta cca aaa gca caa aca aac ttg aaa tta tgg aaa gca     192
Leu Leu Glu Leu Pro Lys Ala Gln Thr Asn Leu Lys Leu Trp Lys Ala
    50                  55                  60 gat ttg aca caa gaa gga agc ttt gat gaa gcc att caa ggt tgc cat     240
Asp Leu Thr Gln Glu Gly Ser Phe Asp Glu Ala Ile Gln Gly Cys His
65                  70                  75                  80 ggt gtc ttc cat ctg gcc act cct atg gac ttt gag tcc aag gac cct     288
Gly Val Phe His Leu Ala Thr Pro Met Asp Phe Glu Ser Lys Asp Pro
                85                  90                  95 gag aac gaa att ata aag cca aca atc gaa ggg gta tta agc atc att     336
Glu Asn Glu Ile Ile Lys Pro Thr Ile Glu Gly Val Leu Ser Ile Ile
            100                 105                 110 cga tca tgt gtc aaa gcg aaa acc gtg aag aaa cta gtg ttc acc tcc     384
Arg Ser Cys Val Lys Ala Lys Thr Val Lys Lys Leu Val Phe Thr Ser
        115                 120                 125 tcc gcc ggg acc gtg aac gga caa gag aaa caa ctg cac gtg tac gac     432
Ser Ala Gly Thr Val Asn Gly Gln Glu Lys Gln Leu His Val Tyr Asp
    130                 135                 140 gaa tct cat tgg agc gat ttg gat ttt ata tac tct aaa aaa atg act     480
Glu Ser His Trp Ser Asp Leu Asp Phe Ile Tyr Ser Lys Lys Met Thr
145                 150                 155                 160 gct tgg atg tat ttc gtg tca aaa act ttg gct gaa aaa gct gcg tgg     528
Ala Trp Met Tyr Phe Val Ser Lys Thr Leu Ala Glu Lys Ala Ala Trp
                165                 170                 175 gat gca acg aaa gga aac aac att agt ttt att agt atc atc cca acc     576
Asp Ala Thr Lys Gly Asn Asn Ile Ser Phe Ile Ser Ile Ile Pro Thr
            180                 185                 190 ctg gta gtt ggt ccg ttt atc acc tcg acg ttc cca cca agt ctc gtt     624
Leu Val Val Gly Pro Phe Ile Thr Ser Thr Phe Pro Pro Ser Leu Val
        195                 200                 205 acc gcg ctt tct ttg atc acg ggc aat gaa gca cat tat tca att ata     672
Thr Ala Leu Ser Leu Ile Thr Gly Asn Glu Ala His Tyr Ser Ile Ile
```

```
      210                 215                 220
aag caa ggt caa tat gtg cac tta gat gat ctt tgt gag tgt cat ata    720
Lys Gln Gly Gln Tyr Val His Leu Asp Asp Leu Cys Glu Cys His Ile
225                 230                 235                 240 tac cta tat gag aac cct aaa gca aaa gga aga tac att tgt tct tct    768
Tyr Leu Tyr Glu Asn Pro Lys Ala Lys Gly Arg Tyr Ile Cys Ser Ser
                    245                 250                 255 cat gat gcc acc att cat caa ttg gct aaa atc atc aaa gac aag tgg    816
His Asp Ala Thr Ile His Gln Leu Ala Lys Ile Ile Lys Asp Lys Trp
            260                 265                 270 cca gag tac tat att cca acc aag ttt ccg ggg atc gat gag gag cta    864
Pro Glu Tyr Tyr Ile Pro Thr Lys Phe Pro Gly Ile Asp Glu Glu Leu
        275                 280                 285 ccg ata gtt tct ttt tcg tca aag aag tta att gac acg ggt ttc gag    912
Pro Ile Val Ser Phe Ser Ser Lys Lys Leu Ile Asp Thr Gly Phe Glu
290                 295                 300 ttt aag tat aat tta gag gac atg ttt aaa gga gcc att gat aca tgt    960
Phe Lys Tyr Asn Leu Glu Asp Met Phe Lys Gly Ala Ile Asp Thr Cys
305                 310                 315                 320 aga gaa aag gga ttg ctt cca tat tcc aca atc aag aac cat ata aat   1008
Arg Glu Lys Gly Leu Leu Pro Tyr Ser Thr Ile Lys Asn His Ile Asn
                    325                 330                 335 ggt aac cat gtt aat ggt gtt cat cat tat ata aaa aac aat gat gat   1056
Gly Asn His Val Asn Gly Val His His Tyr Ile Lys Asn Asn Asp Asp
            340                 345                 350 gat cat gaa aag ggt ttg ctt tgt tgt tca aaa gaa ggc caa tag       1101
Asp His Glu Lys Gly Leu Leu Cys Cys Ser Lys Glu Gly Gln
        355                 360                 365

<210> SEQ ID NO 8
<211> LENGTH: 366
<212> TYPE: PRT
<213> ORGANISM: Gerbera hybrid cultivar

<400> SEQUENCE: 8

Met Glu Glu Asp Ser Pro Ala Thr Val Cys Val Thr Gly Ala Ala Gly
1               5                   10                  15

Phe Ile Gly Ser Trp Leu Val Met Arg Leu Leu Glu Arg Gly Tyr Val
                20                  25                  30

Val His Ala Thr Val Arg Asp Pro Gly Asp Leu Lys Lys Val His
            35                  40                  45

Leu Leu Glu Leu Pro Lys Ala Gln Thr Asn Leu Lys Leu Trp Lys Ala
50                  55                  60

Asp Leu Thr Gln Glu Gly Ser Phe Asp Glu Ala Ile Gln Gly Cys His
65                  70                  75                  80

Gly Val Phe His Leu Ala Thr Pro Met Asp Phe Glu Ser Lys Asp Pro
                85                  90                  95

Glu Asn Glu Ile Ile Lys Pro Thr Ile Glu Gly Val Leu Ser Ile Ile
            100                 105                 110

Arg Ser Cys Val Lys Ala Lys Thr Val Lys Lys Leu Val Phe Thr Ser
        115                 120                 125

Ser Ala Gly Thr Val Asn Gly Gln Glu Lys Gln Leu His Val Tyr Asp
    130                 135                 140

Glu Ser His Trp Ser Asp Leu Asp Phe Ile Tyr Ser Lys Lys Met Thr
145                 150                 155                 160

Ala Trp Met Tyr Phe Val Ser Lys Thr Leu Ala Glu Lys Ala Ala Trp
                165                 170                 175

Asp Ala Thr Lys Gly Asn Asn Ile Ser Phe Ile Ser Ile Ile Pro Thr
```

```
                    180             185                 190
Leu Val Val Gly Pro Phe Ile Thr Ser Thr Phe Pro Ser Leu Val
        195                 200                 205
Thr Ala Leu Ser Leu Ile Thr Gly Asn Glu Ala His Tyr Ser Ile Ile
210                 215                 220
Lys Gln Gly Gln Tyr Val His Leu Asp Asp Leu Cys Glu Cys His Ile
225                 230                 235                 240
Tyr Leu Tyr Glu Asn Pro Lys Ala Lys Gly Arg Tyr Ile Cys Ser Ser
                245                 250                 255
His Asp Ala Thr Ile His Gln Leu Ala Lys Ile Ile Lys Asp Lys Trp
            260                 265                 270
Pro Glu Tyr Tyr Ile Pro Thr Lys Phe Pro Gly Ile Asp Glu Glu Leu
        275                 280                 285
Pro Ile Val Ser Phe Ser Ser Lys Leu Ile Asp Thr Gly Phe Glu
    290                 295                 300
Phe Lys Tyr Asn Leu Glu Asp Met Phe Lys Gly Ala Ile Asp Thr Cys
305                 310                 315                 320
Arg Glu Lys Gly Leu Leu Pro Tyr Ser Thr Ile Lys Asn His Ile Asn
                325                 330                 335
Gly Asn His Val Asn Gly Val His His Tyr Ile Lys Asn Asn Asp Asp
            340                 345                 350
Asp His Glu Lys Gly Leu Leu Cys Cys Ser Lys Glu Gly Gln
        355                 360                 365

<210> SEQ ID NO 9
<211> LENGTH: 1113
<212> TYPE: DNA
<213> ORGANISM: Doritaenopsis hybrid cultivar
<220> FEATURE:
<223> OTHER INFORMATION: Doritaenopsis Sogo Vivien x Doritaenopsis Sogo
      Yenlin
<220> FEATURE:
<221> NAME/KEY: CDS
<222> LOCATION: (1)..(1110)
<223> OTHER INFORMATION: Doritaenopsis hybrid cultivar flavanone
      3-hydroxylase

<400> SEQUENCE: 9 atg gcc cca ata cca ttc cta ccg act gcg gtt aca gag aag aca ctg      48
Met Ala Pro Ile Pro Phe Leu Pro Thr Ala Val Thr Glu Lys Thr Leu
1               5                   10                  15 aga gca agc ttt gta cgg gat gag gac gag agg cca aag gta gcc tac      96
Arg Ala Ser Phe Val Arg Asp Glu Asp Glu Arg Pro Lys Val Ala Tyr
            20                  25                  30 aac gaa ttc agt aac cag att ccg gtg atc tca ctt cag ggg atc gaa     144
Asn Glu Phe Ser Asn Gln Ile Pro Val Ile Ser Leu Gln Gly Ile Glu
        35                  40                  45 gag aat gga gac gga ggt cga agg tcg gag att tgc cgg agt atc gtg     192
Glu Asn Gly Asp Gly Gly Arg Arg Ser Glu Ile Cys Arg Ser Ile Val
    50                  55                  60 gca gcg tgc gag gac tgg gga atc ttt cag gcc gtc gac cat ggt gtc     240
Ala Ala Cys Glu Asp Trp Gly Ile Phe Gln Ala Val Asp His Gly Val
65                  70                  75                  80 gat gca ggg ctc atc gca gac atg aac cgc ctt gct cga gag ttc ttc     288
Asp Ala Gly Leu Ile Ala Asp Met Asn Arg Leu Ala Arg Glu Phe Phe
                85                  90                  95 gat ctg ctg cca gag gag aag ctt cgt ttt gac atg tcc ggc ggg aag     336
Asp Leu Leu Pro Glu Glu Lys Leu Arg Phe Asp Met Ser Gly Gly Lys
            100                 105                 110 aaa ggc ggc ttc atc gtt tcc agc cat ctt cag ggt gaa gta gtt caa     384
```

```
                                                                          432
Lys Gly Gly Phe Ile Val Ser Ser His Leu Gln Gly Glu Val Val Gln
        115                 120                 125 gat tgg agg gag atc gtt acc tat ttc tca tac cca atc ggg agc cgc        432
Asp Trp Arg Glu Ile Val Thr Tyr Phe Ser Tyr Pro Ile Gly Ser Arg
130                 135                 140 gat tac tcg cgg tgg ccg gac aag ccg gag ggg tgg cgc gct gtt gtg        480
Asp Tyr Ser Arg Trp Pro Asp Lys Pro Glu Gly Trp Arg Ala Val Val
145                 150                 155                 160 gag gag tac agc gcc aag ctg atg gag ctg gcc tgc aat ctc ctc ggc        528
Glu Glu Tyr Ser Ala Lys Leu Met Glu Leu Ala Cys Asn Leu Leu Gly
                165                 170                 175 gtg cta tcg gaa gcc atg gga cta gat cgt gaa gcc cta gcc gga gcc        576
Val Leu Ser Glu Ala Met Gly Leu Asp Arg Glu Ala Leu Ala Gly Ala
            180                 185                 190 tgt atc gat atg gac cag aaa ttg gtg gtc aat ttc tac cca aaa tgc        624
Cys Ile Asp Met Asp Gln Lys Leu Val Val Asn Phe Tyr Pro Lys Cys
        195                 200                 205 ccg caa ccg gac ctc acc ctg ggc ctg aag cgc cac aca gac ccc ggc        672
Pro Gln Pro Asp Leu Thr Leu Gly Leu Lys Arg His Thr Asp Pro Gly
210                 215                 220 acc att acc ctg ttg ctt caa gat caa gtc ggc ggt ctc caa gcc acc        720
Thr Ile Thr Leu Leu Leu Gln Asp Gln Val Gly Gly Leu Gln Ala Thr
225                 230                 235                 240 aag gac gac ggt aaa acc tgg atc acc gtt cag cct gtc cag aat gct        768
Lys Asp Asp Gly Lys Thr Trp Ile Thr Val Gln Pro Val Gln Asn Ala
                245                 250                 255 ttc gtc gtt aac ctc ggc gac cac ggt cat tac ctg agc aac ggt cgg        816
Phe Val Val Asn Leu Gly Asp His Gly His Tyr Leu Ser Asn Gly Arg
            260                 265                 270 ttt aag aac gcg gac cat cag gcc gtc gtg aac tcg aat tac agc cgg        864
Phe Lys Asn Ala Asp His Gln Ala Val Val Asn Ser Asn Tyr Ser Arg
        275                 280                 285 ctt tcg atc gcg gcg ttc cag aac cct gct ccg gaa gcg gtt gtt tac        912
Leu Ser Ile Ala Ala Phe Gln Asn Pro Ala Pro Glu Ala Val Val Tyr
    290                 295                 300 ccg cta gcg gtg agg gaa gga gag agg ccg gtg atg gag gag ggc atc        960
Pro Leu Ala Val Arg Glu Gly Glu Arg Pro Val Met Glu Glu Gly Ile
305                 310                 315                 320 aca ttt gcg gag atg tat agg agg aag atg agc agg gat ctg gag ctg       1008
Thr Phe Ala Glu Met Tyr Arg Arg Lys Met Ser Arg Asp Leu Glu Leu
                325                 330                 335 gcc agg ttg aag aag atg gcg aag atg gag agt ggg gag gaa ggg gcc       1056
Ala Arg Leu Lys Lys Met Ala Lys Met Glu Ser Gly Glu Glu Gly Ala
            340                 345                 350 gca gga aag act gct gag gtt act gga gca aag gca tta aat gag att       1104
Ala Gly Lys Thr Ala Glu Val Thr Gly Ala Lys Ala Leu Asn Glu Ile
        355                 360                 365 tta gct taa                                                           1113
Leu Ala
    370
```

<210> SEQ ID NO 10
<211> LENGTH: 370
<212> TYPE: PRT
<213> ORGANISM: Doritaenopsis hybrid cultivar
<220> FEATURE:
<223> OTHER INFORMATION: Doritaenopsis Sogo Vivien x Doritaenopsis Sogo
      Yenlin

<400> SEQUENCE: 10

Met Ala Pro Ile Pro Phe Leu Pro Thr Ala Val Thr Glu Lys Thr Leu
1               5                   10                  15

Arg Ala Ser Phe Val Arg Asp Glu Asp Glu Arg Pro Lys Val Ala Tyr
            20                  25                  30

Asn Glu Phe Ser Asn Gln Ile Pro Val Ile Ser Leu Gln Gly Ile Glu
            35                  40                  45

Glu Asn Gly Asp Gly Arg Ser Glu Ile Cys Arg Ser Ile Val
50                  55                  60

Ala Ala Cys Glu Asp Trp Gly Ile Phe Gln Ala Val Asp His Gly Val
65                  70                  75                  80

Asp Ala Gly Leu Ile Ala Asp Met Asn Arg Leu Ala Arg Glu Phe Phe
                85                  90                  95

Asp Leu Leu Pro Glu Glu Lys Leu Arg Phe Asp Met Ser Gly Gly Lys
            100                 105                 110

Lys Gly Gly Phe Ile Val Ser Ser His Leu Gln Gly Glu Val Val Gln
            115                 120                 125

Asp Trp Arg Glu Ile Val Thr Tyr Phe Ser Tyr Pro Ile Gly Ser Arg
130                 135                 140

Asp Tyr Ser Arg Trp Pro Asp Lys Pro Glu Gly Trp Arg Ala Val Val
145                 150                 155                 160

Glu Glu Tyr Ser Ala Lys Leu Met Glu Leu Ala Cys Asn Leu Leu Gly
                165                 170                 175

Val Leu Ser Glu Ala Met Gly Leu Asp Arg Glu Ala Leu Ala Gly Ala
            180                 185                 190

Cys Ile Asp Met Asp Gln Lys Leu Val Val Asn Phe Tyr Pro Lys Cys
            195                 200                 205

Pro Gln Pro Asp Leu Thr Leu Gly Leu Lys Arg His Thr Asp Pro Gly
            210                 215                 220

Thr Ile Thr Leu Leu Leu Gln Asp Gln Val Gly Gly Leu Gln Ala Thr
225                 230                 235                 240

Lys Asp Asp Gly Lys Thr Trp Ile Thr Val Gln Pro Val Gln Asn Ala
                245                 250                 255

Phe Val Val Asn Leu Gly Asp His Gly His Tyr Leu Ser Asn Gly Arg
            260                 265                 270

Phe Lys Asn Ala Asp His Gln Ala Val Val Asn Ser Asn Tyr Ser Arg
            275                 280                 285

Leu Ser Ile Ala Ala Phe Gln Asn Pro Ala Pro Glu Ala Val Val Tyr
            290                 295                 300

Pro Leu Ala Val Arg Glu Gly Glu Arg Pro Val Met Glu Glu Gly Ile
305                 310                 315                 320

Thr Phe Ala Glu Met Tyr Arg Arg Lys Met Ser Arg Asp Leu Glu Leu
                325                 330                 335

Ala Arg Leu Lys Lys Met Ala Lys Met Glu Ser Gly Glu Glu Gly Ala
            340                 345                 350

Ala Gly Lys Thr Ala Glu Val Thr Gly Ala Lys Ala Leu Asn Glu Ile
            355                 360                 365

Leu Ala
    370

<210> SEQ ID NO 11
<211> LENGTH: 1083
<212> TYPE: DNA
<213> ORGANISM: Doritaenopsis hybrid cultivar
<220> FEATURE:
<223> OTHER INFORMATION: Doritaenopsis Sogo Vivien x Doritaenopsis Sogo
      Yenlin
<220> FEATURE:
<221> NAME/KEY: CDS

<222> LOCATION: (1)..(1080)

<400> SEQUENCE: 11

```
atg gcc acc aaa gca atc cca cct act cca aga gtg gag atc ctc gca    48
Met Ala Thr Lys Ala Ile Pro Pro Thr Pro Arg Val Glu Ile Leu Ala
1               5                   10                  15 aac agc ggc ctc agc ttc atc ccc gcc gag ttc gtc cgc cca caa tct    96
Asn Ser Gly Leu Ser Phe Ile Pro Ala Glu Phe Val Arg Pro Gln Ser
            20                  25                  30 gaa cgc caa cac ctc caa gac tcc ctc aac aag aac ccc tgc ggt gtt   144
Glu Arg Gln His Leu Gln Asp Ser Leu Asn Lys Asn Pro Cys Gly Val
        35                  40                  45 gag atc cca atc gtg gat ctc ggg ggg ttc tca tca gag gaa ggg cgg   192
Glu Ile Pro Ile Val Asp Leu Gly Gly Phe Ser Ser Glu Glu Gly Arg
    50                  55                  60 cgg cgg cgg tgc gtg gag gag gtg atg gca gct gca gag gag tgg ggg   240
Arg Arg Arg Cys Val Glu Glu Val Met Ala Ala Ala Glu Glu Trp Gly
65                  70                  75                  80 gtg atg ttc ctc gtg aac cac ggt gtg ccg gag gag ctc att gag cgg   288
Val Met Phe Leu Val Asn His Gly Val Pro Glu Glu Leu Ile Glu Arg
                85                  90                  95 ctg cag gcg acg ggg aag ggg ttc ttc gaa ttg ccg gtg gac gag aag   336
Leu Gln Ala Thr Gly Lys Gly Phe Phe Glu Leu Pro Val Asp Glu Lys
            100                 105                 110 gag aag tat gct aat gat cag tca agg gga cag ata cag ggc tat ggg   384
Glu Lys Tyr Ala Asn Asp Gln Ser Arg Gly Gln Ile Gln Gly Tyr Gly
        115                 120                 125 agc aag cta gca aat aat gaa aac ggt ata ctt gag tgg cag gat tac   432
Ser Lys Leu Ala Asn Asn Glu Asn Gly Ile Leu Glu Trp Gln Asp Tyr
    130                 135                 140 ttt ttt cac ctc gtc tac ccg ccg gag aag acg gac ctc acc atc tgg   480
Phe Phe His Leu Val Tyr Pro Pro Glu Lys Thr Asp Leu Thr Ile Trp
145                 150                 155                 160 ccg act gaa ccc gcg gac tac att gcg acc aca acc tcg ttc gcc aag   528
Pro Thr Glu Pro Ala Asp Tyr Ile Ala Thr Thr Thr Ser Phe Ala Lys
                165                 170                 175 gag ctc cga acc cta gcc tca aaa atg ttc tcc ata ctc tcc ctc ggt   576
Glu Leu Arg Thr Leu Ala Ser Lys Met Phe Ser Ile Leu Ser Leu Gly
            180                 185                 190 ctc ggc ctc gac caa aac aag ctc gaa gct gag ctc ggc ggc caa gac   624
Leu Gly Leu Asp Gln Asn Lys Leu Glu Ala Glu Leu Gly Gly Gln Asp
        195                 200                 205 gac ctc ctc ctc cag ctt aag atc aat tac tac ccg ccc tgc ccg cag   672
Asp Leu Leu Leu Gln Leu Lys Ile Asn Tyr Tyr Pro Pro Cys Pro Gln
    210                 215                 220 ccg gag ctg gcc ctc ggc gtc gag gcc cac acc gac gtc agc tcc ctc   720
Pro Glu Leu Ala Leu Gly Val Glu Ala His Thr Asp Val Ser Ser Leu
225                 230                 235                 240 tcc ttc atc ctt cac aac ggg atc ccc ggc ctc cag gtc ttc aag aac   768
Ser Phe Ile Leu His Asn Gly Ile Pro Gly Leu Gln Val Phe Lys Asn
                245                 250                 255 ggc gcc ggc tgg atc acc gct ccc ctc gtc cca aac tcg atc atc gtt   816
Gly Ala Gly Trp Ile Thr Ala Pro Leu Val Pro Asn Ser Ile Ile Val
            260                 265                 270 cac gtc ggg gat gcg ctc gag atc ctc agc aat ggg agg tgc cac agc   864
His Val Gly Asp Ala Leu Glu Ile Leu Ser Asn Gly Arg Cys His Ser
        275                 280                 285 gtt ctt cac cga gga ctt gtt act aag gaa aat gtt cgg atc tcg tgg   912
Val Leu His Arg Gly Leu Val Thr Lys Glu Asn Val Arg Ile Ser Trp
    290                 295                 300
```

-continued

```
gcg gtt ttc tgc gag ccg ccg agg gag aag gtg gtt ctt cgg ccg ctg    960
Ala Val Phe Cys Glu Pro Pro Arg Glu Lys Val Val Leu Arg Pro Leu
305                 310                 315                 320 ctg gag ttg att ggg aag ggg gag gtg gcg agg ttt gag ccg cgg act   1008
Leu Glu Leu Ile Gly Lys Gly Glu Val Ala Arg Phe Glu Pro Arg Thr
                325                 330                 335 ttt gcg gag cat ttg gag agg aag ctg ttc aag ccg agg gtg gag ggt   1056
Phe Ala Glu His Leu Glu Arg Lys Leu Phe Lys Pro Arg Val Glu Gly
            340                 345                 350 tgc ggg gag aag gcg cct gtg gat tga                               1083
Cys Gly Glu Lys Ala Pro Val Asp
                355                 360
```

<210> SEQ ID NO 12
<211> LENGTH: 360
<212> TYPE: PRT
<213> ORGANISM: Doritaenopsis hybrid cultivar
<220> FEATURE:
<223> OTHER INFORMATION: Doritaenopsis Sogo Vivien x Doritaenopsis Sogo Yenlin

<400> SEQUENCE: 12

```
Met Ala Thr Lys Ala Ile Pro Pro Thr Pro Arg Val Glu Ile Leu Ala
1               5                   10                  15

Asn Ser Gly Leu Ser Phe Ile Pro Ala Glu Phe Val Arg Pro Gln Ser
            20                  25                  30

Glu Arg Gln His Leu Gln Asp Ser Leu Asn Lys Asn Pro Cys Gly Val
        35                  40                  45

Glu Ile Pro Ile Val Asp Leu Gly Gly Phe Ser Ser Glu Glu Gly Arg
    50                  55                  60

Arg Arg Arg Cys Val Glu Glu Val Met Ala Ala Ala Glu Glu Trp Gly
65                  70                  75                  80

Val Met Phe Leu Val Asn His Gly Val Pro Glu Glu Leu Ile Glu Arg
                85                  90                  95

Leu Gln Ala Thr Gly Lys Gly Phe Phe Glu Leu Pro Val Asp Glu Lys
            100                 105                 110

Glu Lys Tyr Ala Asn Asp Gln Ser Arg Gly Gln Ile Gln Gly Tyr Gly
        115                 120                 125

Ser Lys Leu Ala Asn Asn Glu Asn Gly Ile Leu Glu Trp Gln Asp Tyr
    130                 135                 140

Phe Phe His Leu Val Tyr Pro Pro Glu Lys Thr Asp Leu Thr Ile Trp
145                 150                 155                 160

Pro Thr Glu Pro Ala Asp Tyr Ile Ala Thr Thr Thr Ser Phe Ala Lys
                165                 170                 175

Glu Leu Arg Thr Leu Ala Ser Lys Met Phe Ser Ile Leu Ser Leu Gly
            180                 185                 190

Leu Gly Leu Asp Gln Asn Lys Leu Glu Ala Glu Leu Gly Gly Gln Asp
        195                 200                 205

Asp Leu Leu Leu Gln Leu Lys Ile Asn Tyr Tyr Pro Pro Cys Pro Gln
    210                 215                 220

Pro Glu Leu Ala Leu Gly Val Glu Ala His Thr Asp Val Ser Ser Leu
225                 230                 235                 240

Ser Phe Ile Leu His Asn Gly Ile Pro Gly Leu Gln Val Phe Lys Asn
                245                 250                 255

Gly Ala Gly Trp Ile Thr Ala Pro Leu Val Pro Asn Ser Ile Ile Val
            260                 265                 270

His Val Gly Asp Ala Leu Glu Ile Leu Ser Asn Gly Arg Cys His Ser
        275                 280                 285
```

```
Val Leu His Arg Gly Leu Val Thr Lys Glu Asn Val Arg Ile Ser Trp
        290                 295                 300

Ala Val Phe Cys Glu Pro Pro Arg Glu Lys Val Val Leu Arg Pro Leu
305                 310                 315                 320

Leu Glu Leu Ile Gly Lys Gly Glu Val Ala Arg Phe Glu Pro Arg Thr
                325                 330                 335

Phe Ala Glu His Leu Glu Arg Lys Leu Phe Lys Pro Arg Val Glu Gly
            340                 345                 350

Cys Gly Glu Lys Ala Pro Val Asp
        355                 360

<210> SEQ ID NO 13
<211> LENGTH: 1068
<212> TYPE: DNA
<213> ORGANISM: Gerbera hybrid cultivar
<220> FEATURE:
<221> NAME/KEY: CDS
<222> LOCATION: (1)..(1065)
<223> OTHER INFORMATION: Gerbera hybrid cultivar anthocyanidin synthase

<400> SEQUENCE: 13 atg gtg att caa gca acc aca aga gtc gaa agc tta tca acg agc ggc      48
Met Val Ile Gln Ala Thr Thr Arg Val Glu Ser Leu Ser Thr Ser Gly
1               5                  10                  15 atc cac cag atc ccg aaa gaa tac atc cgc cca caa gaa gaa cta aga      96
Ile His Gln Ile Pro Lys Glu Tyr Ile Arg Pro Gln Glu Glu Leu Arg
                20                  25                  30 agc atc aca aac atc ttc gac gaa gaa aca aac aag caa aaa cca caa     144
Ser Ile Thr Asn Ile Phe Asp Glu Glu Thr Asn Lys Gln Lys Pro Gln
            35                  40                  45 gtc ccc acc gtg gat cta acg gac atc gaa tcc gac gac ccg gaa aaa     192
Val Pro Thr Val Asp Leu Thr Asp Ile Glu Ser Asp Asp Pro Glu Lys
        50                  55                  60 aga cac aag tgt ttg gaa gag ctt aag aaa gcg gcc atg gag tgg ggt     240
Arg His Lys Cys Leu Glu Glu Leu Lys Lys Ala Ala Met Glu Trp Gly
65                  70                  75                  80 gtt atg cat gtc gtg aac cat gga gtc tcc ggc gac ttg att ggc cgt     288
Val Met His Val Val Asn His Gly Val Ser Gly Asp Leu Ile Gly Arg
                85                  90                  95 gtt aag gcc gcc ggc gag ggg ttt ttt ggg ctg ccg gtg gag gag aag     336
Val Lys Ala Ala Gly Glu Gly Phe Phe Gly Leu Pro Val Glu Glu Lys
                100                 105                 110 gag agg tat ggg aat gat cca gac gga ggg agg att caa ggg tat gga     384
Glu Arg Tyr Gly Asn Asp Pro Asp Gly Gly Arg Ile Gln Gly Tyr Gly
            115                 120                 125 agt aaa ttg gct aat aat gct tct ggg cag ctt gaa tgg gag gat tac     432
Ser Lys Leu Ala Asn Asn Ala Ser Gly Gln Leu Glu Trp Glu Asp Tyr
        130                 135                 140 ttt ttt cac ctt gtg ttc ccg gag gag aaa cgt gat ttg acc att tgg     480
Phe Phe His Leu Val Phe Pro Glu Glu Lys Arg Asp Leu Thr Ile Trp
145                 150                 155                 160 ccc acg acg cct agt gac tac acc gat gcc acc acc gag tat gct aag     528
Pro Thr Thr Pro Ser Asp Tyr Thr Asp Ala Thr Thr Glu Tyr Ala Lys
                165                 170                 175 cag cta cga gca ttg gca acc aag ata ctc tcg gcg cta tct tta ggg     576
Gln Leu Arg Ala Leu Ala Thr Lys Ile Leu Ser Ala Leu Ser Leu Gly
                180                 185                 190 tta gga ttg gag gag ggt cgg cta gag aaa gag gta gga ggg ata gag     624
Leu Gly Leu Glu Glu Gly Arg Leu Glu Lys Glu Val Gly Gly Ile Glu
            195                 200                 205
```

```
gag ctt atc ctt caa cta aag att aac tat tac cca aaa tgc cct caa    672
Glu Leu Ile Leu Gln Leu Lys Ile Asn Tyr Tyr Pro Lys Cys Pro Gln
    210                 215                 220 ccc gag cta gcc ctt ggt gtg gaa gct cac acc gat gta agt gca ctc    720
Pro Glu Leu Ala Leu Gly Val Glu Ala His Thr Asp Val Ser Ala Leu
225                 230                 235                 240 acg ttc atc ctc cac aac atg gtc cca ggg ctc caa ctc ttc tat gac    768
Thr Phe Ile Leu His Asn Met Val Pro Gly Leu Gln Leu Phe Tyr Asp
                245                 250                 255 gga caa tgg gtt agt gca caa tgt gtg cca gac tcc atc atc tta cac    816
Gly Gln Trp Val Ser Ala Gln Cys Val Pro Asp Ser Ile Ile Leu His
            260                 265                 270 att ggt gac acc ctt gag atc ctg agt aat gga aaa tac aag agt atc    864
Ile Gly Asp Thr Leu Glu Ile Leu Ser Asn Gly Lys Tyr Lys Ser Ile
        275                 280                 285 ctc cat agg ggg ctc gtg aac aaa gag aag gtc agg att tct tgg gcg    912
Leu His Arg Gly Leu Val Asn Lys Glu Lys Val Arg Ile Ser Trp Ala
    290                 295                 300 gtt ttt tgt gaa ccg ccc aag gag aaa atc atc ctg aaa ccg ttg cca    960
Val Phe Cys Glu Pro Pro Lys Glu Lys Ile Ile Leu Lys Pro Leu Pro
305                 310                 315                 320 gag acg gtt tct gag gca gag ccg cca ctc ttt ccg cct cgg acc ttt    1008
Glu Thr Val Ser Glu Ala Glu Pro Pro Leu Phe Pro Pro Arg Thr Phe
                325                 330                 335 cag caa cat atg gaa cac aag ttg ttt agg aag aat aaa gac gaa gtg    1056
Gln Gln His Met Glu His Lys Leu Phe Arg Lys Asn Lys Asp Glu Val
            340                 345                 350 atg caa aac tag                                                    1068
Met Gln Asn
        355

<210> SEQ ID NO 14
<211> LENGTH: 355
<212> TYPE: PRT
<213> ORGANISM: Gerbera hybrid cultivar

<400> SEQUENCE: 14

Met Val Ile Gln Ala Thr Thr Arg Val Glu Ser Leu Ser Thr Ser Gly
1               5                   10                  15

Ile His Gln Ile Pro Lys Glu Tyr Ile Arg Pro Gln Glu Glu Leu Arg
            20                  25                  30

Ser Ile Thr Asn Ile Phe Asp Glu Glu Thr Asn Lys Gln Lys Pro Gln
        35                  40                  45

Val Pro Thr Val Asp Leu Thr Asp Ile Glu Ser Asp Asp Pro Glu Lys
    50                  55                  60

Arg His Lys Cys Leu Glu Glu Leu Lys Lys Ala Ala Met Glu Trp Gly
65                  70                  75                  80

Val Met His Val Asn His Gly Val Ser Gly Asp Leu Ile Gly Arg
                85                  90                  95

Val Lys Ala Ala Gly Glu Gly Phe Phe Gly Leu Pro Val Glu Glu Lys
            100                 105                 110

Glu Arg Tyr Gly Asn Asp Pro Asp Gly Gly Arg Ile Gln Gly Tyr Gly
        115                 120                 125

Ser Lys Leu Ala Asn Asn Ala Ser Gly Gln Leu Glu Trp Glu Asp Tyr
    130                 135                 140

Phe Phe His Leu Val Phe Pro Glu Glu Lys Arg Asp Leu Thr Ile Trp
145                 150                 155                 160

Pro Thr Thr Pro Ser Asp Tyr Thr Asp Ala Thr Thr Glu Tyr Ala Lys
                165                 170                 175
```

-continued

```
Gln Leu Arg Ala Leu Ala Thr Lys Ile Leu Ser Ala Leu Ser Leu Gly
                180                 185                 190
Leu Gly Leu Glu Glu Gly Arg Leu Glu Lys Glu Val Gly Gly Ile Glu
            195                 200                 205
Glu Leu Ile Leu Gln Leu Lys Ile Asn Tyr Tyr Pro Lys Cys Pro Gln
        210                 215                 220
Pro Glu Leu Ala Leu Gly Val Glu Ala His Thr Asp Val Ser Ala Leu
225                 230                 235                 240
Thr Phe Ile Leu His Asn Met Val Pro Gly Leu Gln Leu Phe Tyr Asp
                245                 250                 255
Gly Gln Trp Val Ser Ala Gln Cys Val Pro Asp Ser Ile Ile Leu His
            260                 265                 270
Ile Gly Asp Thr Leu Glu Ile Leu Ser Asn Gly Lys Tyr Lys Ser Ile
        275                 280                 285
Leu His Arg Gly Leu Val Asn Lys Glu Lys Val Arg Ile Ser Trp Ala
    290                 295                 300
Val Phe Cys Glu Pro Pro Lys Glu Lys Ile Ile Leu Lys Pro Leu Pro
305                 310                 315                 320
Glu Thr Val Ser Glu Ala Glu Pro Pro Leu Phe Pro Pro Arg Thr Phe
                325                 330                 335
Gln Gln His Met Glu His Lys Leu Phe Arg Lys Asn Lys Asp Glu Val
            340                 345                 350
Met Gln Asn
        355

<210> SEQ ID NO 15
<211> LENGTH: 1140
<212> TYPE: DNA
<213> ORGANISM: Doritaenopsis hybrid cultivar
<220> FEATURE:
<223> OTHER INFORMATION: Doritaenopsis Queen Beer
<220> FEATURE:
<221> NAME/KEY: CDS
<222> LOCATION: (1)..(1137)
<223> OTHER INFORMATION: Doritaenopsis hybrid cultivar dihydroflavonol
      4-reductase

<400> SEQUENCE: 15 atg gag gat gtg agg aag ggt cct gtt gtg gtg acg gga gcc agc ggg    48
Met Glu Asp Val Arg Lys Gly Pro Val Val Val Thr Gly Ala Ser Gly
1               5                   10                  15 tac gtg ggt tca tgg ctg gtt atg aag ctt ctt cga aag ggt tat gag    96
Tyr Val Gly Ser Trp Leu Val Met Lys Leu Leu Arg Lys Gly Tyr Glu
            20                  25                  30 gtc agg gct aca gtc aga gat cca aca aat tct aaa aaa gtg aag ccg   144
Val Arg Ala Thr Val Arg Asp Pro Thr Asn Ser Lys Lys Val Lys Pro
        35                  40                  45 ttg ttg gat ctt ccg ggc tcg aat gaa ctg ctc agc ata tgg aaa gca   192
Leu Leu Asp Leu Pro Gly Ser Asn Glu Leu Leu Ser Ile Trp Lys Ala
    50                  55                  60 gat cta aat gac att gaa ggg agc ttc gat gag gtg ata cgt ggt tgt   240
Asp Leu Asn Asp Ile Glu Gly Ser Phe Asp Glu Val Ile Arg Gly Cys
65                  70                  75                  80 gtt ggg gtg ttc cat gtc gct act ccc atg aat ttt caa tcc aaa gac   288
Val Gly Val Phe His Val Ala Thr Pro Met Asn Phe Gln Ser Lys Asp
                85                  90                  95 cct gag aac gaa gtg ata caa ccg gca atc aac ggt ttg ctg agc atc   336
Pro Glu Asn Glu Val Ile Gln Pro Ala Ile Asn Gly Leu Leu Ser Ile
            100                 105                 110
```

```
ctg agg tca tgc aaa agg tcg ggc agc gta agg cgc gtg atc ttc aca    384
Leu Arg Ser Cys Lys Arg Ser Gly Ser Val Arg Arg Val Ile Phe Thr
        115                 120                 125 tct tcc gca gga aca gtc aac gtg gag gaa cgc cga gca ccg gtg tac    432
Ser Ser Ala Gly Thr Val Asn Val Glu Glu Arg Arg Ala Pro Val Tyr
    130                 135                 140 gac gag agc tcc tgg agc gac ctc gat ttc atc acc cgt gtc aaa atg    480
Asp Glu Ser Ser Trp Ser Asp Leu Asp Phe Ile Thr Arg Val Lys Met
145                 150                 155                 160 acc ggt tgg atg tac ttc gta tca aaa aca ctt gcg gag aag gct gct    528
Thr Gly Trp Met Tyr Phe Val Ser Lys Thr Leu Ala Glu Lys Ala Ala
                165                 170                 175 tgg gag ttt gtg aaa gaa aat gac gtt gat ttt ata gcc ata att ccc    576
Trp Glu Phe Val Lys Glu Asn Asp Val Asp Phe Ile Ala Ile Ile Pro
            180                 185                 190 act ttg gtg gtg ggt tcc ttc ata aca gat gag atg ccg cca agt ttg    624
Thr Leu Val Val Gly Ser Phe Ile Thr Asp Glu Met Pro Pro Ser Leu
        195                 200                 205 acc act gca ttt tca tta att aca gga aat gaa gct cat tac tcg ata    672
Thr Thr Ala Phe Ser Leu Ile Thr Gly Asn Glu Ala His Tyr Ser Ile
    210                 215                 220 ata aag caa gct caa ttt gtt cat ttg gat gac tta tgt gat gct cat    720
Ile Lys Gln Ala Gln Phe Val His Leu Asp Asp Leu Cys Asp Ala His
225                 230                 235                 240 att ttc ctt ttc gaa cat ccc gaa gca aat ggt agg tac att tgt tct    768
Ile Phe Leu Phe Glu His Pro Glu Ala Asn Gly Arg Tyr Ile Cys Ser
                245                 250                 255 tca cat gat tcg aca att tat gac ttg gca aaa atg ctg aag aag aga    816
Ser His Asp Ser Thr Ile Tyr Asp Leu Ala Lys Met Leu Lys Lys Arg
            260                 265                 270 tat gcc aca tat gcc ata cct caa gag ttt aaa gat att gat cca aat    864
Tyr Ala Thr Tyr Ala Ile Pro Gln Glu Phe Lys Asp Ile Asp Pro Asn
        275                 280                 285 att aag aga gtg agt ttc tct tct aag aag ttc atg gac ttg ggg ttc    912
Ile Lys Arg Val Ser Phe Ser Ser Lys Lys Phe Met Asp Leu Gly Phe
    290                 295                 300 aag tac aag tac act att gag gag atg ttt gat gat gct att aag acc    960
Lys Tyr Lys Tyr Thr Ile Glu Glu Met Phe Asp Asp Ala Ile Lys Thr
305                 310                 315                 320 tgc agg gaa aag aat ctc tta ccg ccc aac act gag gaa cca gcc tta   1008
Cys Arg Glu Lys Asn Leu Leu Pro Pro Asn Thr Glu Glu Pro Ala Leu
                325                 330                 335 ctt gcc gaa aag tac gaa gaa atg aaa gaa caa ttg cag tta agt gaa   1056
Leu Ala Glu Lys Tyr Glu Glu Met Lys Glu Gln Leu Gln Leu Ser Glu
            340                 345                 350 aga aga atg aga agt ttg aaa att ctt tat gtt atc ctt tta ttt aca   1104
Arg Arg Met Arg Ser Leu Lys Ile Leu Tyr Val Ile Leu Leu Phe Thr
        355                 360                 365 cat ctg ctt tat tat gca tgg tta tat ctt gac tga                   1140
His Leu Leu Tyr Tyr Ala Trp Leu Tyr Leu Asp
    370                 375

<210> SEQ ID NO 16
<211> LENGTH: 379
<212> TYPE: PRT
<213> ORGANISM: Doritaenopsis hybrid cultivar
<220> FEATURE:
<223> OTHER INFORMATION: Doritaenopsis Queen Beer

<400> SEQUENCE: 16

Met Glu Asp Val Arg Lys Gly Pro Val Val Thr Gly Ala Ser Gly
1               5                   10                  15
```

Tyr Val Gly Ser Trp Leu Val Met Lys Leu Leu Arg Lys Gly Tyr Glu
            20                  25                  30

Val Arg Ala Thr Val Arg Asp Pro Thr Asn Ser Lys Lys Val Lys Pro
            35                  40                  45

Leu Leu Asp Leu Pro Gly Ser Asn Glu Leu Leu Ser Ile Trp Lys Ala
            50                  55                  60

Asp Leu Asn Asp Ile Glu Gly Ser Phe Asp Glu Val Ile Arg Gly Cys
65                  70                  75                  80

Val Gly Val Phe His Val Ala Thr Pro Met Asn Phe Gln Ser Lys Asp
                85                  90                  95

Pro Glu Asn Glu Val Ile Gln Pro Ala Ile Asn Gly Leu Leu Ser Ile
                100                 105                 110

Leu Arg Ser Cys Lys Arg Ser Gly Ser Val Arg Val Ile Phe Thr
            115                 120                 125

Ser Ser Ala Gly Thr Val Asn Val Glu Glu Arg Arg Ala Pro Val Tyr
            130                 135                 140

Asp Glu Ser Ser Trp Ser Asp Leu Asp Phe Ile Thr Arg Val Lys Met
145                 150                 155                 160

Thr Gly Trp Met Tyr Phe Val Ser Lys Thr Leu Ala Glu Lys Ala Ala
                165                 170                 175

Trp Glu Phe Val Lys Glu Asn Asp Val Asp Phe Ile Ala Ile Ile Pro
                180                 185                 190

Thr Leu Val Val Gly Ser Phe Ile Thr Asp Glu Met Pro Pro Ser Leu
            195                 200                 205

Thr Thr Ala Phe Ser Leu Ile Thr Gly Asn Glu Ala His Tyr Ser Ile
210                 215                 220

Ile Lys Gln Ala Gln Phe Val His Leu Asp Asp Leu Cys Asp Ala His
225                 230                 235                 240

Ile Phe Leu Phe Glu His Pro Glu Ala Asn Gly Arg Tyr Ile Cys Ser
                245                 250                 255

Ser His Asp Ser Thr Ile Tyr Asp Leu Ala Lys Met Leu Lys Lys Arg
            260                 265                 270

Tyr Ala Thr Tyr Ala Ile Pro Gln Glu Phe Lys Asp Ile Asp Pro Asn
            275                 280                 285

Ile Lys Arg Val Ser Phe Ser Ser Lys Lys Phe Met Asp Leu Gly Phe
290                 295                 300

Lys Tyr Lys Tyr Thr Ile Glu Glu Met Phe Asp Asp Ala Ile Lys Thr
305                 310                 315                 320

Cys Arg Glu Lys Asn Leu Leu Pro Pro Asn Thr Glu Glu Pro Ala Leu
                325                 330                 335

Leu Ala Glu Lys Tyr Glu Glu Met Lys Glu Gln Leu Gln Leu Ser Glu
            340                 345                 350

Arg Arg Met Arg Ser Leu Lys Ile Leu Tyr Val Ile Leu Leu Phe Thr
            355                 360                 365

His Leu Leu Tyr Tyr Ala Trp Leu Tyr Leu Asp
    370                 375

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide SAS-S

<400> SEQUENCE: 17

```
ctagctagcg gcgcgcctgc aggatatcat ttaaatcccg gg                              42
```

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide SAS-AS

<400> SEQUENCE: 18

```
cccgggattt aaatgatatc ctgcaggcgc gccgctagct ag                              42
```

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer T-CaMV35S-SseI-F

<400> SEQUENCE: 19

```
aacctgcagg aaatcaccag tctctctcta                                           30
```

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer T-CaMV35S-AscI-R

<400> SEQUENCE: 20

```
ggcgcgccat cgataagggg ttattag                                              27
```

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer PhCHS3 F1

<400> SEQUENCE: 21

```
aagcttgtga gagacgacgg a                                                    21
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer PhCHS3 R1

<400> SEQUENCE: 22

```
tggccctaat ccttcaaatt                                                      20
```

<210> SEQ ID NO 23
<211> LENGTH: 1185
<212> TYPE: DNA
<213> ORGANISM: Doritaenopsis hybrid cultivar
<220> FEATURE:
<223> OTHER INFORMATION: Doritaenopsis Sogo Vivien x Doritaenopsis Sogo
      Yenlin
<220> FEATURE:
<221> NAME/KEY: CDS
<222> LOCATION: (1)..(1182)
<223> OTHER INFORMATION: Doritaenopsis hybrid cultivar chalcone synthase

<400> SEQUENCE: 23

```
atg gcg ccg gcg atg gag gag atc agg cga act cag aga gct gag ggc      48
Met Ala Pro Ala Met Glu Glu Ile Arg Arg Thr Gln Arg Ala Glu Gly
 1               5                  10                  15 ccc gcg gcg gtg ctc gca atc ggc acc tcc acg ccg ccg aac gct ctg      96
Pro Ala Ala Val Leu Ala Ile Gly Thr Ser Thr Pro Pro Asn Ala Leu
            20                  25                  30 tat cag gcc gat tat ccc gat tat tac ttc aga atc acc aac tgc gag     144
Tyr Gln Ala Asp Tyr Pro Asp Tyr Tyr Phe Arg Ile Thr Asn Cys Glu
        35                  40                  45 cat ctc act gac ctc aag gag aag ttc aag cga atg tgc gag aaa tcc     192
His Leu Thr Asp Leu Lys Glu Lys Phe Lys Arg Met Cys Glu Lys Ser
    50                  55                  60 atg ata aaa aaa cgg tac atg tat cta aca gaa gaa ttc ctg aaa gaa     240
Met Ile Lys Lys Arg Tyr Met Tyr Leu Thr Glu Glu Phe Leu Lys Glu
65                  70                  75                  80 aat ccc aat atc tgc gca ttc atg gct cct tca ctc gac gcc cgg caa     288
Asn Pro Asn Ile Cys Ala Phe Met Ala Pro Ser Leu Asp Ala Arg Gln
                85                  90                  95 gac ata gtt gtc gcc gag gtc ccg aag ctc gcc aaa gag gcc gcc gcg     336
Asp Ile Val Val Ala Glu Val Pro Lys Leu Ala Lys Glu Ala Ala Ala
            100                 105                 110 cgc gcc atc aag gaa tgg gga cac ccc aaa tca cgc ata act cat ctc     384
Arg Ala Ile Lys Glu Trp Gly His Pro Lys Ser Arg Ile Thr His Leu
        115                 120                 125 atc ttc tgc acc acc agc ggc gtc gac atg ccc ggc gcc gac tac caa     432
Ile Phe Cys Thr Thr Ser Gly Val Asp Met Pro Gly Ala Asp Tyr Gln
    130                 135                 140 ctc acc cgc ctc ctc ggt ctc cgc ccc tcc gtc aac aga ttc atg ctc     480
Leu Thr Arg Leu Leu Gly Leu Arg Pro Ser Val Asn Arg Phe Met Leu
145                 150                 155                 160 tac cag cag ggc tgc ttc gcc ggc ggc acc gtc ctc cgc ctc gcc aag     528
Tyr Gln Gln Gly Cys Phe Ala Gly Gly Thr Val Leu Arg Leu Ala Lys
                165                 170                 175 gat ctc gcc gag aac aac gcc ggc gcc cgc gtg ctc gtc gtt tgc tcc     576
Asp Leu Ala Glu Asn Asn Ala Gly Ala Arg Val Leu Val Val Cys Ser
            180                 185                 190 gaa atc acc gcc gtc act ttc cgc ggc ccg tcg gaa tcc cat ctc gat     624
Glu Ile Thr Ala Val Thr Phe Arg Gly Pro Ser Glu Ser His Leu Asp
        195                 200                 205 tcc ctc gtc gga cag gcg ctc ttc ggc gac ggc gcc gcc gct atc att     672
Ser Leu Val Gly Gln Ala Leu Phe Gly Asp Gly Ala Ala Ala Ile Ile
    210                 215                 220 gtc gga tcc gac cct gat tta gcc acc gag cgc cct ctg ttt caa cta     720
Val Gly Ser Asp Pro Asp Leu Ala Thr Glu Arg Pro Leu Phe Gln Leu
225                 230                 235                 240 gtc tct gct tcc caa acc atc ctt ccc gaa tca gag ggc gcc att gat     768
Val Ser Ala Ser Gln Thr Ile Leu Pro Glu Ser Glu Gly Ala Ile Asp
                245                 250                 255 ggc cac ctt cgt gaa atc ggg ctc acc ttc cac cta ctc aaa gac gtc     816
Gly His Leu Arg Glu Ile Gly Leu Thr Phe His Leu Leu Lys Asp Val
            260                 265                 270 ccc ggc ctc att tct aaa aac att caa aaa tgt ctc ctt gag gcc ttc     864
Pro Gly Leu Ile Ser Lys Asn Ile Gln Lys Cys Leu Leu Glu Ala Phe
        275                 280                 285 aag cca ctt ggt gtg ctt gat tgg aac tct att ttt tgg atc gct cac     912
Lys Pro Leu Gly Val Leu Asp Trp Asn Ser Ile Phe Trp Ile Ala His
    290                 295                 300 ccg ggc ggc ccg gct ata ctc gat caa gtt gag acc aag ctc ggt cta     960
Pro Gly Gly Pro Ala Ile Leu Asp Gln Val Glu Thr Lys Leu Gly Leu
```

```
Pro Gly Gly Pro Ala Ile Leu Asp Gln Val Glu Thr Lys Leu Gly Leu
305                 310                 315                 320 aag tcc gag aag ctc gcc gcg agt aga aat gtg ctc gct gac tac ggt      1008
Lys Ser Glu Lys Leu Ala Ala Ser Arg Asn Val Leu Ala Asp Tyr Gly
            325                 330                 335 aac atg tcg agc gca tgc gtt ctt ttc ata ctc gat gag atg cga agg      1056
Asn Met Ser Ser Ala Cys Val Leu Phe Ile Leu Asp Glu Met Arg Arg
        340                 345                 350 cga tcg gca gag gct ggg cag tcg acc act ggc gag ggt ttg gag tgg      1104
Arg Ser Ala Glu Ala Gly Gln Ser Thr Thr Gly Glu Gly Leu Glu Trp
    355                 360                 365 gga gtt cta ttc ggg ttc ggt ccg gga ctt acg gtc gag act gtt gta      1152
Gly Val Leu Phe Gly Phe Gly Pro Gly Leu Thr Val Glu Thr Val Val
370                 375                 380 tta cgc agc gtt ccg att ggt ggc acc gag taa                          1185
Leu Arg Ser Val Pro Ile Gly Gly Thr Glu
385                 390
```

<210> SEQ ID NO 24
<211> LENGTH: 394
<212> TYPE: PRT
<213> ORGANISM: Doritaenopsis hybrid cultivar
<220> FEATURE:
<223> OTHER INFORMATION: Doritaenopsis Sogo Vivien x Doritaenopsis Sogo Yenlin

<400> SEQUENCE: 24

```
Met Ala Pro Ala Met Glu Glu Ile Arg Arg Thr Gln Arg Ala Glu Gly
1               5                   10                  15

Pro Ala Ala Val Leu Ala Ile Gly Thr Ser Thr Pro Pro Asn Ala Leu
            20                  25                  30

Tyr Gln Ala Asp Tyr Pro Asp Tyr Tyr Phe Arg Ile Thr Asn Cys Glu
        35                  40                  45

His Leu Thr Asp Leu Lys Glu Lys Phe Lys Arg Met Cys Glu Lys Ser
    50                  55                  60

Met Ile Lys Lys Arg Tyr Met Tyr Leu Thr Glu Glu Phe Leu Lys Glu
65                  70                  75                  80

Asn Pro Asn Ile Cys Ala Phe Met Ala Pro Ser Leu Asp Ala Arg Gln
                85                  90                  95

Asp Ile Val Val Ala Glu Val Pro Lys Leu Ala Lys Glu Ala Ala Ala
            100                 105                 110

Arg Ala Ile Lys Glu Trp Gly His Pro Lys Ser Arg Ile Thr His Leu
        115                 120                 125

Ile Phe Cys Thr Thr Ser Gly Val Asp Met Pro Gly Ala Asp Tyr Gln
    130                 135                 140

Leu Thr Arg Leu Leu Gly Leu Arg Pro Ser Val Asn Arg Phe Met Leu
145                 150                 155                 160

Tyr Gln Gln Gly Cys Phe Ala Gly Gly Thr Val Leu Arg Leu Ala Lys
                165                 170                 175

Asp Leu Ala Glu Asn Asn Ala Gly Ala Arg Val Leu Val Val Cys Ser
            180                 185                 190

Glu Ile Thr Ala Val Thr Phe Arg Gly Pro Ser Glu Ser His Leu Asp
        195                 200                 205

Ser Leu Val Gly Gln Ala Leu Phe Gly Asp Gly Ala Ala Ala Ile Ile
    210                 215                 220

Val Gly Ser Asp Pro Asp Leu Ala Thr Glu Arg Pro Leu Phe Gln Leu
225                 230                 235                 240

Val Ser Ala Ser Gln Thr Ile Leu Pro Glu Ser Glu Gly Ala Ile Asp
```

```
                245                 250                 255
Gly His Leu Arg Glu Ile Gly Leu Thr Phe His Leu Leu Lys Asp Val
            260                 265                 270

Pro Gly Leu Ile Ser Lys Asn Ile Gln Lys Cys Leu Leu Glu Ala Phe
            275                 280                 285

Lys Pro Leu Gly Val Leu Asp Trp Asn Ser Ile Phe Trp Ile Ala His
            290                 295                 300

Pro Gly Gly Pro Ala Ile Leu Asp Gln Val Glu Thr Lys Leu Gly Leu
305                 310                 315                 320

Lys Ser Glu Lys Leu Ala Ala Ser Arg Asn Val Leu Ala Asp Tyr Gly
            325                 330                 335

Asn Met Ser Ser Ala Cys Val Leu Phe Ile Leu Asp Glu Met Arg Arg
            340                 345                 350

Arg Ser Ala Glu Ala Gly Gln Ser Thr Thr Gly Glu Gly Leu Glu Trp
            355                 360                 365

Gly Val Leu Phe Gly Phe Gly Pro Gly Leu Thr Val Glu Thr Val Val
            370                 375                 380

Leu Arg Ser Val Pro Ile Gly Gly Thr Glu
385                 390

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer CHI-dgF1

<400> SEQUENCE: 25
ttyctcgsyg gbgcmggygw vmgvgg                                              26

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer CHI-dgR1
<220> FEATURE:
<221> NAME/KEY: modified_base
<222> LOCATION: (5)..(5)
<223> OTHER INFORMATION: Inosine
<220> FEATURE:
<221> NAME/KEY: modified_base
<222> LOCATION: (8)..(8)
<223> OTHER INFORMATION: Inosine
<220> FEATURE:
<221> NAME/KEY: modified_base
<222> LOCATION: (20)..(20)
<223> OTHER INFORMATION: Inosine

<400> SEQUENCE: 26
cmggnganac vscrtkytyn ccratvat                                            28

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer CHI-dgF3
<220> FEATURE:
<221> NAME/KEY: modified_base
<222> LOCATION: (3)..(3)
<223> OTHER INFORMATION: Inosine
<220> FEATURE:
```

-continued

```
<221> NAME/KEY: modified_base
<222> LOCATION: (11)..(11)
<223> OTHER INFORMATION: Inosine
<220> FEATURE:
<221> NAME/KEY: modified_base
<222> LOCATION: (14)..(14)
<223> OTHER INFORMATION: Inosine

<400> SEQUENCE: 27
tmnkywcmgg nsmnttygar aaryt                                            25

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer CHI-dgR3
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (21)..(21)
<223> OTHER INFORMATION: Inosine

<400> SEQUENCE: 28
tynccratva tngwhtccar naybgc                                           26

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer PhCHI-GSP F1

<400> SEQUENCE: 29
atgctgctgc cattaacggg tca                                              23

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer PhCHI-GSP F2

<400> SEQUENCE: 30
tccgagaagg tctccgggaa ct                                               22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer PhCHI-GSP R1

<400> SEQUENCE: 31
gcattcgtca gcttcttgct ctct                                             24

<210> SEQ ID NO 32
<211> LENGTH: 21
<212> TYPE: DNA
```

-continued

<213> ORGANISM: Artificial Sequence
<220> FEATURE:
<223> OTHER INFORMATION: Description of Artificial Sequence: Synthetic
      primer PhCHI-GSP R2

<400> SEQUENCE: 32
atcacatcag tctcagccac a                                              21

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer PhCHI init

<400> SEQUENCE: 33
atggcagaaa cagtggcgac gccca                                          25

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer PhCHI term

<400> SEQUENCE: 34
tcaaacgact ccatcttgct c                                              21

<210> SEQ ID NO 35
<211> LENGTH: 723
<212> TYPE: DNA
<213> ORGANISM: Doritaenopsis hybrid cultivar
<220> FEATURE:
<223> OTHER INFORMATION: Doritaenopsis Sogo Vivien x Doritaenopsis Sogo
      Yenlin
<220> FEATURE:
<221> NAME/KEY: CDS
<222> LOCATION: (1)..(720)
<223> OTHER INFORMATION: Doritaenopsis hybrid cultivar chalcone
      isomerase

<400> SEQUENCE: 35

```
atg gca gaa aca gtg gcg acg ccc atc gag gtg gag gga gtg aag ttt      48
Met Ala Glu Thr Val Ala Thr Pro Ile Glu Val Glu Gly Val Lys Phe
1               5                   10                  15 ccg gcc gag atc tcg tcg ccg gcg acc tcg aaa cct cta ttt ctc ggt      96
Pro Ala Glu Ile Ser Ser Pro Ala Thr Ser Lys Pro Leu Phe Leu Gly
            20                  25                  30 ggc gca ggg gcg agg ggt ata gaa gtt gga gga aag ttt tta gcc gta     144
Gly Ala Gly Ala Arg Gly Ile Glu Val Gly Gly Lys Phe Leu Ala Val
        35                  40                  45 acc gcg atc gga gtg tac ttg gaa gcg gcg gtg att ccg gcg atc gcc     192
Thr Ala Ile Gly Val Tyr Leu Glu Ala Ala Val Ile Pro Ala Ile Ala
    50                  55                  60 gga aaa tgg acg ggg aag aag gcg gag aag ctc act gat tcg gtt gac     240
Gly Lys Trp Thr Gly Lys Lys Ala Glu Lys Leu Thr Asp Ser Val Asp
65                  70                  75                  80 ttt tac cga gac att att aca ggt tcc ttt gag aag ctg acg aga gtg     288
Phe Tyr Arg Asp Ile Ile Thr Gly Ser Phe Glu Lys Leu Thr Arg Val
                85                  90                  95 acg atg ctg ctg cca tta acg ggt caa cag tac tcc gag aag gtc tcc     336
Thr Met Leu Leu Pro Leu Thr Gly Gln Gln Tyr Ser Glu Lys Val Ser
            100                 105                 110 ggg aac tgc gtc gcc gca tgg aaa gcc gcc gga gaa tac aca gag gaa     384
Gly Asn Cys Val Ala Ala Trp Lys Ala Ala Gly Glu Tyr Thr Glu Glu
```

```
Gly Asn Cys Val Ala Ala Trp Lys Ala Ala Gly Glu Tyr Thr Glu Glu
        115                 120                 125 gaa gca acg gcc att aat aag ttt ctg gaa atc ttc aag cct aag aac      432
Glu Ala Thr Ala Ile Asn Lys Phe Leu Glu Ile Phe Lys Pro Lys Asn
130                 135                 140 ttt ctt cca ggc acc tcc atc atc ttc act cat tcc cct cat ggc tct      480
Phe Leu Pro Gly Thr Ser Ile Ile Phe Thr His Ser Pro His Gly Ser
145                 150                 155                 160 ctc act att gga ttt ttg gag ggg gat ggc gtt cct gtg gct gag act      528
Leu Thr Ile Gly Phe Leu Glu Gly Asp Gly Val Pro Val Ala Glu Thr
            165                 170                 175 gat gtg ata gag agc aag aag ctg acg aat gcg gtg ttg gaa tcc att      576
Asp Val Ile Glu Ser Lys Lys Leu Thr Asn Ala Val Leu Glu Ser Ile
            180                 185                 190 ata ggg gag aat gga gtt tct ccc gct gcg aaa cag agc ctg gct cgg      624
Ile Gly Glu Asn Gly Val Ser Pro Ala Ala Lys Gln Ser Leu Ala Arg
            195                 200                 205 agg ttt tca gag ctt ctg aat aag aaa gaa gac caa gaa gaa gaa gat      672
Arg Phe Ser Glu Leu Leu Asn Lys Lys Glu Asp Gln Glu Glu Glu Asp
210                 215                 220 ggg att ttg gat gtg gag aaa gcc aaa tta gag caa gat gga gtc gtt      720
Gly Ile Leu Asp Val Glu Lys Ala Lys Leu Glu Gln Asp Gly Val Val
225                 230                 235                 240 tga                                                                   723
```

<210> SEQ ID NO 36
<211> LENGTH: 240
<212> TYPE: PRT
<213> ORGANISM: Doritaenopsis hybrid cultivar
<220> FEATURE:
<223> OTHER INFORMATION: Doritaenopsis Sogo Vivien x Doritaenopsis Sogo Yenlin

<400> SEQUENCE: 36

```
Met Ala Glu Thr Val Ala Thr Pro Ile Glu Val Glu Gly Val Lys Phe
1               5                   10                  15

Pro Ala Glu Ile Ser Ser Pro Ala Thr Ser Lys Pro Leu Phe Leu Gly
            20                  25                  30

Gly Ala Gly Ala Arg Gly Ile Glu Val Gly Gly Lys Phe Leu Ala Val
        35                  40                  45

Thr Ala Ile Gly Val Tyr Leu Glu Ala Ala Val Ile Pro Ala Ile Ala
    50                  55                  60

Gly Lys Trp Thr Gly Lys Lys Ala Glu Lys Leu Thr Asp Ser Val Asp
65                  70                  75                  80

Phe Tyr Arg Asp Ile Ile Thr Gly Ser Phe Glu Lys Leu Thr Arg Val
                85                  90                  95

Thr Met Leu Leu Pro Leu Thr Gly Gln Gln Tyr Ser Glu Lys Val Ser
            100                 105                 110

Gly Asn Cys Val Ala Ala Trp Lys Ala Ala Gly Glu Tyr Thr Glu Glu
        115                 120                 125

Glu Ala Thr Ala Ile Asn Lys Phe Leu Glu Ile Phe Lys Pro Lys Asn
    130                 135                 140

Phe Leu Pro Gly Thr Ser Ile Ile Phe Thr His Ser Pro His Gly Ser
145                 150                 155                 160

Leu Thr Ile Gly Phe Leu Glu Gly Asp Gly Val Pro Val Ala Glu Thr
                165                 170                 175

Asp Val Ile Glu Ser Lys Lys Leu Thr Asn Ala Val Leu Glu Ser Ile
            180                 185                 190
```

```
Ile Gly Glu Asn Gly Val Ser Pro Ala Ala Lys Gln Ser Leu Ala Arg
        195                 200                 205

Arg Phe Ser Glu Leu Leu Asn Lys Lys Glu Asp Gln Glu Glu Glu Asp
    210                 215                 220

Gly Ile Leu Asp Val Glu Lys Ala Lys Leu Glu Gln Asp Gly Val Val
225                 230                 235                 240
```

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer F3H-dgF1
<220> FEATURE:
<221> NAME/KEY: modified_base
<222> LOCATION: (2)..(2)
<223> OTHER INFORMATION: Inosine
<220> FEATURE:
<221> NAME/KEY: modified_base
<222> LOCATION: (5)..(5)
<223> OTHER INFORMATION: Inosine
<220> FEATURE:
<221> NAME/KEY: modified_base
<222> LOCATION: (23)..(23)
<223> OTHER INFORMATION: Inosine

<400> SEQUENCE: 37
tnvgngayga rgabgarmgb ccnaa                                        25

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      primer F3H-dgR1

<400> SEQUENCE: 38
acbgcyygrt grtchgcrtt cttraa                                       26

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer F3H-dgF3
<220> FEATURE:
<221> NAME/KEY: modified_base
<222> LOCATION: (24)..(24)
<223> OTHER INFORMATION: Inosine

<400> SEQUENCE: 39
aarytbrgkt tygayatgwc hggng                                        25

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer F3H-dgR3
<220> FEATURE:
<221> NAME/KEY: modified_base
<222> LOCATION: (18)..(18)
<223> OTHER INFORMATION: Inosine

<400> SEQUENCE: 40
gghwsracvg tdatccangw btt                                          23

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer PhF3H-GSPF1

<400> SEQUENCE: 41
ttctcatacc caatcgggag                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer PhF3H-GSPF2

<400> SEQUENCE: 42
aatcgggagc cgcgattact                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer PhF3H-GSPR1

<400> SEQUENCE: 43
tctgtgtggc gcttcaggcc                                              20

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer PhF3H-GSPR2

<400> SEQUENCE: 44
tgaggtccgg ttgcgggcat ttt                                          23

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer PhF3H init

<400> SEQUENCE: 45
atggccccaa taccattcct accga                                        25

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      primer PhF3H term

<400> SEQUENCE: 46
ccttaagcta aaatctcatt taatgccttt gctcc                             35

```
<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      primer F3HDF3
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (21)..(21)
<223> OTHER INFORMATION: Inosine
<220> FEATURE:
<221> NAME/KEY: modified_base
<222> LOCATION: (24)..(24)
<223> OTHER INFORMATION: a, c, t, g, unknown or other

<400> SEQUENCE: 47
gcntayaayt aycargayyt ngtntt                                            26

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer F3HD-R4-2
<220> FEATURE:
<221> NAME/KEY: modified_base
<222> LOCATION: (3)..(3)
<223> OTHER INFORMATION: Inosine
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 48
gcnckytgna rngtnarncc                                                   20

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer F3HDF4
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (18)..(18)
```

<223> OTHER INFORMATION: a, c, t, g, unknown or other

<400> SEQUENCE: 49
gayytngtnt tygcnccnta ygg             23

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer F3HD-R3-2
<220> FEATURE:
<221> NAME/KEY: modified_base
<222> LOCATION: (4)..(4)
<223> OTHER INFORMATION: Inosine
<220> FEATURE:
<221> NAME/KEY: modified_base
<222> LOCATION: (7)..(7)
<223> OTHER INFORMATION: Inosine
<220> FEATURE:
<221> NAME/KEY: modified_base
<222> LOCATION: (10)..(10)
<223> OTHER INFORMATION: Inosine
<220> FEATURE:
<221> NAME/KEY: modified_base
<222> LOCATION: (13)..(13)
<223> OTHER INFORMATION: Inosine
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 50
datncknckn ccngcnccra angg             24

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer F3HDF5
<220> FEATURE:
<221> NAME/KEY: modified_base
<222> LOCATION: (10)..(12)
<223> OTHER INFORMATION: Inosine
<220> FEATURE:
<221> NAME/KEY: modified_base
<222> LOCATION: (18)..(18)
<223> OTHER INFORMATION: Inosine
<220> FEATURE:
<221> NAME/KEY: modified_base
<222> LOCATION: (21)..(21)
<223> OTHER INFORMATION: Inosine
<220> FEATURE:
<221> NAME/KEY: modified_base
<222> LOCATION: (27)..(27)
<223> OTHER INFORMATION: a, c, t, g, unknown or other

<400> SEQUENCE: 51
garttyaarn nnatggtngt ngarytnatg             30

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer F3HD-R1-3

```
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 52
ggrtcnckng cdatngccc                                              19

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      primer PhF3dH-F7

<400> SEQUENCE: 53
agggcgaagt taatggtgga ggcagtgata                                  30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
      primer PhF3dH-F8

<400> SEQUENCE: 54
aagttaatgg tggaggcagt gatatgctga                                  30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer PhF3dH-R6

<400> SEQUENCE: 55
cactgcctcc accattaact tcgcccttct                                  30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer PhF3dH-R5

<400> SEQUENCE: 56
cctccaccat taacttcgcc cttctctatt                                  30

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      primer PhF3dH-F11E4

<400> SEQUENCE: 57
```

```
aagaagcaaa tggcattctt aacctacctg                                       30
```

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      primer PhF3dH-R7G11

<400> SEQUENCE: 58

```
ttatcactgc ctccaccatt aacttcgccc                                       30
```

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer DFRD-F1
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

<400> SEQUENCE: 59

```
ttycaygtng cnacnccnat g                                                21
```

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer DFRD-R1
<220> FEATURE:
<221> NAME/KEY: modified_base
<222> LOCATION: (4)..(4)
<223> OTHER INFORMATION: a, c, t, g, unknown or other

<400> SEQUENCE: 60

```
datngcrtcr tcraacatyt c                                                21
```

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      primer DFRD-F2
<220> FEATURE:
<221> NAME/KEY: modified_base
<222> LOCATION: (15)..(15)
<223> OTHER INFORMATION: Inosine

<400> SEQUENCE: 61

```
atgaayttyc arwsnrarga ycc                                              23
```

<210> SEQ ID NO 62

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer DFRD-R2
<220> FEATURE:
<221> NAME/KEY: modified_base
<222> LOCATION: (4)..(4)
<223> OTHER INFORMATION: Inosine
<220> FEATURE:
<221> NAME/KEY: modified_base
<222> LOCATION: (10)..(10)
<223> OTHER INFORMATION: Inosine
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (19)..(19)
<223> OTHER INFORMATION: a, c, t, g, unknown or other

<400> SEQUENCE: 62
rcanatrtan ckncnrttng c                                           21

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer DFRD-F3
<220> FEATURE:
<221> NAME/KEY: modified_base
<222> LOCATION: (12)..(12)
<223> OTHER INFORMATION: a, c, t, g, unknown or other

<400> SEQUENCE: 63
garaaygarg tnathaarcc                                             20

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer DFRD-R3
<220> FEATURE:
<221> NAME/KEY: modified_base
<222> LOCATION: (7)..(7)
<223> OTHER INFORMATION: Inosine
<220> FEATURE:
<221> NAME/KEY: modified_base
<222> LOCATION: (13)..(13)
<223> OTHER INFORMATION: a, c, t, g, unknown or other

<400> SEQUENCE: 64
rtcrtcnarr tgnacraayt g                                           21

<210> SEQ ID NO 65
<211> LENGTH: 27
<212> TYPE: DNA
<213> ORGANISM: Artificial Sequence
<220> FEATURE:
<223> OTHER INFORMATION: Description of Artificial Sequence: Synthetic
      primer PhDFR-F1

<400> SEQUENCE: 65
```

```
ggtcatgcaa aaggtcgggc agcgtaa                                          27
```

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      primer PhDFR-F2

<400> SEQUENCE: 66

```
gtgatcttca catcttccgc aggaacagt                                        29
```

<210> SEQ ID NO 67
<211> LENGTH: 37
<212> TYPE: DNA
<213> ORGANISM: Artificial Sequence
<220> FEATURE:
<223> OTHER INFORMATION: Description of Artificial Sequence: Synthetic
      primer PhDFR-R4

<400> SEQUENCE: 67

```
atgattcatt aaaaatccga aaaaaagacc actacaa                               37
```

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer PhDFR-R3

<400> SEQUENCE: 68

```
aaccatgcat aataaagcag atgtgtaaat                                       30
```

<210> SEQ ID NO 69
<211> LENGTH: 32
<212> TYPE: DNA
<213> ORGANISM: Artificial Sequence
<220> FEATURE:
<223> OTHER INFORMATION: Description of Artificial Sequence: Synthetic
      primer PhDFR-F8A5

<400> SEQUENCE: 69

```
aaaaaatgga ggatgtgagg aagggtcctg tt                                    32
```

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence: Synthetic
      primer PhDFR-R5

<400> SEQUENCE: 70

```
acatgattca ttaaaaatcc gaaaaaaaga cca                                   33
```

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      primer ANS-dgF2
<220> FEATURE:
<221> NAME/KEY: modified_base
<222> LOCATION: (2)..(2)
<223> OTHER INFORMATION: a, c, t, g, unknown or other
<220> FEATURE:

```
<221> NAME/KEY: modified_base
<222> LOCATION: (14)..(14)
<223> OTHER INFORMATION: Inosine
<220> FEATURE:
<221> NAME/KEY: modified_base
<222> LOCATION: (23)..(23)
<223> OTHER INFORMATION: Inosine
<220> FEATURE:
<221> NAME/KEY: modified_base
<222> LOCATION: (26)..(26)
<223> OTHER INFORMATION: Inosine

<400> SEQUENCE: 71
tncarggbta yggnagyarr ytngcnrmya                              30

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: Synthetic
      primer ANS-dgR2
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (15)..(15)
<223> OTHER INFORMATION: Inosine
<220> FEATURE:
<221> NAME/KEY: modified_base
<222> LOCATION: (21)..(21)
<223> OTHER INFORMATION: Inosine

<400> SEQUENCE: 72
ggytcrcara anaynrccca ngada                                   25

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence: Synthetic
      primer PhANS3RACEGSP1

<400> SEQUENCE: 73
gcccacaccg acgtcagctc cctctcct                                28

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic
      primer PhANS3RACEGSP2

<400> SEQUENCE: 74
cgtcggggat gcgctcgaga tcctcagc                                28

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence: Synthetic
      primer PhANS5RACEGSP1

<400> SEQUENCE: 75
agtccgcggg ttcagtcggc cagatggt                                28
```

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      primer PhANS5RACEGSP2

<400> SEQUENCE: 76
ccgtcttctc cggcgggtag acgaggtg                                      28

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer PhANS init

<400> SEQUENCE: 77
atggccacca aagcaatccc acc                                           23

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer PhANS term

<400> SEQUENCE: 78
tcaatccaca ggcgccttct                                               20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer GerF3H-F

<400> SEQUENCE: 79
atgacgcctt taacgctcct                                               20

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
      primer GerF3H-R

<400> SEQUENCE: 80
ctagaccttm gtcgtctcat atacatg                                       27

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer GerDFR-F

<400> SEQUENCE: 81
atggaagagg attctccggc                                               20

<210> SEQ ID NO 82

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer GerDFR-R

<400> SEQUENCE: 82
ctattggcct tcttttgaac aacaaa                                          26

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      primer GerANS-F

<400> SEQUENCE: 83
atggtgattc aagcaaccac a                                               21

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Synthetic
      primer GerANS-R

<400> SEQUENCE: 84
ctagttttgc atcacttcgt ctttat                                          26

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer TorF3H1-F

<400> SEQUENCE: 85
atgagtccct tagccttgat gat                                             23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer TorF3H1-R

<400> SEQUENCE: 86
ttaatagaca tgagtggcca acc                                             23

<210> SEQ ID NO 87
<211> LENGTH: 1539
<212> TYPE: DNA
<213> ORGANISM: Torenia fournieri
<220> FEATURE:
<221> NAME/KEY: CDS
<222> LOCATION: (1)..(1536)
<223> OTHER INFORMATION: Torenia fournieri flavonoid 3'-hydroxylase

<400> SEQUENCE: 87 atg agt ccc tta gcc ttg atg atc cta agt acc tta tta ggg ttt ctc      48
Met Ser Pro Leu Ala Leu Met Ile Leu Ser Thr Leu Leu Gly Phe Leu
1               5                   10                  15 cta tac cac tct ctt cgc tta cta ctc ttc tcc ggc caa ggt cgc cga      96
```

-continued

```
                Leu Tyr His Ser Leu Arg Leu Leu Phe Ser Gly Gln Gly Arg Arg
                         20                  25                  30 cta cta cca cca ggt cca cgg ccg tgg ccg ctg gtg gga aac ctc ccg        144
Leu Leu Pro Pro Gly Pro Arg Pro Trp Pro Leu Val Gly Asn Leu Pro
         35                  40                  45 cac tta ggc ccg aag cca cac gcc tcc atg gcc gag ctc gcg cga gcc        192
His Leu Gly Pro Lys Pro His Ala Ser Met Ala Glu Leu Ala Arg Ala
     50                  55                  60 tac gga ccc ctc atg cac cta aag atg gga ttc gta cac gtc gtg gtg        240
Tyr Gly Pro Leu Met His Leu Lys Met Gly Phe Val His Val Val Val
 65                  70                  75                  80 gct tcg tcg gcg agc gcg gcg gag cag tgc ctg agg gtt cac gac gcg        288
Ala Ser Ser Ala Ser Ala Ala Glu Gln Cys Leu Arg Val His Asp Ala
                 85                  90                  95 aat ttc ttg agc agg cca ccc aac tcc ggc gcc aag cac gtc gct tac        336
Asn Phe Leu Ser Arg Pro Pro Asn Ser Gly Ala Lys His Val Ala Tyr
             100                 105                 110 aac tac gag gac ttg gtt ttc aga ccg tac ggt ccc aag tgg agg ctg        384
Asn Tyr Glu Asp Leu Val Phe Arg Pro Tyr Gly Pro Lys Trp Arg Leu
         115                 120                 125 ttg agg aag ata tgc gct cag cat att ttc tcc gtc aag gct atg gat        432
Leu Arg Lys Ile Cys Ala Gln His Ile Phe Ser Val Lys Ala Met Asp
    130                 135                 140 gac ttc agg cgc gtc aga gag gaa gag gtg gcc atc ctg agt cgc gct        480
Asp Phe Arg Arg Val Arg Glu Glu Glu Val Ala Ile Leu Ser Arg Ala
145                 150                 155                 160 cta gca ggc aaa agg gcg gta ccc ata ggc caa atg ctc aac gtg tgc        528
Leu Ala Gly Lys Arg Ala Val Pro Ile Gly Gln Met Leu Asn Val Cys
                165                 170                 175 gcc aca aac gcc cta tca cgc gtc atg atg ggg cgg cgc gtg gtg ggc        576
Ala Thr Asn Ala Leu Ser Arg Val Met Met Gly Arg Arg Val Val Gly
            180                 185                 190 cac gcg gat gga acc aac gac gcc aag gcg gag gag ttc aaa gcc atg        624
His Ala Asp Gly Thr Asn Asp Ala Lys Ala Glu Glu Phe Lys Ala Met
        195                 200                 205 gtc gtc gag ctc atg gtc ctc tcc ggt gtc ttc aac atc agt gat ttc        672
Val Val Glu Leu Met Val Leu Ser Gly Val Phe Asn Ile Ser Asp Phe
    210                 215                 220 atc ccc ttc ctc gag cct ctg gac ttg cag gga gtg gct tcc aag atg        720
Ile Pro Phe Leu Glu Pro Leu Asp Leu Gln Gly Val Ala Ser Lys Met
225                 230                 235                 240 aag aaa ctc cac gcg cgg ttc gat gca ttc ttg acc gag att gta cga        768
Lys Lys Leu His Ala Arg Phe Asp Ala Phe Leu Thr Glu Ile Val Arg
                245                 250                 255 gag cgt tgt cat ggg cag atc aac aac ggt ggt gct cat cag gat gat        816
Glu Arg Cys His Gly Gln Ile Asn Asn Gly Gly Ala His Gln Asp Asp
            260                 265                 270 ttg ctt agc acg ttg att tcg ttc aaa ggg ctt gac gat ggc gat ggt        864
Leu Leu Ser Thr Leu Ile Ser Phe Lys Gly Leu Asp Asp Gly Asp Gly
        275                 280                 285 tcc agg ctc act gac aca gaa atc aag gcg ctc ctc ttg aac ctt ttt        912
Ser Arg Leu Thr Asp Thr Glu Ile Lys Ala Leu Leu Leu Asn Leu Phe
    290                 295                 300 gct gcg gga acg gac acg acg tcg agc acg gtg gaa tgg gcc gta gcc        960
Ala Ala Gly Thr Asp Thr Thr Ser Ser Thr Val Glu Trp Ala Val Ala
305                 310                 315                 320 gaa ctc cta cgc cac cct aag aca tta gcc caa gtc cgg caa gag ctc       1008
Glu Leu Leu Arg His Pro Lys Thr Leu Ala Gln Val Arg Gln Glu Leu
                325                 330                 335 gac tcg gtc gtg ggt aag aac agg ctc gtc tcc gag acc gat ctg aat       1056
```

```
                                                                    -continued Asp Ser Val Val Gly Lys Asn Arg Leu Val Ser Glu Thr Asp Leu Asn
            340                 345                 350 cag ctg ccc tat cta caa gct gtc gtc aaa gaa act ttc cgc ctc cat        1104
Gln Leu Pro Tyr Leu Gln Ala Val Val Lys Glu Thr Phe Arg Leu His
                355                 360                 365 cct ccg acg ccg ctc tct cta ccg aga ctc gcg gaa gat gat tgc gag        1152
Pro Pro Thr Pro Leu Ser Leu Pro Arg Leu Ala Glu Asp Asp Cys Glu
        370                 375                 380 atc gac gga tac ctc atc ccc aag ggc tcg acc ctt ctg gtg aac gtt        1200
Ile Asp Gly Tyr Leu Ile Pro Lys Gly Ser Thr Leu Leu Val Asn Val
385                 390                 395                 400 tgg gcc ata gcc cgc gat ccc aag gtt tgg gcc gat ccg ttg gag ttt        1248
Trp Ala Ile Ala Arg Asp Pro Lys Val Trp Ala Asp Pro Leu Glu Phe
                405                 410                 415 agg ccc gaa cga ttc ttg acg ggc gga gaa aag gcc gac gtc gat gtc        1296
Arg Pro Glu Arg Phe Leu Thr Gly Gly Glu Lys Ala Asp Val Asp Val
                420                 425                 430 aag ggg aac gat ttc gaa ctg ata ccg ttc ggg gcg ggt cgt agg atc        1344
Lys Gly Asn Asp Phe Glu Leu Ile Pro Phe Gly Ala Gly Arg Arg Ile
            435                 440                 445 tgc gcc ggc gtt ggc ttg gga ata cgt atg gtc caa ctg ttg acg gcg        1392
Cys Ala Gly Val Gly Leu Gly Ile Arg Met Val Gln Leu Leu Thr Ala
450                 455                 460 agt ttg atc cat gca ttc gat ctg gac ctt gct aat ggg ctt ttg ccc        1440
Ser Leu Ile His Ala Phe Asp Leu Asp Leu Ala Asn Gly Leu Leu Pro
465                 470                 475                 480 caa aat ctg aac atg gaa gaa gca tat ggg ctt acg cta caa cgg gct        1488
Gln Asn Leu Asn Met Glu Glu Ala Tyr Gly Leu Thr Leu Gln Arg Ala
                485                 490                 495 gag cct ttg ttg gtc cac cct agg ctg cgg ttg gcc act cat gtc tat        1536
Glu Pro Leu Leu Val His Pro Arg Leu Arg Leu Ala Thr His Val Tyr
        500                 505                 510 taa                                                                    1539

<210> SEQ ID NO 88
<211> LENGTH: 512
<212> TYPE: PRT
<213> ORGANISM: Torenia fournieri

<400> SEQUENCE: 88

Met Ser Pro Leu Ala Leu Met Ile Leu Ser Thr Leu Leu Gly Phe Leu
1               5                   10                  15

Leu Tyr His Ser Leu Arg Leu Leu Leu Phe Ser Gly Gln Gly Arg Arg
                20                  25                  30

Leu Leu Pro Pro Gly Pro Arg Pro Trp Pro Leu Val Gly Asn Leu Pro
            35                  40                  45

His Leu Gly Pro Lys Pro His Ala Ser Met Ala Glu Leu Ala Arg Ala
        50                  55                  60

Tyr Gly Pro Leu Met His Leu Lys Met Gly Phe Val His Val Val Val
65                  70                  75                  80

Ala Ser Ser Ala Ser Ala Ala Glu Gln Cys Leu Arg Val His Asp Ala
                85                  90                  95

Asn Phe Leu Ser Arg Pro Pro Asn Ser Gly Ala Lys His Val Ala Tyr
                100                 105                 110

Asn Tyr Glu Asp Leu Val Phe Arg Pro Tyr Gly Pro Lys Trp Arg Leu
            115                 120                 125

Leu Arg Lys Ile Cys Ala Gln His Ile Phe Ser Val Lys Ala Met Asp
        130                 135                 140
```

```
Asp Phe Arg Arg Val Arg Glu Glu Val Ala Ile Leu Ser Arg Ala
145                 150                 155                 160

Leu Ala Gly Lys Arg Ala Val Pro Ile Gly Gln Met Leu Asn Val Cys
            165                 170                 175

Ala Thr Asn Ala Leu Ser Arg Val Met Met Gly Arg Arg Val Val Gly
        180                 185                 190

His Ala Asp Gly Thr Asn Asp Ala Lys Ala Glu Glu Phe Lys Ala Met
    195                 200                 205

Val Val Glu Leu Met Val Leu Ser Gly Val Phe Asn Ile Ser Asp Phe
210                 215                 220

Ile Pro Phe Leu Glu Pro Leu Asp Leu Gln Gly Val Ala Ser Lys Met
225                 230                 235                 240

Lys Lys Leu His Ala Arg Phe Asp Ala Phe Leu Thr Glu Ile Val Arg
            245                 250                 255

Glu Arg Cys His Gly Gln Ile Asn Asn Gly Gly Ala His Gln Asp Asp
        260                 265                 270

Leu Leu Ser Thr Leu Ile Ser Phe Lys Gly Leu Asp Asp Gly Asp Gly
    275                 280                 285

Ser Arg Leu Thr Asp Thr Glu Ile Lys Ala Leu Leu Leu Asn Leu Phe
290                 295                 300

Ala Ala Gly Thr Asp Thr Thr Ser Ser Thr Val Glu Trp Ala Val Ala
305                 310                 315                 320

Glu Leu Leu Arg His Pro Lys Thr Leu Ala Gln Val Arg Gln Glu Leu
            325                 330                 335

Asp Ser Val Val Gly Lys Asn Arg Leu Val Ser Glu Thr Asp Leu Asn
        340                 345                 350

Gln Leu Pro Tyr Leu Gln Ala Val Val Lys Glu Thr Phe Arg Leu His
    355                 360                 365

Pro Pro Thr Pro Leu Ser Leu Pro Arg Leu Ala Glu Asp Asp Cys Glu
370                 375                 380

Ile Asp Gly Tyr Leu Ile Pro Lys Gly Ser Thr Leu Leu Val Asn Val
385                 390                 395                 400

Trp Ala Ile Ala Arg Asp Pro Lys Val Trp Ala Asp Pro Leu Glu Phe
            405                 410                 415

Arg Pro Glu Arg Phe Leu Thr Gly Gly Glu Lys Ala Asp Val Asp Val
        420                 425                 430

Lys Gly Asn Asp Phe Glu Leu Ile Pro Phe Gly Ala Gly Arg Arg Ile
    435                 440                 445

Cys Ala Gly Val Gly Leu Gly Ile Arg Met Val Gln Leu Leu Thr Ala
450                 455                 460

Ser Leu Ile His Ala Phe Asp Leu Asp Leu Ala Asn Gly Leu Leu Pro
465                 470                 475                 480

Gln Asn Leu Asn Met Glu Glu Ala Tyr Gly Leu Thr Leu Gln Arg Ala
            485                 490                 495

Glu Pro Leu Leu Val His Pro Arg Leu Arg Leu Ala Thr His Val Tyr
        500                 505                 510

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      primer TorDFR-F
```

-continued

```
<400> SEQUENCE: 89
atgagcatgg aagtagtagt acca                                            24

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      primer TorDFR-R

<400> SEQUENCE: 90
ctattctatc ttatgttctc catgg                                           25

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      primer AtFT 2nd-F

<400> SEQUENCE: 91
gaaaccacct gtttgttcaa ga                                              22

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      primer AtFT 2nd-R

<400> SEQUENCE: 92
tcaattggtt ataaggaag aagc                                             24

<210> SEQ ID NO 93
<211> LENGTH: 28
<212> TYPE: DNA
<213> ORGANISM: Artificial Sequence
<220> FEATURE:
<223> OTHER INFORMATION: Description of Artificial Sequence: Synthetic
      primer PhF3dH-367F

<400> SEQUENCE: 93
cggtgcgcgg tggcgtatgc tgaggcgt                                        28

<210> SEQ ID NO 94
<211> LENGTH: 28
<212> TYPE: DNA
<213> ORGANISM: Artificial Sequence
<220> FEATURE:
<223> OTHER INFORMATION: Description of Artificial Sequence: Synthetic
      primer PhF3dH-394R

<400> SEQUENCE: 94
acgcctcagc atacgccacc gcgcaccg                                        28

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      primer PhF3dH-R7G12
```

-continued

```
<400> SEQUENCE: 95
caccctttgc ataaatttat gacatcaagc                                    30

<210> SEQ ID NO 96
<211> LENGTH: 36
<212> TYPE: DNA
<213> ORGANISM: Artificial Sequence
<220> FEATURE:
<223> OTHER INFORMATION: Description of Artificial Sequence: Synthetic
      primer PhCHS3-1038F

<400> SEQUENCE: 96
gtaacatgtc gagcgcttgc gttcttttca tactcg                             36

<210> SEQ ID NO 97
<211> LENGTH: 36
<212> TYPE: DNA
<213> ORGANISM: Artificial Sequence
<220> FEATURE:
<223> OTHER INFORMATION: Description of Artificial Sequence: Synthetic
      primer PhCHS3-1073R

<400> SEQUENCE: 97
cgagtatgaa aagaacgcaa gcgctcgaca tgttac                             36
```